US006949341B2

(12) United States Patent
Rothschild et al.

(10) Patent No.: US 6,949,341 B2
(45) Date of Patent: *Sep. 27, 2005

(54) DIAGNOSING GENETIC DISORDERS

(75) Inventors: Kenneth J. Rothschild, Newton, MA (US); Sanjay M. Sonar, Boston, MA (US); Jerzy Olejnik, Allston, MA (US)

(73) Assignee: The Trustees of Boston University, Boston, MA (US)

( * ) Notice: Subject to any disclaimer, the term of this patent is extended or adjusted under 35 U.S.C. 154(b) by 187 days.

This patent is subject to a terminal disclaimer.

(21) Appl. No.: 10/264,126

(22) Filed: Oct. 3, 2002

(65) Prior Publication Data

US 2003/0162198 A1 Aug. 28, 2003

Related U.S. Application Data

(63) Continuation of application No. 09/504,001, filed on Feb. 14, 2000, now Pat. No. 6,589,736, which is a continuation of application No. 08/479,389, filed on Jun. 7, 1995, now Pat. No. 6,057,096, which is a continuation of application No. 08/345,807, filed on Nov. 22, 1994, now Pat. No. 5,986,076, which is a continuation-in-part of application No. 08/240,511, filed on May 11, 1994, now Pat. No. 5,643,722.

(51) Int. Cl.⁷ .............................................. C12Q 1/68
(52) U.S. Cl. ........................ 435/6; 435/91.1; 435/91.2
(58) Field of Search .......................... 435/6, 91.1, 91.2

(56) References Cited

U.S. PATENT DOCUMENTS

| | | | | |
|---|---|---|---|---|
| 4,683,195 A | | 7/1987 | Mullis et al. ................... | 435/6 |
| 5,043,272 A | | 8/1991 | Hartley ........................ | 435/91 |
| 5,057,410 A | | 10/1991 | Kawasaki et al. ............. | 435/6 |
| 5,106,727 A | | 4/1992 | Hartley et al. ................. | 435/6 |
| 5,643,722 A | * | 7/1997 | Rothschild et al. ............ | 435/6 |
| 6,566,070 B2 | * | 5/2003 | Rothschild et al. ............ | 435/6 |

OTHER PUBLICATIONS

Adler–Storthz, et al., "Biotin–Avidin–Amplified Enzyme Immunoassay for Detection of Herpes Simplex Virus Antigen in Clinical Specimens," *Journal of Clinical Microbiology* 18: 1329–1334 (1983).
Baldwin, et al., "New Photolabile Phosphate Protecting Groups," *Tetrahedron* 46:6879–6884 (1990).
Bayer, et al., "Affinity Cytochemistry: The Localization of Lectin and Antibody Receptors on Erythrocytes Via the Avidin–Biotin Complex," *FEBS Letters* 68: 240–244 (1976).
Beard, et al., "Identification of Monoclonal Antibodies Against the Trypomastigote Stage of *Trypanosoma cruzi* by Use of Iminobiotinylated Surface Polypeptides," *Molecular and Biochemical Parasitology* 16: 199–212 (1985).
Bednarek and Bodanszky, "9–Fluorenylmethyl Esters" *Int. J. Peptide Protein Res.* 21:196–201 (1983).

Berenson et al., "Positive selection of viable cell populations using avidin–biotin immunoadsorption," *J. Immunol. Methods* 91:11–19 (1986).
Bradford, "A Rapid and Sensitive Method for the Quantitation of Microgram Quantities of Protein Utilizing the Principle of Protein–Dye Binding," *Analytical Biochemistry* 72: 248–254 (1976).
Brigati, et al., "Detection of Viral Genomes in Cultured Cells and Paraffin–Embedded Tissue Sections Using Biotin–Labeled Hybridization Probes," *Virology* 126:32–50 (1983).
Broker, et al., "Electron Microscopic Visualization of tRNA Genes With Ferritin–Avidin: Biotin Labels," *Nucleic Acids Research* 5:363–384 (1978).
Buckie and Cook, "Specific Isolation of Surface Glycoproteins from Intact Cells by Biotinylated Concanavalin A and Immobilized Streptavidin," *Analytial Biochemistry* 156: 463–472 (1986).
Casali, et al. "Human Monoclonals from Antigen–Specific Selection of B Lymphocytes and Transformation by EBV," *Science* 234:476–479 (1986).
Chandler and Ballard, "Multiple Biotin–Containing Proteins in 3T3–LI Cells," *Biochem. J.* 237:123–130 (1986).
Delius, et al., "Separation of Complementary Strands of Plasmid DNA Using the Biotin–Avidin System and ots Application to Heteroduplex Formation and RNA/DNA Hybridization in Electron Microscopy," *Nucleic Acids Research* 13:5457–5469 (1985).

(Continued)

*Primary Examiner*—James Ketter
(74) *Attorney, Agent, or Firm*—Medlen & Carroll, LLP

(57) ABSTRACT

This invention relates to agents and conjugates that can be used to detect and isolate target components from complex mixtures such as nucleic acids from biological samples, cells from bodily fluids, and nascent proteins from translation reactions. Agents comprise a detectable moiety bound to a photoreactive moiety. Conjugates comprise agents coupled to substrates by covalent bounds which can be selectively cleaved with the administration of electromagnetic radiation. Targets substances labeled with detectable molecules can be easily identified and separated from a heterologous mixture of substances. Exposure of the conjugate to radiation releases the target in a functional form and completely unaltered. Using photocleavable molecular precursors as the conjugates, label can be incorporated into macromolecules, the nascent macromolecules isolated and the label completely removed. The invention also relates to targets isolated with these conjugates which may be useful as pharmaceutical agents or compositions that can be administered to humans and other mammals. Useful compositions include biological agents such as nucleic acids, proteins, lipids and cytokines. Conjugates can also be used to monitor the pathway and half-life of pharmaceutical composition in vivo and for diagnostic, therapeutic and prophylactic purposes. The invention also relates to kits comprised of agents and conjugates that can be used for the detection of diseases, disorders and nearly any individual substance in a complex background of substances.

36 Claims, 26 Drawing Sheets

OTHER PUBLICATIONS

Diamandis and Christopoulos, "The Biotin–(Strept) Avidin System: Principles and Applications in Biotechnology," *Clin. Chem.* 37/5:625–636 (1991).

DiCesare et al., "A High–Sensitivity Electrochemiluminescence–Based Detection System for Automated PCR Product Quantitation," *BioTechniques* 15:152–59 (1993).

Duhamel and Johnson, "Use of Nonfat Dru Milk to Block Nonspecific Nuclear and Membrane Staining by Avidin Conjugates," *The Journal of Histochemistry and Cytochemistry* 33:711–714 (1985).

Eckermann, et al., "Sequen e at the Site of Attachment of an Affinity–Label Derivative of Puromycin on 23–S Ribosomal RNA of *Escherichia coli* Ribosomes," *Eur. J. Biochem.* 82: 225–234 (1978).

Elbe, et al. "Fetal Skin: A Site of Dendritic Epidermal T Cell Development," *The Journal of Immunology* 149:1694–1701 (1992).

Esteban, et al., "An Amplified Immunoperoxidase Assay to Detect Bovine Leukemia Virus Expression: Development and Comparison with Other Assays," *Cancer Research* 45:3231–3235 (1985).

Finn, et al., "Avidin–Biotiin Affinity Chromatorgraphy:Application to the Isolation of Human Placental Insulin Receptor," *Proc.Natl.Acad. Sci. USA* 81:7328–7332 (1984).

Finn and Hofmann, "Isolation and Characterization of Hormone Receptors," *Methods Biochem. Anal.* 26:244–274 (1980).

Gebeyhu, et al., "Novel Biotinylated Nucleotide– Analogs for Labeling and Colorimetric Detection of DNA," *Nucleic Acids Research* 15:4513–4534 (1987).

Gould, et al., "Use of the Biotin–Streptavidin Interaction To Improve Flavivirus Detection By Immunofluorescence and Elisa Tests," *Jounral of Virological Methods* 11:41–48 (1985).

Grabowski and Sharp, "Affinity Chromatography of Splicing Complexes: U2, U%, and U4+U6 Small Nuclear Ribonucleoprotein Particles in the Spliceosome," *Science* 233: 1294–1299 (1986).

Guerin–Reverchon, et al., "A Comparison of MEthods for the Detection of Human Papillomavirus DNA by in situ Hybridization with Biotinylated Proves on Human Carcinoma Cell Lines," *Jounral of Immunological Methods* 123:167–176 (1989).

Happ et al., "New Approach to the Synthesis of 2'(3')–O–Aminoacyl Oligoribonucleotides," *J. Org. Chem.* 52:5387–91 (1987).

Hazum. "Purification of Gonadotropin–Releasing Hormone Receptors," *Methods in Enzymology* 184:285–293 (1990).

Heckler et al., "Preparation of 2'(3')–O–Acyl–pCpA Derivatives as Substrates for T4 RNA Ligase–Mediated "Chemical Aminoacylation"," *Tetrahedron* 40:87–94 (1984).

Hudson, "Methodological Implications of Simultaneous Solid–Phases Peptide Synthesis. I. Comparison of Different Coupling Procedures," *J. Org. Chem.* 53:617–624 (1988).

Ito, et al., "Triplex Affinity Capture of a Single Copy Clone From a Yeast Genomic Library," *Nucleic Acids Research* 20:3524 (1992).

Johnson, et al., "Functional Covalent Complex Between Elongation Factor Tu and an Analog of Lysyl–tRNA," *Proc. Natl. Acad. Sci. USA* 75:3075–3079 (1978).

Jones, et al., "Elimination of the Non–specific Binding of Avidin to Tissue Sections," *Histochemical Journal* 19:264–268 (1987).

Kendall, et al., "Utilization of the Biotin/Avidin System to Amplify the Sensitivity of the Enzyme–Linked Immunosorbent Assay (ELISA)," *Journal of Immunological MEthods* 56:329–339 (1983).

Khorana, "Bacteriorhodopsin, a Membrane Protein That Uses Light to Translocate Protons," *The Journal of Biological Chemistry* 263:7439–7442 (1988).

Kohanski and Lane. "Homogeneous Functional Insulin Receptor from 3T3–LI Adipocytes." *The Journal of Biological Chemistry* 260: 5014–5025 (1985).

Krieg et al., "Photocrosslinking of the signal sequence of nascent preprolactin to the 54–kilodalton polypeptide of the signal recognition particle," *Proc. Natl. Acad. Sci. USA* 83:8604–08 (1986).

Kurzchalia et al., "tRNA–mediated labelling of proteins with biotin A nonreadioactive method for the detection of cell–free tranlation products," *Eur J Biochem* 172:663–668 (1988).

Langer, et al., "Enzymatic Symthesis of Biotin–Labeled Polynucleotides: Novel Nucleic Acid Affinity Probes," *Proc. Natl. Acad. Sci. USA* 78:6633–6637 (1981).

Leclercq, et al., "Interleukin–2 Stimulated T Cell Receptor Vv3 Positive Thymocytes Do Not Migrate to the Skin," *Immunology Letters* 28:135–142 (1991).

Lowry, et al., "Protein Measurement with the Folin Phenol Reagent," *Journal Biol. Chem.* 193:265–275 (1951).

McCray et al., "Properties and uses of photoreactive caged compounds," *Annu Rev Biophys Biophys Chem* 18:239–270 (1989).

Morgan, et al., "The selective isolation of novel cDNAs encoded by the regions surrounding the human interleukin 4 and 5 genes," *Nucleic Acids Research* 20(19):5173–5179 (1992).

Mortensson–Egnund and Kjeldsberg, "Improved ELISA for the Detection of Adenovirus antigen in Faeces Extracts by the Biotin/streptavidin Interaction," *Jounral of Virological Methods* 14:57–63 (1986).

Nakayama, et al., "Affinity Purification of the Opioid Receptor in NG 108–15 Cells Using an Avidin–biotin System with a Novel Elution Method," *FEBS Letters*, 208:278–282 (1986).

Nargeot, et al., "Time Course of the Increase in the Myocardial Slow Inward Current after a Photochemically Generated Concentration Jump of Intracellular cAMP," *Proc. Natl. Acad. Sci. USA* 80:2395–2399 (1983).

Neu and Heppel, "Nucleotide Sequence Analysis of Polyribonucleotides by Means of Periodate Oxidation Followed by Cleavage with an Amine," *J. Biol. Chem.* 239:2927–34 (1964).

Newman, et al., "Biotinylation of Peptide Hormones: Structural Analysis and Application to Flow Cytometry," *Methods in Enzymology* 184:275–285 (1990).

Nielsen, et al., "Sequence–Selective Recognition of DNA by Strand Displacement with a Thymine–Substituted Polyamide," *Science* 254:1497–1500 (1991).

Orr, "The Use of the 2–Iminobiotin–Avidin Interaction for the Selective Retrieval of Labeled Plasma Membrane Components," *The Journal of Biological Chemistry* 256: 761–766 (1981).

O'Shannessy, et al., "Quantitation of Glycoproteins on Electroblots Using the Biotin–Streptavidin Complex,", *Analytical Biochemistry* 163:201–209 (1987).

Otsuka, "Recovery of DNA Fragments Inserted by the "Tailing" Method: Regeneration of Pstl Restriciton Sites," *Gene* 13:339–346 (1981).

Paquet, "Introduction of 9–fluorenylmethyloxycarbonyl, Trichloroethoxycarbonyl, and Benzyloxycarbonyl Amine Protecting Groups into O–protected Hydroxyamino Acids Using Succinimidyl Carbonates," *Can. J. Chem.* 60:976–980 (1982).

Pillai, "Photoremovable Protecting Groups in Organic Synthesis," *Synthesis* 1–26 (1980).

Powell et al., "Molecular Diagnosis of Familial Adenomatous Polyposis," *N. Engl. J. Med.* 329:1982–87 (1993).

Promega Technical Bulletin No. 182; tRNA$^{nucend}$™: Non–Radioactive Translation Detection System. Sep. 1–16, 1993.

Qin, et al., ""Infectious" Transplantation Tolerance," *Science* 259:974–977 (1993).

Redeuilh, et al., "The Use of the Biotinyl Estradiol–Avidin System for the Prufication of "Nontrasnformed" Estrogen Receptor by Biohormonal Affinity Chromtography" *The Journal of Biological Chemistry* 260: 3996–4002 (1985).

Rigas, et al., "Rapid Plasmid Library Screening Using RecA–coated Biotinylated Probes," *Proc. Natl. Acad. Sci. USA* 83:9591–9595 (1986).

Rivnay, et al., "Use of Avidin–Biotin Technology for Liposome Targeting," *Methods in Enzymology* 149:119–123 (1987).

Saiki, et al., "Enzymatic Amplification of α–Globin Genomic Sequence and Restriction Site Analysis For Diagnosis of Sickle Cell Anemia," *Science* 230:1350–1354 (1985).

Saiki, et al., "Primer–Directed Enzymatic Amplification of DNA with a Thermostable DNA Polymerase," *Science* 239:487–491 (1988).

Sampson and Uhlenbeck, "Biochemical and physical characterization of an unmodified yeast phenylalanine transfer RNA transcribed in vitro," *Proc. Natl. Acad. Sci. USA* 85:1033–37 (1988).

Shimkus, et al., "Laboratory Methods: Synthesis and Characterization of Biotin–Labeled Nucleotide Analogs," *DNA* 5:247–255 (1986).

Shimkus, et al., "A Chemically Cleavable Biotinylated Nucleotide: Usefulness in the Recovery of Protein–DNA Complexes from Avidin Affinity Columns," *Proc. Natl. Acad. Sci. USA* 82:2593–2597 (1985).

Sieber, "Der 2–Trimethylsilylathyl–Rest als selektiv abspaltbare Carboxy–Schutzgruppe," *Helvetica Chimica Acta* 60:2711–2716 (1977).

Sigler, et al., "Formation of Oligopeptides During the Synthesis of 9–Fluorenylmethyloxycarbonyl Amino Acid Derivatives," *Biopolymers* 22:2157–2162 (1983).

Sonar et al., "Cell–Free Synthesis, Function Refolding, and Spectroscopic Characterization of Bacteriorhodopsin, an Integral Membrane Protein," *Biochem* 32:13777–13781 (1993).

Updyke et al., "Immunoaffinity Isolation of Membrane Antigens with Biotinylated Monoclonal Antibodies and Immobilized Streptavidin Matrices," *J. Immunol. Meth* 73:83–95 (1984).

White, et al., "The Polymerase Chain Reaction," *Trends. Gent.* 5 (1989).

Wilchek and Bayer, "Applications of Avidin–Biotin Technology: Literature Survey," *Methods in Enzymology* 184:14–45 (1990).

Wilchek and Bayer, "The Avidin–Biotin Complex in Bio-analytical Applications," *Analytical Biochemistry* 171:1–32 (1988).

Wormmeester et al., "A Simple Methods for Immunoselective Cell Separation with the Avidin–Biotin System," *J. Immunol. Meth.* 67:389–394 (1984).

Yolken, et al., "Enzyme Immunoassays for the Detection of Bacterial Antigens Utilizing Biotin–Labeled Antibody and PEroxidase Biotin–Avidin Complex," *Jounral of Immunological Methods* 56:319–327 (1983).

* cited by examiner

Step 1: Synthesis of Photocleavable Biotin

Step 2: Modification of the substrate by Photocleavable Biotin

Step 3: Isolation of the Modified Substrate using Avidin

Step 4: Detachment of Pure Substrate

1. Immobilize target protein/antibody conjugated to photocleavable biotin with streptavidin.

2. Release of target protein/antibody by illumination with light.

3. Release target with epitope conjugated to photocleavable biotin.

4. Separation of target protein from antibody using streptavidin binding and release of the antibody with light for recovery.

DIAGNOSING GENETIC DISORDERS

REFERENCE TO RELATED APPLICATIONS

This is a Continuation of application(s) 09/504,001 filed on Feb. 14, 2000 now U.S. Pat. No. 6,589,736 which is a continuation of application Ser. No. 08/479,389 filed on Jun. 7, 1995 which is now issued U.S. Pat. No. 6,057,096 dated on May 20, 2000, which is a continuation of application Ser. No. 08/345,807 filed on Nov. 22, 1994 which is now issued U.S. Pat. No. 5,986,076, which is a continuation-in-part of application Ser. No. 08/240,511 filed on May 11, 1994 which is now issued U.S. Pat. No. 5,643,722 dated Jul. 1, 1997.

RIGHTS IN THE INVENTION

This invention was made with United States Government support under grant number EM4727-03, awarded by the National Institutes of Health, and grant number DAAL03-92-G-0172, awarded by the Army Research Office, and the United States Government has certain rights in the invention.

BACKGROUND OF THE INVENTION

1. Field of the Invention

This invention relates to agents and conjugates used in the detection and isolation of targets from heterologous mixtures. Agents comprise a detectable moiety bound to a photoreactive moiety. Conjugates comprise agents which are coupled to substrates by one or more covalent bonds. These bonds can be easily and selectively cleaved or photocleaved with the application of electromagnetic radiation. Substrates which may be coupled to agents include amino acids, peptides, proteins, nucleotides, nucleic acid primers for PCR reactions and lipids. The invention also relates to rapid and efficient methods for the detection and isolation of targets, such as cells, nucleic acids and proteins, and to kits which contain these components.

2. Description of the Background

Basic scientific techniques including some of the major breakthroughs in molecular biology, chemistry and medicine have certain features in common. Two of these features are the specific detection and isolation of individual components from complex mixtures. For example, electrophoresis and chromatography are each widely utilized procedures to detect or isolate macromolecules from biological samples. These procedures take advantage of unique or identifiable molecular properties of the components to be isolated such as charge, hydrophobicity and molecular weight, to characterize and identify macromolecules. Depending on their method of isolation, macromolecules isolated can often be utilized as products in downstream processes.

Some of the more useful detection and isolation procedures take advantage of physical properties of the element of interest, the substrate, or of molecules which can be easily attached to substrates. One of the most widely used of these properties is radioactivity and radioactive labeling with radionuclides. For the most part, substances are not naturally radioactive and can be labeled with radioactive atoms, referred to as radionuclides, and detected using standard and well-known radiographic procedures. Radioactive elements are detectable because they emit large amounts of energy in the form of alpha, beta or gamma rays as they decay. Radioactivity is generally useful for labeling because the label is not affected by the physical state or chemical combination of the substance to be labeled. In addition, the specific radiation emitted can be identified by the nature of the radiation (e.g. α, β or γ), its energy and the half-life of the process. Targets can be identified in complex mixtures from the radiation profile emitted. Further, radioactively labeled substances can be followed radiographically in chemical pathways and biological systems.

Unfortunately, radioactivity is a hazard to both human health and the environment. The protection which must be afforded each worker is substantial. Special laboratory procedures, dedicated facilities and equipment, detailed record keeping and special training of laboratory personnel are all required for the safe use of radionuclides. Production of radioactive reagents is also very expensive as is safe disposal which drives up the cost of all experiments involving radioactive agents. Further, under present guidelines, all users of radioactivity require specialized supervision and federal regulations must be strictly and carefully adhered to requiring an enormous amount of record keeping.

Radioactive labeling methods also do not always provide a means of isolating products in a form which can be further utilized. The presence of radioactivity compromises utility for further biochemical or biophysical procedures in the laboratory and in animals. This is clear in the case of in vitro or in vivo expression of proteins biosynthetically labeled with radioactive amino acids or tagged with other radioactive markers. The harm or at least potential harm of the radioactivity outweighs the benefits which might be produced by the protein composition.

Disposal of radioactive waste is also of increasing concern both because of the potential risk to the public and the lack of radioactive waste disposal sites. In addition, the use of radioactive labeling is time consuming, in some cases requiring as much as several days for detection of the radioactive label. The long time needed for such experiments is a key consideration and can seriously impede research productivity. While faster methods of radioactive detection are available, they are expensive and often require complex image enhancement devices.

There are many other detectable physical properties which can exist in chemicals and chemical moieties that can be used to detect and isolate substances. One of these physical properties is the property of luminescence which includes the phenomena of fluorescence and phosphorescence. Fluorescent chemicals emit radiation due to the decay of the molecule which has been excited to a higher electronic state due to the absorption of radiation. Phosphorescent molecules can emit radiation for a much longer time intervals. Detection of the specific wavelength of radiant energy emitted allows for the detection of targets which may be associated with the luminescent chemicals.

Bioluminescence is rapidly becoming a widely used method for labeling many different types of compounds. Basically, a reduced substrate is reacted with oxygen and converted into an oxidized product with an elevated or excited electronic state. The excited molecule decays to the ground state and in the process, emits photons of light. This process has been found to occur in several strains of bacteria and fungi, in marine invertebrates such as sponges, and in shrimp and jellyfish. Bacteria which emit light are often found living symbiotically with fish in special luminescent organs. A wide variety of terrestrial organisms such as earthworms, centipedes and insects also possess bioluminescent properties.

One group of compounds which undergo oxidation with the emission of light are referred to as luciferins although their individual structure may vary. The oxidized products are termed oxy-luciferins and the enzymes which catalyze the process luciferases. The overall process is endothermic requiring chemical energy stored in one to two molecules of adenosine triphosphate (ATP) per photon of light produced. Two types of luciferase systems that have been widely used in molecular biology are the bacterial system (*Vibrio harveyi* or *V. fischeri*) and the firefly system (*Photinus pyralis*).

Other labels which impart detectable properties to a substrate include chemicals with a unique absorption spectrum, electron spin resonance spectrum, optical activity, Raman spectrum or resonance Raman. spectrum Such labels are widely used in many fields including medicine, molecular biology and chemistry. For example, the visible or infrared absorption spectrum of a molecule often constitutes a unique fingerprint which allows the molecule to be identified even in the presence of a complex mixture. In the case of visible absorption, the molecule absorbs radiant energy over a specific wavelength range because of the presence of an excited electronic state of the molecule whose energy of transition from the ground state falls in the range 1.5–3 eV. In the case of infrared absorption, bands are detected due to the excitation of vibrational modes of the molecule. The frequency of these bands provides information about the presence or absence of characteristic molecular groups such as disulfides, carbonyls and aromatic groups.

In another application of the spectroscopic properties of molecules, nuclear magnetic resonance (NMR) spectroscopy has been extensively used to identify specific molecules in a mixture. The nuclei of atoms, such as protons in hydrogen atoms, which possess a net magnetic moment, will align when placed into a magnetic field with that field and will precess about that field with a frequency (the Lamar frequency) dependent on the individual properties of the particle. To determine the NMR spectrum, a sample of protons is placed within a strong magnetic field and irradiated with a range of radio frequencies at a 90° angle with respect to the main field. This treatment causes all the protons in the sample to absorb energy at their characteristic frequency, flipping their magnetic orientations 90° with respect to their original state. After the applied field is switched off, the molecules gradually relax to precess about the main field. Receiver coils which surround the sample detect the frequencies of precessing spins as a set of oscillating electric currents which constitute the NMR signal.

All of these methods suffer from similar disadvantages. For the most part, targets do not have unique detectable properties such as inherent radioactivity or fluorescence. Labels must be attached which are themselves detectable and therefore make the target detectable. However, the labeling process can result in a labeled product that is in some way permanently damaged. For example, fluorescent chemicals can be extremely toxic to cells. Long term exposure can result in a high degree of cell death. Often, the labeling compound may have detrimental effects on a target's structure or activity. Protein structure is often adversely affected by the attachment of a detectable chemical moiety. Labeling of nucleic acids can interfere with their ability to be translated, transcribed by polymerases or interact with DNA binding proteins. In most cases, the chemical moiety must be removed. Further, the methods for removal of these chemical moieties which have detectable physical properties often result directly in alteration of the molecule or cell death.

There are a number of procedures, both complex and simple, which have been used to selectively detect and isolate target substrates. One procedure which has revolutionized and greatly accelerated the detection and identification of nucleic acids is polymerase chain reaction (PCR) technology. The principle concept of PCR is the rapid, large-scale amplification of unique or even non-unique nucleic acid sequences in biological samples. Using labeled primers with specific or random sequences, the genetic code of very small quantities of nucleic acids can be detected, amplified in number and subsequently characterized through repetitive polymerization events. Although the nucleic acids formed are new, the sequence of the original sample is maintained and can be easily determined. As a nucleic acid sequence is the biological. code for the construction of virtually all proteins, the origin, evolutionary age, structure and composition of nearly any biological organism or sample can be determined from knowledge of the sequence. The procedure has been proved useful in molecular and evolutionary biology, and has demonstrated applications in the detection, treatment and prevention of diseases and disorders in humans.

PCR technology, although revolutionary, carries with it the same limitations as many conventional detection and isolation procedures. Label which has been incorporated into primers and ultimately newly formed nucleic acids must be removed. This process, when possible, is fairly time consuming and often results is modification or destruction of the nucleic acid.

Another example of a process to render a substance specifically detectable is to use binding molecules which have a particular affinity for selected other molecules as occurs between binding of an antigen to an antigen-specific antibody. These chemical pairs, sometimes referred to as coupling agents, have been used extensively in detection and isolation procedures. Normally one of the molecules in this pair is immobilized on an affinity medium such as used in chromatographic packing material or a magnetic bead and used in the isolation of the target molecule. Some of the more useful coupling agents are biotin and avidin or the related protein, streptavidin. These agents have been used in many separation techniques to facilitate isolation of one component or another from complex mixtures Biotin, a water-soluble vitamin, is used extensively in biochemistry and molecular biology for a variety of purposes including macromolecular detection, purification and isolation, and in cytochemical staining. Biotin also has important applications in medicine in the areas of clinical diagnostic assays, tumor imaging and drug delivery, and is used extensively in the field of affinity cytochemistry for the selective labeling of cells, subcellular structures and proteins.

Biotin's utility stems from its ability to bind strongly to the tetrameric protein avidin, found in egg white and the tissues of birds, reptiles and amphibians, or to its chemical cousin, streptavidin, isolated from the bacterium *Streptomyces*. Typically, biotin or a derivative of biotin is first bound directly to a target molecule, such as a protein or oligonucleotide, or to a probe using specific chemical lineage. The interaction of the linked biotin with either streptavidin or avidin conjugated to an affinity medium such as magnetic or sepharose beads is then used in the isolation of the target molecule. Alternatively, the interaction of the covalently linked biotin with avidin or streptavidin conjugated to an enzyme such as horseradish peroxidase (HRP) which catalyzes a chromogenic reaction is used for detection of the target molecule. Macromolecules that have been isolated using biotin-avidin technology are shown in Tables 1 and 2.

TABLE 1

Macromolecules Isolated by Direct Biotinylation

| Biotinylated Targets | Elution Conditions | References |
|---|---|---|
| Membrane proteins and glycoproteins | acetate, pH 4 | 1, 2 |
| Antibodies | low pH | 3 |
| Enzymes | non-physiological | 4 |
| t-RNA | 6 M guanidine-HCl, pH 2.5 | 5 |
| rRNA | 70% formic acid | 6 |

TABLE 1-continued

Macromolecules Isolated by Direct Biotinylation

| Biotinylated Targets | Elution Conditions | References |
|---|---|---|
| nucleosomes | SS-reduction of cleavable biotin | 7, 8 |
| DNA | non-physiological | 9 |

1. G. A. Orr, J. Biol. Chem. 256: 761, 1981.
2. C. A. Beard et al., Mol. Biochem. Parasitol. 16: 199, 1985.
3. E. A. Bayer et al., FEBS Lett. 68: 240, 1976.
4. C. S. Chandler et al., Biochem. J. 237: 123, 1986.
5. T. R. Broker et al., Nucl. Acids Res. 5: 363, 1978.
6. D. J. Eckermann et al., Eur. J. Biochem. 82: 225, 1978.
7. M. L. Shimkus et al., Proc. Natl. Acad. Sci. USA 82: 2593, 1986.
8. M. L. Shimkus et al., DNA 5: 247, 1986.
9. P. L. Langer et al., Proc. Natl. Acad. Sci. USA 78: 6633, 1981.

TABLE 2

Biological Materials Isolated Using Biotinylated Binding Molecules

| Target Molecules | Binding Molecules | Elution Conditions | Refs. |
|---|---|---|---|
| Glycoproteins | conconavalin A | 2% SDS | 10 |
| Membrane Antigens | antibody | SDS (boiling) | 11 |
| Estrogen Receptor | estradiacetate, | estradiol | 12 |
| Insulin Receptor | insulin | acetate, pH 5.0 biotin | 13, 14 |
| Opoid Receptor | enkephalin | enkephalin | 15 |
| Human B lymphocytes | antigen | selection by FACS | 16 |
| Lymphocyte subpopulations | monoclonal antibody | Mechanical agitation, erythrocyte lysis | 17, 18, 19 |
| Plasmid DNA | DNA | 0.1 M NaOH | 20 |
| Spliceosomes | RNA | 90° C. in SDS | 21 |
| Recombinant Plasmids | DNA | Cleavable biotin Heat, low ionic strength and phenol | 22 |

10. J. W. Buckie et al., Anal. Biochem. 156: 463, 1986.
11. T. V. Updyke et al., J. Immunol. Methods 73: 83, 1984.
12. G. Redeulih et al., J. Biol. Chem. 260: 3996, 1985.
13. F. M. Finn et al., Proc. Natl. Acad. Sci. USA 81: 7328, 1984.
14. R. A. Kohanski et al., J. Biol. Chem. 260: 5014, 1985.
15. H. Nakayama et al., FEBS Lett. 208: 278, 1986.
16. P. Casali et al., Sci. 234: 476, 1986.
17. J. Wormmeester et al., J. Immunol. Methods 67: 389, 1984.
18. P. J. Lucas et al., J. Immunol. Methods 99: 123, 1987.
19. R. J. Berenson et al., J. Immunol. Methods 91: 11, 1986.
20. H. Delius et al., Nucl. Acids Res. 13: 5457, 1985.
21. P. J. Grabowski et al., Sci. 233: 1294, 1986.
22. B. Riggs et al., Proc. Natl. Acad. Sci. USA 83: 9591, 1986.

While the utility of biotin continues to grow, there still exists major drawbacks in the use of biotin-streptavidin technology for many applications. This problem stems from the high affinity between biotin and streptavidin, precisely the molecular characteristic which makes it most useful. Once a target molecule or cell is isolated through the streptavidin-biotin interaction, release of the target molecule requires disruption of this interaction. Dissociation of biotin from streptavidin requires very harsh conditions such as 6–8 molar (M) guanidinium-HCl, pH 1.5. Such conditions also denature, and thereby inactivate, most proteins and destroy most cells.

For example, a biotin derivative containing a N-hydroxysuccinimide ester group is commonly used to link biotin through an amide bond to proteins and nucleic acids. Selective cleavage of this linkage disrupts similar native chemical bonds in associated molecules. Biotin is also often used in the isolation of specific cells from a heterogeneous mixture of cells by binding a biotinylated antibody directed against a characteristic cell surface antigen. The interaction of the biotinylated antibody with streptavidin-coated magnetic beads or sepharose particles can then be used effectively to isolate target cells. Disruption of the antibody-antigen interaction normally requires exposure of cells to conditions such as low pH or mechanical agitation which are adverse to the cell's survival. In general recovery of the target in a completely unmodified form is not possible.

Once the biotinylated DNA is bound to streptavidin it can only be released with extreme difficulty. Many diverse methods to remove the streptavidin molecule have been suggested including digestion by proteinase K (M. Wilchek and E. A. Bayer, Anal. Biochem. 171:1, 1988). Proteinase K also digests nearby proteins and does a fairly poor job of completely digesting the streptavidin. Significant amounts of the streptavidin molecules remain attached, and further, removal of streptavidin does not release the biotin. Further, biotinylated DNA interferes with subsequent use in a variety of methods including transformation of cells and hybridization based assays used for detection of genetic diseases.

The essentially irreversible binding of biotin and streptavidin is also a serious limitation for the performance of multiple or sequential assays to detect a specific type of biomolecule, macromolecular complex, virus or cell present in a single sample. Normally, only a single assay can be performed because the enzyme detection system is streptavidin-based and streptavidin remains firmly bound to the biotinylated target or target probe. While different chromogenic systems for detection are available, they are only of limited applicability in situations where large numbers of probes are needed.

An additional problem in the use of biotin-avidin technology is the presence of endogenous biotin, either free or complexed to other molecules, inside the sample to be purified or assayed. In this case, the endogenous biotin can result in the isolation or detection of non-target molecules. This can be a particularly severe problem in cases where a high signal-to-noise ratio is needed for accurate and sensitive detection.

To remove biotin from an attached molecule, several chemically cleavable biotin derivatives have been produced. Immunopure NHS-SS-biotin (Pierce Chemical; Rockford, Ill.) consists of a biotin molecule linked through a disulfide bond and an N-hydroxysuccinimide ester group that reacts selectively with primary amines. Using this group, NHS-SS-biotin can be linked to a protein and then the biotin portion removed by cleaving the disulfide bond with thiols. This approach is of limited use since thiols normally disrupt native disulfide bonds in proteins. Furthermore, the cleavage still leaves the target cell or molecule modified since the spacer arm portion of the complex is not removed and the cleaving buffer must be eliminated from the sample.

One method for removal of biotin is the use of disulfide-based cleavable biotins. However, the cleaved molecules possess a reactive sulfhydryl group which has a strong tendency to form disulfide bonds with other components of the mixture. Functional activity of these substances containing sulfhydryl groups is severely compromised. Typically, activity of such protein is decreased or eliminated and such nucleic acids will no longer hybridize rendering them useless for cloning. This method is also slow and requires the preparation of complex solutions.

An additional limitation of biotin-avidin technology is the difficulty of developing automated systems for the isolation and/or detection of targets due to the problems of releasing the target from the biotin-avidin binding complex. This requires addition of specific chemical reagents and careful monitoring of the reactions.

Biotin-avidin technology has been combined with PCR techniques for the detection and isolation of nucleic acids and specific sequences. However, there still remains a fundamental problem which relates to the difficulty of removing the incorporated biotin. This is normally not possible using conventional biotins without irreversibly altering the structure of the DNA. As discussed, biotinylation can interfere with subsequent application of biotinylated probes as well as alter the properties of the PCR product.

PCR products that contain biotinylated nucleotides or primers which are required for isolation cannot be used in conjunction with biotinylated hybridization probes. The presence of biotin on the PCR product cause false signals from the avidin based enzyme-linked detection system. Biotin incorporation into DNA interferes with strand hybridization possibly due to the spacer arms linking the nucleotides to the biotin molecules. Further, PCR products that are biotinylated are not suitable material for cloning. PCR products which contain biotinylated nucleotides are difficult to analyze. Incorporation of biotinylated nucleotides into DNA causes a retardation of mobility during gel electrophoresis in agarose. This mobility shift renders characterization of PCR products difficult. As proper DNA-DNA hybridization is the basis for sensitive and accurate characterization and sensitive assays, biotin-avidin binding systems are seriously disadvantaged.

Other coupling partners which can be used to detect and isolate target substances are cell adhesion molecules (CAMs). One of the well characterized types is the endothelial cell adhesion molecule, LEC-CAM (leukocyte endothelial cell-cell adhesion molecule), now called selectin. This molecule selectively binds to leukocytes. Its natural function is to facilitate the transport of leukocytes through an endothelial layer of cells such as postcapillary venules to sites of inflammation or tissue damage. There are many of these adhesion molecules which have been identified in humans and other mammals that range in binding specificity from the very general to the highly specific. These include the endothelial cell adhesion ligands ICAM-1, VCAM-1 and ELAM-1, the β-integrins which consists of a family of three proteins LFA-1, Mac-1, VLA-4, MO-1 and p150/95, carbohydrate binding CAMs that appear on endothelial cells, platelets, and leukocytes, and the cadherins, calcium dependent CAMs present on most cells. Attachment of these molecules or the creation of fused proteins containing adhesion domains can be used to facilitate isolation and detection of binding partners. However, once binding has occurred, complex, expensive and time consuming biochemical manipulations and sometimes fairly harsh chemical treatments are necessary to dissociate the molecules. Further, application of these molecules for general use is limited as binding partners must be located for each target of interest Other coupling partners include nucleic acids and nucleic acid binding proteins, lipids and lipid binding proteins, and proteins or specific domains which have a particular affinity for each other. These coupling partners suffer from similar drawbacks as the biotin-avidin system and the adhesion molecules.

Another fairly ubiquitous method of detection and isolation is gel electrophoresis. In this process, a uniform matrix or gel is formed of, for example, polyacrylamide, to which is applied an electric field. Mixtures applied to one end of the gel will migrate through the gel according to their size and interaction with the electric field. Mobility is dependent upon the unique characteristics of the substance such as conformation, size and charge. Mobilities can be influenced by altering pore sizes of the gel, such as by formation of a concentration or pH gradient, or by altering the composition of the buffer (pH, SDS, DOC, glycine, salt). One- and two-dimensional gel electrophoresis are fairly routine procedures in most research laboratories. Target substances can be purified by passage through and/or physical extraction from the gel.

Methods for the detection and isolation of targets substances also include centrifugation techniques such as equilibrium-density-gradient centrifugation. This process is based on the principal that under high centrifugal forces, stable gradients win be established in salt solutions. Mixtures subjected to high speed centrifugation will segregate individual. components according to their specific densities. Although useful, all of these procedures are more quantitative than qualitative.

A major advance in detection and isolation methodology was the advent of liquid chromatography. Chromatography, and in particular column chromatography, comprises some of the most effective and flexible purification methods available. Common to most procedures is the use of open cylinders containing a hydrated matrix material. Some of the typical matrix materials which are presently used, for example, in gel filtration, affinity chromatography and ion exchange chromatography, include sepharose (bead formed gel prepared from agarose: Pharmacia Biotech; Piscataway, N.J.), sephadex (a bead-formed gel prepared by cross-linking dextran with epichlorohydrin: Pharmacia Biotech; Piscataway, N.J.) and sephacryl (covalently cross-linked allyl dextran with N,N'-methylene bisacrylamide: Pharmacia Biotech; Piscataway, N.J.). Basically, a heterogenous sample or mixture is applied to the top of the column followed with a suitable buffer. Substances within the mixture display differential migration through the column in relation to other materials within the sample and is collected in fractions at the other end of the column Fractions are individually analyzed for the presence of target and positive fractions pooled.

Alternatively, target in the sample may selectively bind to the column material in the presence of buffer a process known as affinity chromatography. After binding, unbound material is removed by continuously washing the column with buffer. Target molecules are subsequently released from the column by application of an elution buffer which causes dissociation. Fractions are collected as they elute off of the column and collected. In gel-exclusion chromatography, a cross-linked dextran is utilized as column matrix material. Cross-linking can be varied to alter the effective pore size of the column material and the dextran can be coupled to a wide variety of chemical moieties to selectively capture target. Ion-exchange chromatography takes advantage of the fact that targets, for example proteins, can differ enormously in their affinity for positive or negative charges on column materials. The affinity of a material for a target is proportional to the salt concentration of the buffer. By raising or lowering the salt concentration, it is possible to change affinity of target to column material.

Affinity column chromatography makes use of chemical groups that have special attraction to the targets of interest. For example, enzymes preferentially bind to certain naturally associated cofactors. Column materials with attached cofactors will selectively bind to such target enzymes. Enzyme purification becomes a relatively simple and straightforward matter. In a similar fashion, enzyme-specific antibodies can be coupled either covalently or non-covalently to a column matrix. The unique affinity of an antibody for its target antigen allows for the selective removal of target from a heterologous mixture of substances. Detection and isolation is again a fairly simple matter.

Two relatively well-established procedures, high-performance liquid chromatography (HPLC) including reverse-phase HPLC and size-exclusion HPLC, and the more recent technique fast-performance liquid chromatography (FPLC) which can handle larger sample volumes than HPLC, is based on standard chromatographic techniques, but using extremely high pressures (5,000 to 10,000 psi and more). Due to the higher pressures, finer column materials can be utilized and separations can be performed faster and with better resolution.

Although chromatography is an invaluable tool it too has its limits. Materials to be separated must be solubilized into a suitable buffer which will not adversely affect the column. Further, substrate mixtures and targets must be capable of passing through a column matrix in a reasonable period of time. Although HPLC can sometimes shorten this time period, only small quantities can be detected and the high pressures can damage isolated column material.

SUMMARY OF THE INVENTION

The present invention overcomes the problems and disadvantages associated with current strategies and designs and provides new methods for the detection and isolation of molecules from complex mixtures.

One embodiment of the invention is directed to bioreactive agents comprising a detectable moiety bonded to a photoreactive moiety wherein the photoreactive moiety contains at least one group capable of covalently bonding to a substrate to form a conjugate that can be selectively photocleaved to release said substrate. Detectable moieties should have a selectively detectable physical property such as fluorescence, absorption or an ability to specifically bind to a coupling agent such as avidin or streptavidin, antibodies, antigens or binding proteins. The photoreactive moiety should be capable of forming one or more covalent bonds with a chemical group of a substrate. Those covalent bonds may be cleaved or photocleaved with the electromagnetic radiation releasing the substrate.

The bioreactive agent may have a chemical structure selected from the group consisting of:

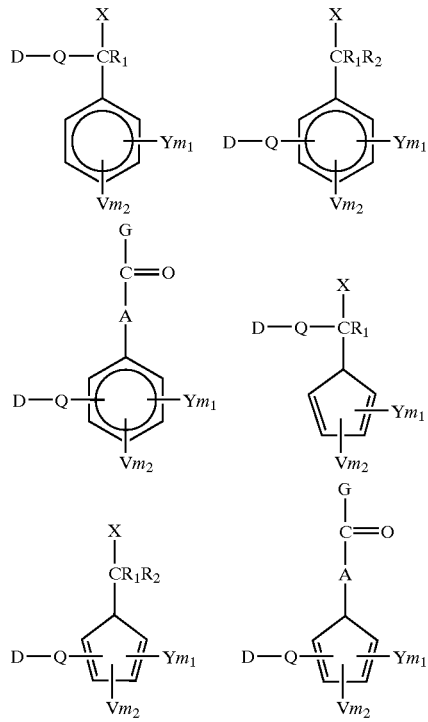

wherein X is selected from the group consisting of a halogen, $N_2$, $CH_2$-halogen, —N=C=O, —N=C=S, —S—S—R, $NC_2H_4$, —$NC_4H_2O_2$, —OH, —$NHNH_2$, —OP$(OR_3)N(R_4)R_5$ and —OCO-G, wherein G is selected from the group consisting of a halogen, $N_3$, O-esters and N-amides; $R_1$, $R_2$, $R_3$, $R_4$ and $R_5$ are selected from the group consisting of hydrogen, alkyls, substituted alkyls, aryls and substituted aryls, —$CF_3$, —$NO_2$, —COOH and —COOR, and may be the same or different; A is a divalent functional group selected from the group consisting of —O—, —S— and —$NR_1$; Y comprises one or more polyatomic groups which may be the same or different; V comprises one or more optional monoatomic groups which may be the same or different; Q comprises an optional spacer moiety; m1 and m2 are integers from 0–5 and may be the same or different; and D comprises a detectable moiety which is distinct from $R_1$–$R_5$.

Another embodiment of the invention is directed to conjugates comprising a bioreactive agent photocleavably coupled to a substrate wherein said agent comprises a detectable moiety bonded to a photoreactive moiety, wherein said conjugate can be selectively cleaved with electromagnetic radiation to release said substrate. Suitable substrates which can be coupled to the bioreactive agent include proteins, peptides, amino acids, amino acid analogs, nucleic acids, nucleosides, nucleotides, lipids, vesicles, detergent micells, cells, virus particles, fatty acids, saccharides, polysaccharides, inorganic molecules, metals, and derivatives and combinations thereof Substrates may be pharmaceutical agents such as cytokines, immune system modulators, agents of the hematopoietic system, chemotherapeutic agents, radio-isotopes, antigens, anti-neoplastic agents, recombinant proteins, enzymes, PCR products, receptors, hormones, vaccines, haptens, toxins, antibiotics, nascent proteins, cells, synthetic pharmaceuticals and derivatives and combinations thereof.

Conjugates may have a chemical structure selected from the group consisting of:

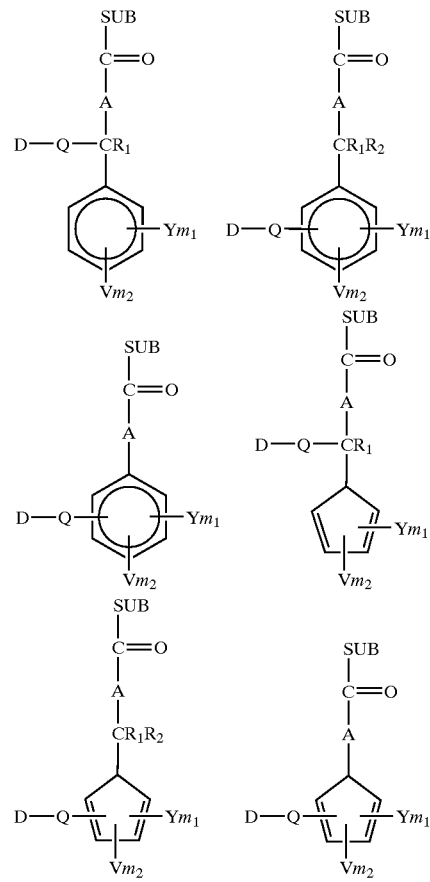

wherein SUB comprises a substrate; $R_1$ and $R_2$ are selected from the group consisting of hydrogen, alkyls, substituted alkyls, aryls, substituted aryls, —CF$_3$, —NO$_2$, —COOH and —COOR, and may be the same or different; A is a divalent functional group selected from the group consisting of —O—, —S— and —NR$_1$; Y comprises one or more polyatomic groups which may be the same or different; V comprises one or more optional monoatomic groups which may be the same or different; Q comprises an optional spacer moiety; m1 and m2 are integers between 1–5 which can be the same or different; and D comprises a detectable moiety which is distinct from R$_1$ and R$_2$.

Another embodiment of the invention is directed to pharmaceutical compositions comprising the conjugate plus a pharmaceutically acceptable carrier such as water, an oil, a lipid, a saccharide, a polysaccharide, glycerol, a collagen or a combination thereof. Pharmaceuticals may be used in the prophylaxis and treatments of diseases and disorders in humans and other mammals.

Another embodiment of the invention is directed to methods for isolating targets from a heterologous mixture. Briefly, a conjugate is created by coupling a bioreactive agent to a substrate by a covalent bond which is selectively cleavable with electromagnetic radiation wherein the bioreactive agent is comprised of a photoreactive moiety bonded to a detectable moiety. The conjugate is contacted to the heterologous mixture to couple substrate to one or more targets. The coupled conjugate is separated from the mixture and treated with electromagnetic radiation to release the substrate, and the targets isolated. This method can be used to isolate targets such as immune system modulators, cytokines, agents of the hematopoietic system, proteins, hormones, gene products, antigens, cells, toxins, bacteria, membrane vesicles, virus particles, and combinations thereof from heterologous mixtures such as biological samples, proteinaceous compositions, nucleic acids, biomass, immortalized cell cultures, primary cell cultures, vesicles, animal models, mammals, cellular and cell membrane extracts, cells in vivo and combinations thereof Another embodiment of the invention is directed to target molecules isolated by the above methods which may be used in pharmaceutical compositions or other compositions and mixtures for industrial applications.

Another embodiment of the invention is directed to methods for isolating targets from a heterologous mixture. A conjugate is created comprising a bioreactive agent coupled to a substrate by a covalent bond which is selectively cleavable with electromagnetic radiation, wherein said bioreactive agent is comprised of a photoreactive moiety bonded to a detectable moiety and the substrate is a precursor of the target. The conjugate is contacted with the heterologous mixture to incorporate substrate into targets. The incorporated conjugate is separated from the mixture, treated with electromagnetic radiation to release the substrate, and the targets isolated. This method is useful for the detection and isolation of nascent proteins, nucleic acids and other biological substances.

Another embodiment of the invention is directed to methods for isolating targets from a heterologous mixture. A conjugate is created which is comprised of a bioreactive agent coupled to a receptor by a covalent bond which is selectively cleavable with electromagnetic radiation, wherein said bioreactive agent is comprised of a photoreactive moiety bonded to a detectable moiety. The conjugate is contacted with the heterologous mixture to couple receptor to targets and the coupled receptor-targets separated from the mixture. The separated conjugate is treated with electromagnetic radiation to release the receptor and the targets isolated.

Another embodiment of the invention is directed to methods for isolating target cells from a heterologous mixture. A conjugate is created comprising a bioreactive agent coupled to a cell receptor by a covalent bond which is selectively cleavable with electromagnetic radiation, wherein the bioreactive agent is comprised of a photoreactive moiety bonded to a detectable moiety. The conjugate is contacted with the heterologous mixture to couple receptor to target cells. The coupled conjugate is separated from the mixture and treated with electromagnetic radiation to release the substrate. Target cells are then easily isolated such as by automation.

Another embodiment of the invention is directed to methods for creating a photocleavable oligonucleotide. A conjugate is created comprising a bioreactive agent coupled to a phosphoramidite which may be a purine-phosphoramidite or a pyrimidine-phosphoramidite. The oligonucleotide is synthesized using photocleavable phosphoramidites. The process can be performed manually or automated to be carried out by an oligonucleotide synthesizer.

Another embodiment of the invention is directed to methods for determining an in vivo half-life of a pharmaceutical in a patient. A conjugate is formed by coupling the pharmaceutical to a bioreactive agent with a covalent bond that can be selectively cleaved with electromagnetic radiation, wherein said bioreactive agent comprises a photoreactive moiety bonded to a detectable moiety. The conjugate is administered to the patient and at least two or more biological samples are removed from the patient at various times after administration of the conjugate. The samples are treated with electromagnetic radiation to release the pharmaceutical from the bioreactive agent and the amount of the bioreactive agent in the biological samples determined. The in vivo half-life of the pharmaceutical can be determined.

Another embodiment of the invention is directed to methods for the controlled release of a substrate into a medium. A conjugate comprised of a bioreactive agent coupled to the substrate by a covalent bond which can be selectively cleaved with electromagnetic radiation is created wherein the bioreactive agent is comprised of a detectable moiety bonded to a photoreactive moiety. The conjugate is bound to a surface of an article which is placed into the medium. The surface of the article is exposed to a measured amount of electromagnetic radiation for the controlled release of the substrate into the medium.

Another embodiment of the invention is directed to methods for detecting a target molecule in a heterologous mixture. A conjugate is formed by coupling a substrate to a bioreactive agent with a covalent bond that is selectively cleavable with electromagnetic radiation, wherein the bioreactive agent is comprised of a detectable moiety bonded to a photoreactive moiety. The conjugate is contacted with the heterologous mixture to couple substrate to one or more target molecules. Uncoupled conjugates are removed and the coupled conjugates are treated with electromagnetic radiation to release the detectable moiety. The released detectable moiety can now be easily detected.

Another embodiment of the invention is directed to methods for detecting a target molecule in a heterologous mixture. A conjugate, comprising a substrate coupled to a bioreactive agent, is formed and contacted with a heterologous mixture to couple a conjugate to one or more target molecules. Uncoupled conjugates are removed and the coupled conjugates are treated with electromagnetic radiation to release substrate. Released substrate is detected and can be further isolated.

Another embodiment of the invention is directed to methods for the isolation of a PCR product. A bioreactive agent is conjugated to one or more oligonucleotide primers with a covalent bond that is selectively cleavable with electromagnetic radiation, wherein the bioreactive agent is comprised of a detectable moiety bonded to a photoreactive moiety. A nucleic acid sequence is PCR amplified with the conjugated primers. The amplified sequences are isolated and subsequently treated with electromagnetic radiation to release the bioreactive agent.

Another embodiment of the invention is directed to methods for treating a disorder by the controlled release of a therapeutic agent at a selected site. A conjugate is formed by bonding a bioreactive agent to the therapeutic agent with a bond that is selectively cleavable with electromagnetic radiation, wherein the bioreactive agent is comprised of a directable moiety bonded to a photoreactive moiety wherein the directable moiety has an affinity for the selected site. The conjugate is administered to a patient having the disorder. The selected site is subjected to a measured amount of electromagnetic radiation for the controlled release of the therapeutic agent to treat the disorder.

Another embodiment of the invention is directed to kits for detecting a disorder in biological samples containing conjugates comprised of a bioreactive agent covalently bonded to a diagnostic agent having an affinity for an indicator of the disorder in the biological sample, wherein the covalent bond is selectively cleavable with electromagnetic radiation.

Another embodiment of the invention is directed to kits comprising a bioreactive agent covalently bonded to an oligonucleotide. The photocleavable oligonucleotide may be double-stranded or single-stranded and may possess restriction enzyme recognition sites useful in cloning and other procedures in molecular biology.

Other embodiments and advantages of the invention are set forth, in part, in the description which follows and, in part, will be obvious from this description or may be learned from the practice of the invention.

DESCRIPTION OF THE INVENTION

Figure 1:
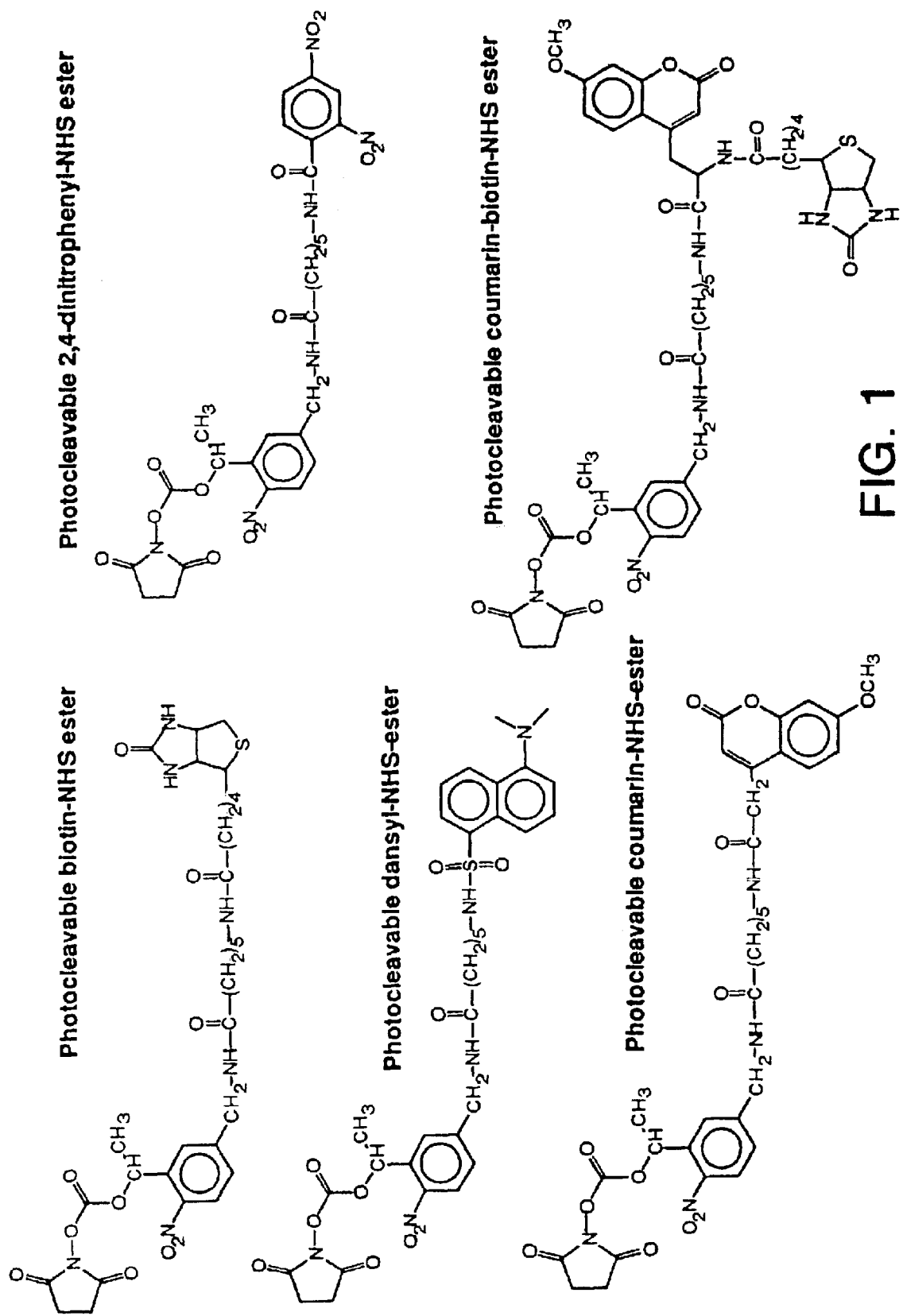
FIG. 1 Examples of photocleavable agents.

As embodied and broadly described herein, the present invention is directed to agents and conjugates used in the detection and isolation of targets such as chemicals, macromolecules, cells and any identifiable substance from a mixture. Agents comprise a detectable moiety bound to a photoreactive moiety. Conjugates comprise agents which are coupled to substrates by one or more covalent bonds which, by the presence of the photoreactive moiety, are selectively cleavable with electromagnetic radiation. The invention is also directed to methods for the isolation and detection of targets using these agents and conjugates, to kits which utilize these methods for the detection of diseases and disorders in patients, and to methods for the detection and isolation of nearly any substance from a heterologous mixture.

There are many methods currently available for the detection and isolation of a desired substance or target from a complex mixture. Most of these methods require the specific labeling of the substance or target to be detected, detection of that label and subsequent removal of label from target. Although straightforward, current detection and isolation methodologies possess a number of problems. For example, it is often difficult to specifically attach target with label. Affinity of label for target may be low, suitable points of attachment may not be available on specific substances and the label and the target may simply be chemically or physically incompatible. In addition, label may hinder or completely destroy the functional activity of the target frustrating the purpose of isolation. Isolated targets are unavoidably contaminated or inactivated due to the presence of a toxic or damaging label. A typical example of this sort of problem is the isolation of cells bound with biotin after selection by coupling to streptavidin. The powerful affinity of biotin for streptavidin makes the isolation procedure relatively straightforward and specific, however, the isolated cells are often dead and dying due to the toxic effects of the coupling agents or the harsh isolation procedures. This is also true when attempting to isolate active proteins from biological samples and other complex mixtures for later use. The presence of label may denature or render the protein product inactive or simply unacceptable for in vivo use under current FDA standards and guidelines. Removal of the agent sometimes overcomes these problems, however, methods to separate and remove label from target are generally rather harsh, take a significant amount of time, effort and expense, and, for the most part, result in fairly low yields of the final product. Viability and functional activity of the target is often severely impaired and is often destroyed.

The invention overcomes these problems by providing detectable, bioreactive agents which can detect and isolate targets. Agents of the invention comprise a detectable moiety and a photoreactive moiety, and can be covalently coupled to a variety of target substrates. A covalent bond between agent and substrate can be created from a wide variety of chemical moieties including amines, hydroxyls, imidazoles, aldehydes, carboxylic acids, esters and thiols. Agent-substrate combinations are referred to herein as conjugates. Through the presence of the detectable moiety, conjugates can be quickly and accurately detected and target isolated. Further, these conjugates are selectively cleavable which provides unique advantages in isolation procedures. Substrate can be separated from agent quickly and efficiently. Complex technical procedures and highly trained experts are not required. New attachment and separation procedures do not need to be developed for every new target to be isolated. Following isolation, it is a relatively simple matter to treat the conjugate with electromagnetic radiation and release the substrate. Released substrate is preferably functionally active and structurally unaltered. Nevertheless, minor chemical alterations in the structure may occur depending on the point of attachment. It is generally preferred that such alterations not effect functional activity. However, when functional activity does not need to be preserved, such changes are of no considerations and may even be useful to identify and distinguish targets isolated by methods of the invention.

Targets, as referred to herein, are those substances being identified, characterized or isolated using the agents, conjugates and methods of the invention. Substrates, as referred to herein, are those substances which are covalently attached to the bioreactive agent. Substrates may also be referred to as targets when the target being identified specifically binds to the bioreactive agent.

One embodiment of the invention is directed to a bioreactive agent comprising a detectable moiety bonded to a photoreactive moiety wherein the photoreactive moiety contains at least one group capable of covalently bonding to a substrate to form a conjugate. The resulting conjugate can be selectively cleaved to release said substrate or, alternatively, to release any chemical group or agent of the conjugate. Cleavage, as referred to herein, is by photocleavage or a cleavage event triggered by the application of radiation to the conjugate. The radiation applied may comprise one or more wavelengths from the electromagnetic spectrum including x-rays (about 0.1 nm to about 10.0 nm; or about $10^{18}$ to about $10^{16}$ Hz), ultraviolet (UV) rays (about 10.0 nm to about 380 nm; or about $8\times10^{16}$ to about $10^{15}$ Hz), visible light (about 380 nm to about 750 nm; or about $8\times10^{14}$ to about $4\times10^{14}$ Hz), infrared light (about 750 nm to about 0.1 cm; or about $4\times10^{14}$ to about $5\times10^{11}$ Hz), microwaves (about 0.1 cm to about 100 cm; or about $10^{8}$ to about $5\times10^{11}$ Hz), and radio waves (about 100 cm to about $10^{4}$ m; or about $10^{4}$ to about $10^{8}$ Hz). Multiple forms of radiation may also be applied simultaneously, in combination or coordinated in a step-wise fashion. Radiation exposure may be constant over a period of seconds, minutes or hours, or varied with pulses at predetermined intervals.

Typically, the radiation source is placed at a specified distance from the conjugate to be irradiated. That distance may be empirically determined or calculated from the energy loss produced between the source and the target and the amount of energy emitted by the source. Conjugate may be in solution or attached to a solid support which may be a type of glass, ceramic, polymer or semiconductor surfaces. Typical solid supports are nitrocellulose membranes, agarose beads, magnetic beads coated with streptavidin, semiconductor surfaces and resins. Preferably, the radiation applied is UV, visible or IR radiation of the wavelength between about 200 nm to about 1,000 nm, more preferably between about 260 nm to about 600 nm, and more preferably between about 300 nm to about 500 nm. Radiation is administered continuously or as pulses for hours, minutes or seconds, and preferably for the shortest amount of time possible to minimize any risk of damage to the substrate and for convenience. Radiation may be administered for less than about one hour, preferably less for than about 30 minutes, more preferably for less than about ten minutes, and still more preferably for less than about one minute. Visible, UV and IR radiation are also preferred as all three of these forms of radiation can be conveniently and inexpensively generated from commercially available sources.

The power density or intensity of light per area necessary to selectively cleave the covalent bond is very small which makes the photocleavable process practical. Maximization of efficiency also minimizes exposure time necessary to achieve selective cleavage and provide a minimum of undesirable background effects.

One part of the bioreactive agent is the detectable moiety. The detectable moiety is a chemical group, structure or compound that possesses a specifically identifiable physical property which can be distinguished from the physical properties of other chemicals present in the heterologous mixture. Fluorescence, phosphorescence and luminescence including electroluminescence, chemiluminescence and bioluminescence are all detectable physical properties not found in most substances, but known to occur or to be inducible in others. For example, reactive derivatives of dansyl, coumarins, rhodamine and fluorescein are all inherently fluorescent when excited with light of a specific wavelength and can be specifically bound or attached to other substances. Coumarin has a high fluorescent quantum yield, higher than even a dansyl moiety, and facilitates detection where very low levels of target that are being sought. Coumarin is structurally similar to tryptophan, which can be useful in for example in the translation of nascent proteins with non-native amino acids. It may also be useful to combine certain detectable moieties to facilitate detection or isolation. Preferably the detectable moiety is a fluorescent compound and the preferred fluorescent compounds are listed in Table 3, all of which are commercially available (Sigma Chemical; St. Louis, Mo.).

TABLE 3

Fluorescent Labeling Compounds 4-acetamido-4'-isothiocyanatostilbene-2-2'-disulfonic acid
7-amino-4-methylcoumarin (AMC)
7-amino-4-trifluoromethylcoumarin
N-(4-anilino-1-naphthyl) maleimide
4',6-diamidino-2-phenylindole (DAPI)
5-(4,6-dichlorotriazin-2-yl) aminofluorescein (DTAF)
4,4'-diisothiocyanatostilbene-2,2'-disulfonic acid
tetramethylrhodamine isothiocyanate (TRITC)
quinolizino fluorescein isothiocyanate (QFITC)

| dansyl chloride | eosin isothiocyanate |
|---|---|
| erythrosin B | fluorescamine |
| fluorescene | fluorescein derivatives |
| 4-methylumbelliferone | o-phthaldialdehyde |
| rhodamine B | rhodamine B derivatives |
| rhodamine 6G | rhodamine 123 |
| sulforhodamine B | sulforhodamine 101 | sulforhodamine 101 acid chloride

Luminescence can also be induced in certain chemicals referred to as luciferins. Energetic molecules such as ATP supply chemical energy for catalytic activities of luciferase enzymes causing the luciferins to emit light. Reagents for both the bacterial luciferase system (*Vibrio harveyi* or *V. fischeri*) and the firefly luciferase system (*Photinus pyralis*) are available from a variety of commercial sources (e.g. Sigma Chem. Co; St. Louis, Mo.).

Preferably, the luminescent agent has a high quantum yield of fluorescence at a wavelength of excitation different from that used to perform the photocleavage. Upon excitation at such wavelengths, the agent is detectable at low concentrations either visually or using conventional luminescence detectors and fluorescence spectrometers. Electroluminescence, produced by agents such as ruthenium chelates and their derivatives, or agents that possess nitroxide moieties and similar derivatives are preferred when extreme sensitivity is desired (J. DiCesare et al., BioTechniques 15:152–59, 1993). These agents are detectable at the femtomolar ranges and below.

Application of an electric field will also induce a detectable response in certain chemicals' due to a net electric charge which induces the substance to migrate in an electric field. Magnetism may also be a detectable property if a magnetized substance such as iron or another magnetized metal is or is associated with the detectable moiety.

Other forms of detectable physical properties include an identifiable electrical polarizability, electron spin resonance and Raman scattering. Agents may also undergo a chemical, biochemical, enzymatic, electrochemical or photochemical reaction such as a color change in response to external electromagnetic fields or the introduction of other substances. Such electromagnetic fields and substances may be a catalyst or another reactant molecule that allows for detection of the bioreactive agent or transforms the agent into a detectable moiety.

All of these labeling agents can be specifically detected using the appropriate detector or detection system such as a spectrometer or electrophoretic or chromatographic systems. At times, it may be preferable to have a visually discernable detection system such as one that will trigger a photoelectric cell or one that can be detected and recorded manually. Spectrometers including absorption and fluorescence spectrometers are very sensitive detectors of specific energy of absorptions or emissions from many detectable moieties. Detection and sorting of target may be automated as in the case of fluorescence activated cell sorters (FACS) which detect and isolate cells that possess a fluorescent label. Targets may be detected and sorted manually as can be done quite simply with magnetized conjugates using a magnet.

Additional physical properties which can be easily and accurately detected include chromaticism (e.g. violet=about 400–430 nm, blue=about 450–500 nm, green=about 550 nm, yellow=about 600 nm, orange=about 650 nm, red=about 700–750 nm), electromagnetic absorbance, enzyme activity or the ability to specifically bind with a coupling agent. Useful coupling agents include biotin, avidin, streptavidin, nucleic acids, nucleic acid and lipid binding proteins, haptens, antibodies, receptors, carbohydrates, immunogenic molecules, and derivatives and combinations thereof. The detectable moiety may have a combination of these properties allowing its selection from a wide variety of background materials. Some examples of the chemical structures of photocleavable agents of the invention are depicted in FIG. 1.

Another preferred detectable moiety is a coupling agent and the preferred coupling agent is biotin or a biotin derivative. Biotin-containing bioreactive agents are referred to herein as photocleavable biotins or PCBs. The binding between the egg-white protein avidin, a tetrameric protein found in avian eggs with the water soluble vitamin, biotin, is one of the strongest interactions known in biology having an association constant ($K_a$) of about $10^{15} M^{-1}$, exceeding that of antibody-antigen interactions (M. Wilchek and E. A. Bayer, Methods Enzymol. 184, 1990). The bacterial counterpart to avidin is streptavidin, found in *Streptomyces avidinii*, which is slightly more specific for biotin than avidin. This strong interaction, along with the ability to covalently link biotin to a variety of substrates including proteins, nucleic acids, lipids, and receptor ligands such as neuropeptides and hormones, has resulted in a vast array of uses for these coupling agents all of which can be improved or enhanced with the use of PCB.

Figure 2:
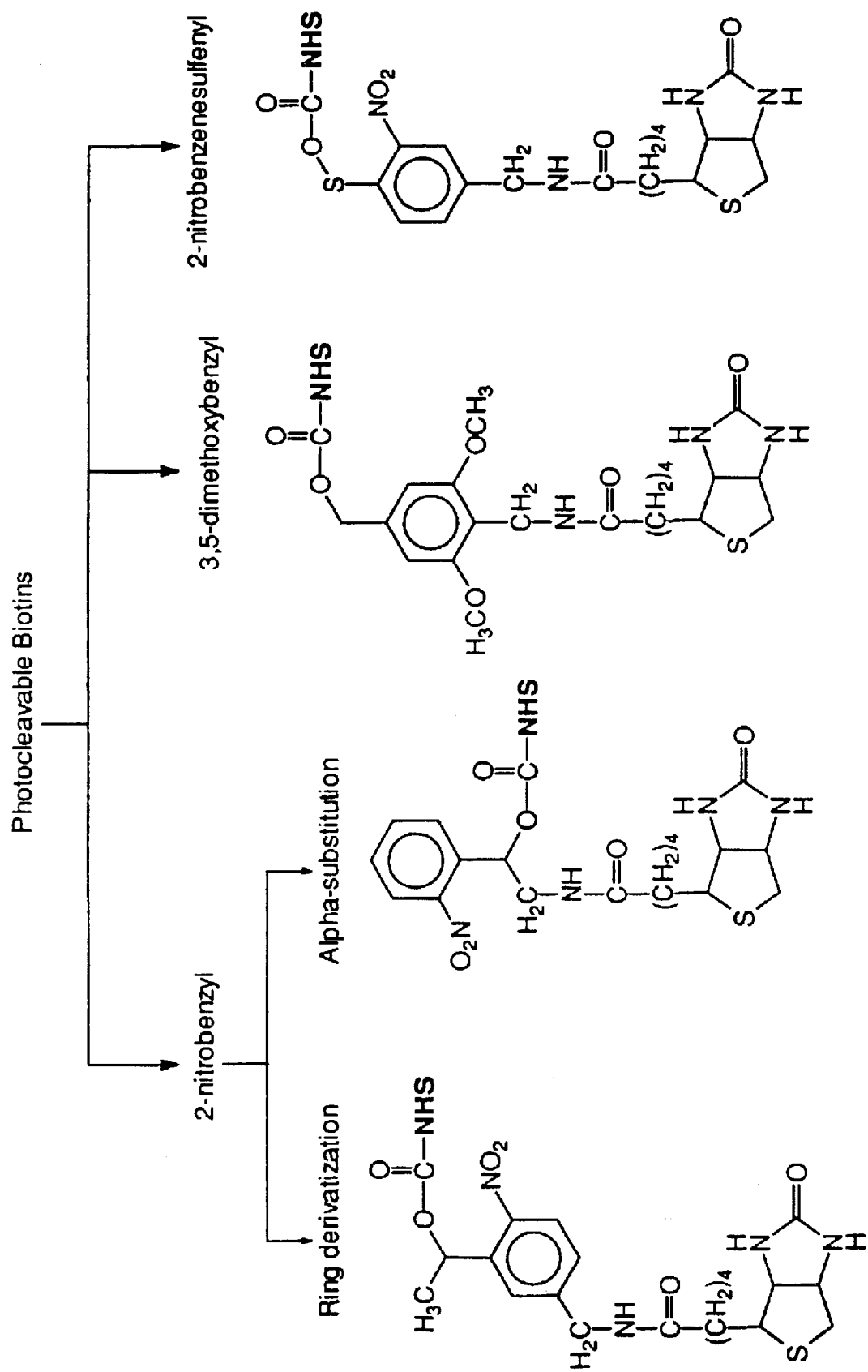
FIG. 2 Photocleavable biotins with various photoreactive moieties.

A wide variety of biotinyl moieties can be used to form a PCB molecule. Biotin ($C_{10}H_{16}N_2O_3S$) has a molecular weight of 244.31 daltons and is comprised of a ring linked to an alkyl chain terminated by a carboxyl group. Numerous modifications can be made to the biotin moiety which involve changes in the ring, spacer arm and terminating group, all of which still exhibit a high affinity for streptavidin, avidin and their derivatives. Examples of photocleavable biotins that can be designed based on various photoreactive moieties are depicted in FIG. 2.

The detection and isolation of chemical, biochemical and biological materials using the interaction between biotin and streptavidin is normally based on the immobilization of avidin or streptavidin to a surface (e.g. membranes, gels, filters, microtiter wells, magnetic beads). To that surface is applied a solution containing biotin coupled to targets which then bind to the streptavidin-coated surface. Biotin-containing target molecules can be isolated and non-biotinylated components washed away. Alternatively, biotinylated target molecules can be separated from a heterogeneous mixture using streptavidin-containing affinity columns. Biotinylated macromolecules including nucleic acids (DNA or RNA), proteins and protein-containing complexes, and even cells whose surface has been biotinylated or bound to a biotinylated antibody can be detected and isolated with these techniques.

As stated, biotin can be coupled to a wide variety of molecules including proteins, carbohydrates and nucleic acids. The availability of biotin derivatives has expanded this range even further. For example, biotin derivatives have been prepared with functionalities which are reactive towards amines, phenols, imidazoles, aldehydes, carboxylic acids and thiols. Biotin can also be incorporated into proteins, DNA and RNA by first attaching the biotin to building blocks of macromolecules such as amino acid or nucleotides which can be directly attached to these molecules or incorporated during their synthesis by chemical or enzymatic means.

Unlike conventional biotins, photocleavable biotins enable one to release or elute the bound substrate from the immobilized avidin, streptavidin or their derivatives in a completely unmodified form. This is extremely useful and an important improvement over existing biotins for a number of reasons. Biotinylation of the target material can impede its subsequent use or characterization. Biotinylation of a protein can alter its activity, electrophoretic mobility, ability to bind a substrate, antigenicity, ability to reconstitute into a native form and ability to form multisubunit complexes. In contrast, using photocleavable biotin, once the biotin is photocleaved from the protein or protein/binding complex, all the native properties and function will be restored to its native form for further use and characterization. Listed in Table 4 are some of the substrates to which a photocleavable agent such as PCB can be linked.

TABLE 4

Chemical linkage of Photocleavable Biotins with different molecules

| Molecule or Assemblage | Functional Group on the Molecule | Reactive moiety on the PCB | Resulting linkage and reaction conditions |
|---|---|---|---|
| Amino acids, proteins, enzymes or antibodies | Amino group or R—NH$_2$ | NHS-ester | Amide linkage |
| Amino acids, proteins, enzymes or antibodies | R—OH | chloroformate carboxylic acid | Ester linkage |
| Amino acids, proteins, enzymes or antibodies | R—COOH | Reaction with parent alcohol (DCC coupling) | Ester linkage |

TABLE 4-continued

Chemical linkage of Photocleavable Biotins with different molecules

| Molecule or Assemblage | Functional Group on the Molecule | Reactive moiety on the PCB | Resulting linkage and reaction conditions |
| --- | --- | --- | --- |
| Nucleotides, RNA or DNA molecules | Aromatic amines | chloroformate | Amides |
| Carbohydrates RNA for ribonucleotides | Sugar hydroxy R—OH | chloroformate | Ester linkage |
| Nucleotide phosphoramidites | Phosphate groups | diazoethane | Phosphate ester |
| Lipids/ Phosphatidyl serine | R—NH$_2$ | Chloroformate NHS-ester | amide |
| Carbohydrates | Sugar hydroxyl | Chloroformate | Ester linkage |

There are a number of chemical moieties available in bioreactive agents and conjugates of the invention. For example, an NHS-ester functionality introduced in PCB is highly reactive and can selectively react with aliphatic amino groups that are present in proteins. Another example is a phosphoramidite moiety which is highly reactive and can selectively react with hydroxyl groups of nucleic acids. In cases where chemical moieties like carboxyl (—COOH) or phosphate groups need modification, a precursor of PCB in the form of the parent alcohol can be used to form appropriate ester-type linkages. These derivatives can be chemically linked to a variety of macromolecules and molecular components including amino acids, nucleotides, proteins and polypeptides, nucleic acids (DNA, RNA, PNA), lipids, hormones and molecules which function as ligands for receptors.

The application of biotin-avidin technology for the detection and isolation of chemical and biological materials has also been broadened by the use of binding molecules which are first biotinylated and then allowed to selectively interact with the target molecule to be isolated. Isolation of the target molecule or cell is facilitated by the binding of the biotinylated binding-complex to the streptavidin-containing column or streptavidin-coated magnetic beads. Binding molecules include antibodies which selectively bind to specific antigens, DNA probes which selectively bind to specific DNA sequences and ligands which selectively bind to specific receptors. This approach has been used to isolate a wide variety of macromolecules and cells (Tables 2 and 3). However, such isolation methods require that the biotinylated target be released from the bound streptavidin. Disruption of this bond typically requires non-physiological conditions such as low pH and high concentration of guanidinium-HCl which is usually damaging for the target molecule or cell. Even after disruption of the streptavidin-biotin interaction, the target or binding molecule remains partially or completely biotinylated which can interfere with later uses. Further, elution conditions are non-physiological and can also be disruptive to the target molecule or cell. In contrast, using photocleavable biotins substrate can be quickly and easily cleaved from biotin with little to no effect on substrate conformation or activity.

The use of PCB in any of the usual detection and purification procedures, including those discussed above, represents a significant savings of time, energy and ultimately cost. In addition, a variety of derivatives of avidin and streptavidin are commercially available which have been modified through chemical or genetic means. These same derivatives can be used with PCB. One example is ImmunoPure NeutrAvidin sold commercially (Pierce Chemical; Rockford, Ill). This protein is a modified avidin derivative which has been deglycosylated and does not contain the RYD domain that serves as a universal recognition sequence for many cell receptors. Non-specific adsorption to other proteins and cell surfaces is greatly reduced.

Figure 3:
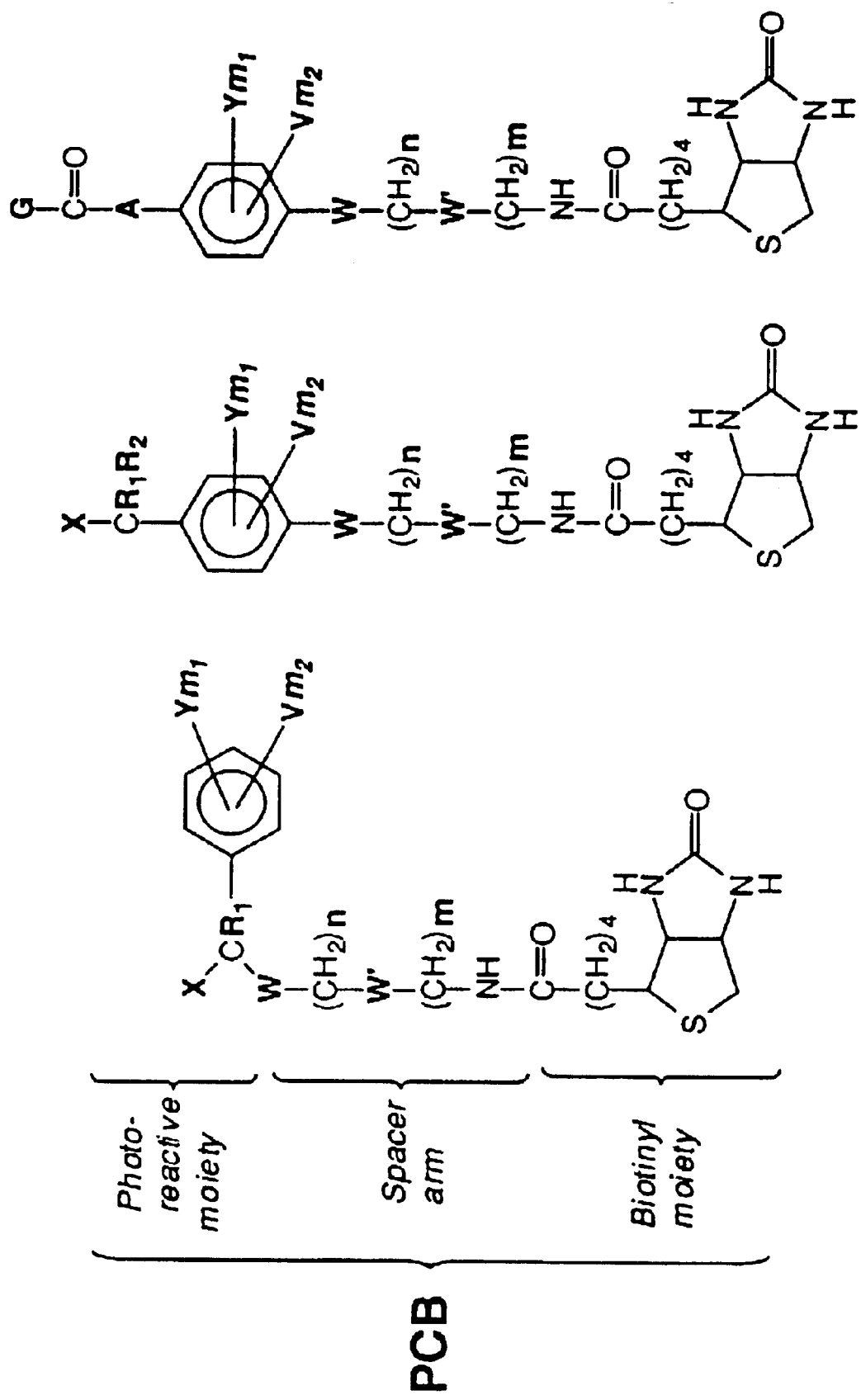
FIG. 3 Schematic representation of photocleavable biotin

The major molecular elements of a photocleavable biotin (PCB) are a photoreactive moiety and a biotinyl moiety which constitutes the detectable moiety (FIG. 3). The photoreactive moiety and the biotinyl moiety are linked together with a spacer arm to form the PCB molecule. The photoreactive moiety contains a five or six membered ring derivatized with functionalities represented by X, Y and A-C(O)-G, wherein X allows linkage of PCB to the biomolecular substrate. In the preferred embodiment, Y represents a substitution pattern on a phenyl ring containing one or more substituents such as nitro or alkoxy groups. The functionality W represents the group that allows linkage of the cross-linker moiety to the photoreactive moiety. The purpose of the spacer arm is to increase the access of the biotin moiety for effective interaction with streptavidin, and thus, increase the binding efficiency. Typically these can be constructed using either long alkyl chains or using multiple repeat units of caproyl moieties linked via amide linkages.

Choice of photolabile group, spacer arm and the biotinyl moiety depends on the target substrate including amino acids, proteins, antibodies, nucleotides, DNA or RNA, lipids, carbohydrates and cells to which the photocleavable biotin is. to be attached. It also depends on the exact conditions for photocleavage and the desired interaction between the biotinyl moiety and streptavidin, avidin or their derivatives. Some of the various choices for the photolabile group and linker arms for PCB are shown in FIG. 2.

Additional types of coupling agents include antibodies, antibody fragments and antigens. Antibodies have the advantage that they can bind to their respective antigen with great specificity. Substrates which are antigens can be detected by their ability to specifically bind to available antibodies or to antibodies which can be easily created. Useful antibodies or antibody fragments may be monoclonal or polyclonal and are preferable of the class IgG, but may also be IgM, IgA, IgD or IgE. Other preferred detectable moieties include nucleic acids. Short sequences of RNA or DNA or oligonucleotides, preferably less than about thirty nucleotides in length and as short as four to ten nucleotides, can be detected by their ability to specifically hybridize with a complementary nucleic acid and detected directly or indirectly using PCR which greatly amplifies a specific sequence that is subsequently detected. In a similar fashion, binding proteins and receptor-ligand combinations are also useful as detectable labels.

The second component of the bioreactive agent is the photoreactive moiety. The photoreactive moiety is a chemical moiety capable of forming one or more covalent bonds with a substrate which can be cleaved with electromagnetic radiation. These bonds may be formed with a chemical group on the substrate such as, for example, an amine, phenol, imidazole, aldehyde, carboxylic acid or thiol. The photoreactive agent is a substituted aromatic ring containing at least one polyatomic group and, optionally, one or more monoatomic groups. The aromatic ring is preferably a five or six-membered ring. The substitutions comprise the polyatomic and optional monoatomic groups. The polyatomic group imparts electron channeling properties to attract or repel electrons to certain locations within the chemical structure, thereby creating or establishing the conditions to create the selectively cleavable covalent bonds. Some monoatomic groups such as halides can adjust the frequency or wavelength of the electromagnetic radiation which will induce cleavage. As such, monoatomic groups fine tune the cleavage event to sensitize conjugates to predetermined frequencies or intensities of radiation.

Figure 4:
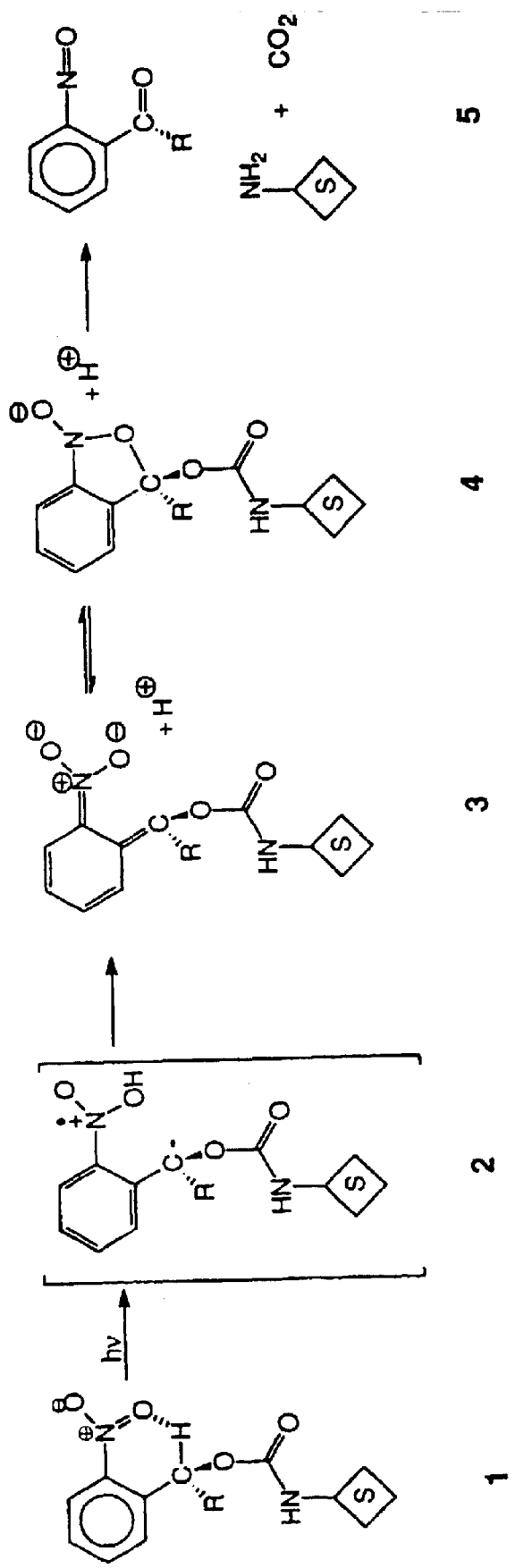
FIG. 4 Mechanism of photocleavage in 2-nitrobenzyl-based systems.

One class of photoreactive moieties are 2-nitrobenzyl derivatives. In their ground state, 2-nitrobenzyl-based agents and conjugates have an intramolecular hydrogen bond between benzylic hydrogen and the ortho nitro group (—CH—O$_2$N) (B. Brzezinski et al., J. Chem. Soc. Perkin. Trans. 2:2257–61, 1992). Upon illumination with wavelengths of greater than 300 nm, these chemical compounds transition to an excited state. Proton transfer reaction from benzylic carbon to the oxygen in nitro group takes place which is followed by electron rearrangement (FIG. 4). This reaction results in the formation of a transient species called an aci-nitro ion which is in a rapid equilibrium with a cyclic form. In the cyclic intermediate, electron rearrangement and oxygen transfer from nitrogen to benzylic carbon takes place resulting in the formation of 2-nitroso derivatives and release of a substrate which is a good leaving group (J. A. McCray et al., Annu. Rev. Biophys. Chem. 18:239–70, 1989).

Figure 5:
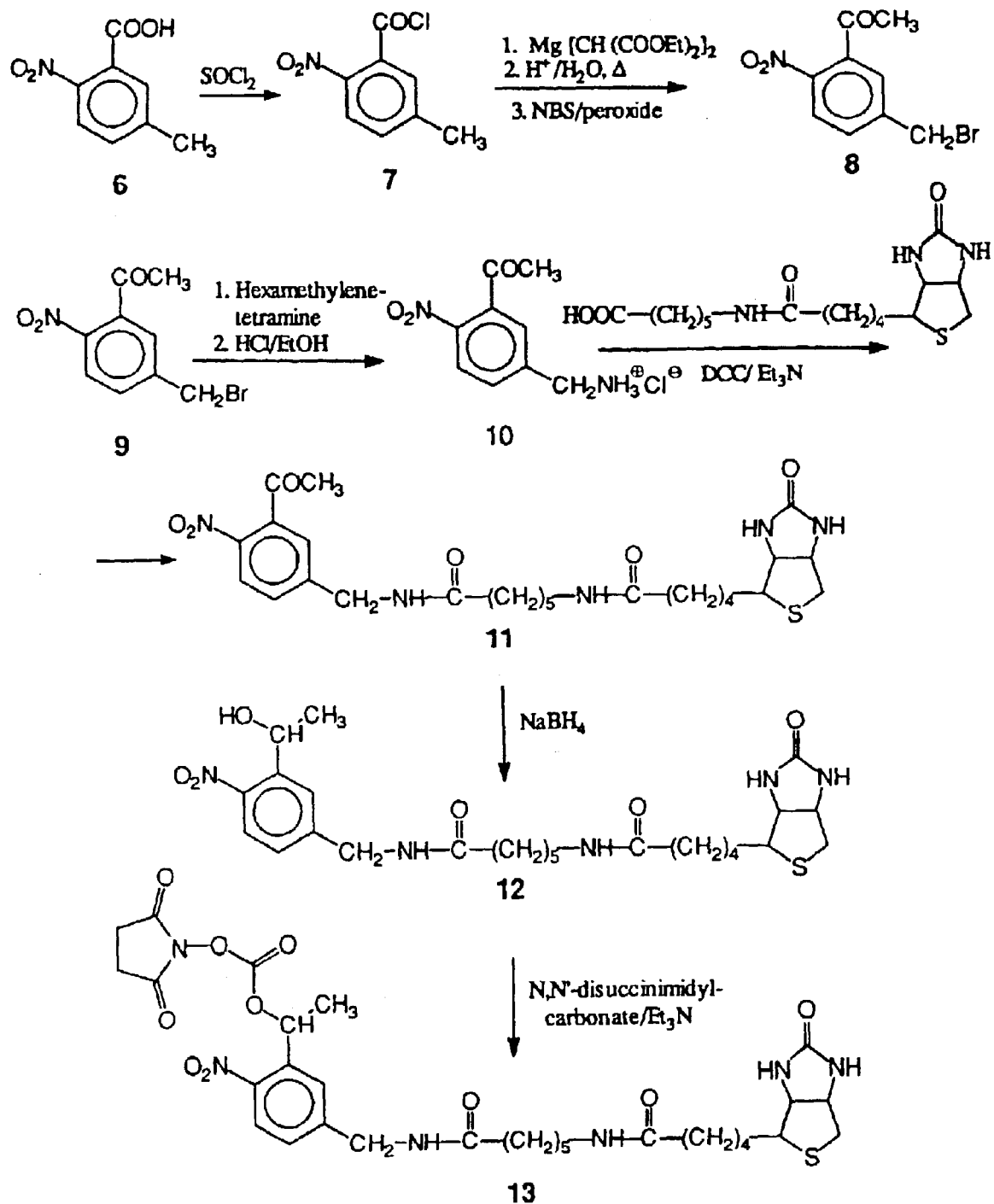
FIG. 5 Synthesis of photocleavable biotin.

Chemical synthesis of PCB NHS-ester involves three principal steps: (1) Generation of the photoreactive moiety, for example, 5-methyl-2-nitroacetophenone. (2) Generation of a suitable amino group and attachment to biotin containing spacer. (3) Generation of hydroxyl groups and derivatization as N-hydroxysuccinimidyl carbonate (NHS-ester). These steps are schematically represented in FIG. 5.

Bioreactive agents can also be synthesized based on other photoreactive moieties. Chemical syntheses of two other classes of photocleavable moieties 3,5-dimethoxybenzyl and 2-nitrobenzenesulfenyl (FIG. 2) can be carried out using similar synthesis strategies. These 2-nitrobenzyl groups all contain a benzylic carbon-hydrogen bond ortho to a nitro group, which is necessary for their photolability. In the developments of these photolabile groups as protecting groups, difficulties were encountered as the subsequent reactions of these carbonyl compounds resulted in formation of coupled azo compounds, which act as internal light filters (V. N. R. Pillai, Synthesis 1, 1980). These complications were overcome in the present invention with the use of α-substituted, o-nitrobenzyl compounds. Bioreactive agents of the invention that form a detectable photocleavable conjugate can, for example, be represented by the formula: wherein X is selected from the group consisting of a halogen, N$_2$, CH$_2$-halogen, —N=C=O, —N=C=S, —S—S—R, NC$_2$H$_4$, —NC$_4$H$_2$O$_2$, —OH, —NHNH$_2$, —OP (OR$_3$)N(R$_4$)R$_5$ and —OCO-G wherein G is selected from the group consisting of a halogen, N$_3$, O-esters and N-amides; R$_1$, R$_2$, R$_3$, R$_4$ and R$_5$ are selected from the group consisting of hydrogen, alkyls, substituted alkyls, aryls and substituted aryls, —CF$_3$, —NO$_2$, —COOH and —COOR, and may be the same or different; A is a divalent functional group selected from the group consisting of —O—, —S— and —NR$_1$; Y comprises one or more polyatomic groups which may be the same or different; V comprises one or more optional monoatomic groups which may be the same or different; Q comprises an optional spacer moiety; m1 and m2 are integers from 0–5 and may be the same or different; and D comprises a selectively detectable moiety which is distinct from R$_1$–R$_5$. The O-ester may be cyanomethyl, o and p nitrophenyl, 2,4-dinitrophenyl, 2,4,5-trichlorophenyl, pentachlorophenyl, pentafluorophenyl, N-hydroxyphthalimidyl, N-hydroxysuccinimidyl, 1-hydroxypiperidinyl, 5-chloro-8-hydroxy-quinolyl, 1-hydroxybenzotriazolyl, 3,4-dihydro-4-oxobenzotriazin-3-yl (DHBT), 2,3-dihydro-2,5-diphenyl-3-oxo-thiophen-1,1-dioxide-4-yl (TDO), 1,2-benzisoxasolyl, 2-hydroxypyridyl or derivatives or combinations thereof. The N-amide is an imidazolyl, benzimidazolyl, benzisoxazolyl, 3,5-dioxo-4-methyl-1,2,4-oxadiezolidinyl or derivatives or combinations thereof.

Polyatomic groups can be attached to the aromatic ring include nitro groups (—NO$_2$), sulfoxide groups such as (—SO$_3$), alkyl groups such as methyl (—CH$_3$) and ethyl groups (—CH$_2$CH$_3$), alkoxyl groups such as (—OCH$_3$), and derivatives and combinations thereof. Useful monoatomic groups are halides such as chloride (—Cl), fluoride (—F), iodide (—I), bromide (—Br), and hydrogen (—H). These groups may be placed in any of the available positions around the ring. Selection and placement of the polyatomic and monoatomic groups may influence the wavelength of electromagnetic radiation required to induce cleavage and the period of time that radiation must be applied to induce efficient cleavage. The chemical moieties at R$_1$, R$_2$, R$_3$, R$_4$ and/or R$_5$ may also influence the photoreaction.

Figure 6:
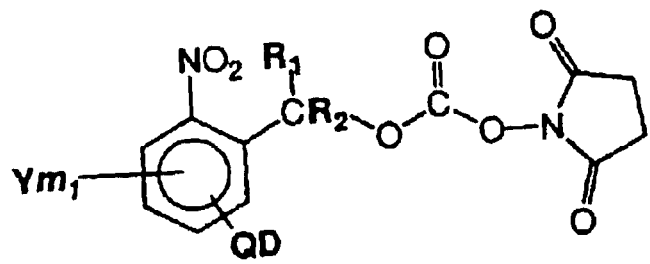
FIG. 6 Chemical variations of photocleavable agents.
Figure 6:
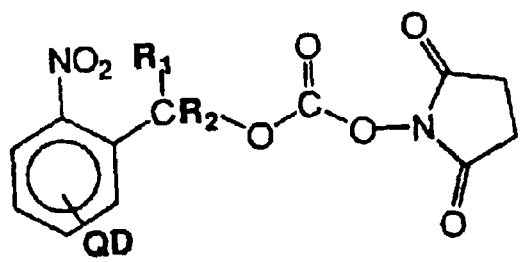
Figure 6:
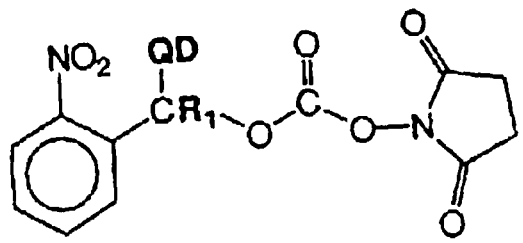
Figure 6:
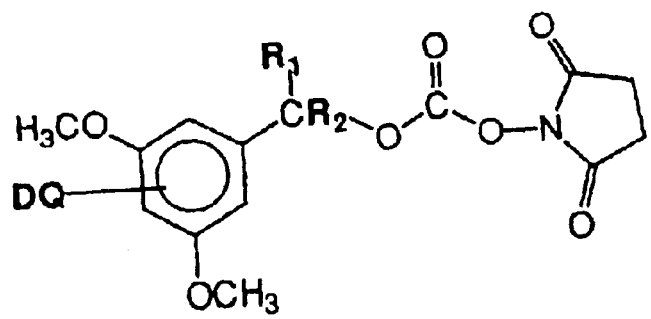
Figure 6:
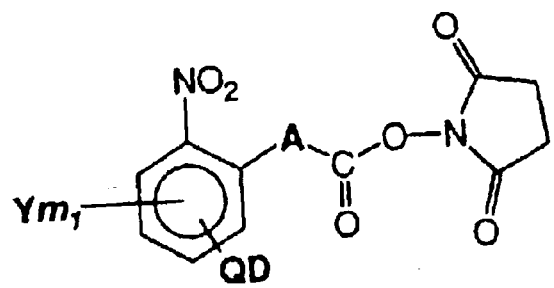

It is sometimes useful to include in the agent a spacer moiety bonded between the photoreactive moiety and the detectable moiety. The presence of the spacer can be advantageous sterically for substrate binding. The spacer moiety (Q) may comprise a branched or straight chain hydrocarbon, a polymeric carbohydrate, or a derivative or combination thereof. The preferred spacer moiety is represented by the formula:

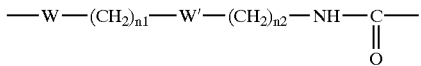

wherein W and W' are each selected from the group consisting of —C(O)—, —C(O)—NH—, —HN—C(O)—, —NH—, —O—, —S— and —CH$_2$—, and may be the same or different; and n1 and n2 are integers from 0–10 which can be the same or different and if either n1 or n2 is zero, then W and W' are optional. Examples of the chemical structure of bioreactive agents are depicted in FIG. 6.

Another embodiment of the invention is directed to photocleavable conjugates comprising bioreactive agents photocleavably coupled to substrates. Conjugates have the property that they can be selectively cleaved with electromagnetic radiation to release the substrate. Substrates are those chemicals, macromolecules, cells and other substances which are or can be used to detect and isolate targets. Substrates that are selectively cleaved from conjugates may be modified by photocleavage, but still functionally active, or may be released from the conjugate completely unmodified by photocleavage. Substrates may be coupled with agents, uncoupled and recoupled to new agents at will.

Useful substrates are any chemical, macromolecule or cell that can be attached to a bioreactive agent. Examples of useful substrates include proteins, peptides, amino adds, amino acid analogs, nucleic acids, nucleosides, nucleotides, lipids, vesicles, detergent micells, cells, virus particles, fatty acids, saccharides, polysaccharides, inorganic molecules and metals. Substrates may also comprise derivatives and combinations of these substances such as fusion proteins, protein-carbohydrate complexes and organo-metallic compounds. Substrates may also be pharmaceutical agents such as cytokines, immune system modulators, agents of the hematopoietic system, recombinant proteins, chemotherapeutic agents, radio-isotopes, antigens, anti-neoplastic agents, enzymes, PCR products, receptors, hormones, vaccines, haptens, toxins, antibiotics, nascent proteins, synthetic pharmaceuticals and derivatives and combinations thereof.

Substrates may be targets or part of the targets such as an amino acid in the synthesis of nascent polypeptide chains wherein substrates may be amino acid or amino acid derivative which becomes incorporated into the growing peptide chain. Substrates may also be nucleotides or nucleotide derivatives as precursors in the synthesis of a nucleic acid. Constructs useful in creating synthetic oligonucleotide conjugates may contain phosphoramidites or derivatives of DATP, dCTP, dTTP and dGTP, and also ATP, CTP, UTP and GTP. Resulting nucleic acid-conjugates can be used in PCR technologies, antisense therapy, and prophylactic and diagnostic applications. Substrates may be targets, for example, when it is possible to specifically react the bioreactive agent with substrate in a mixture such that the reaction creates the conjugate. Such conjugates are useful when it is desirable to follow a target through a biological or other type of system such as when determining the half-life of a pharmaceutical.

Figure 7:
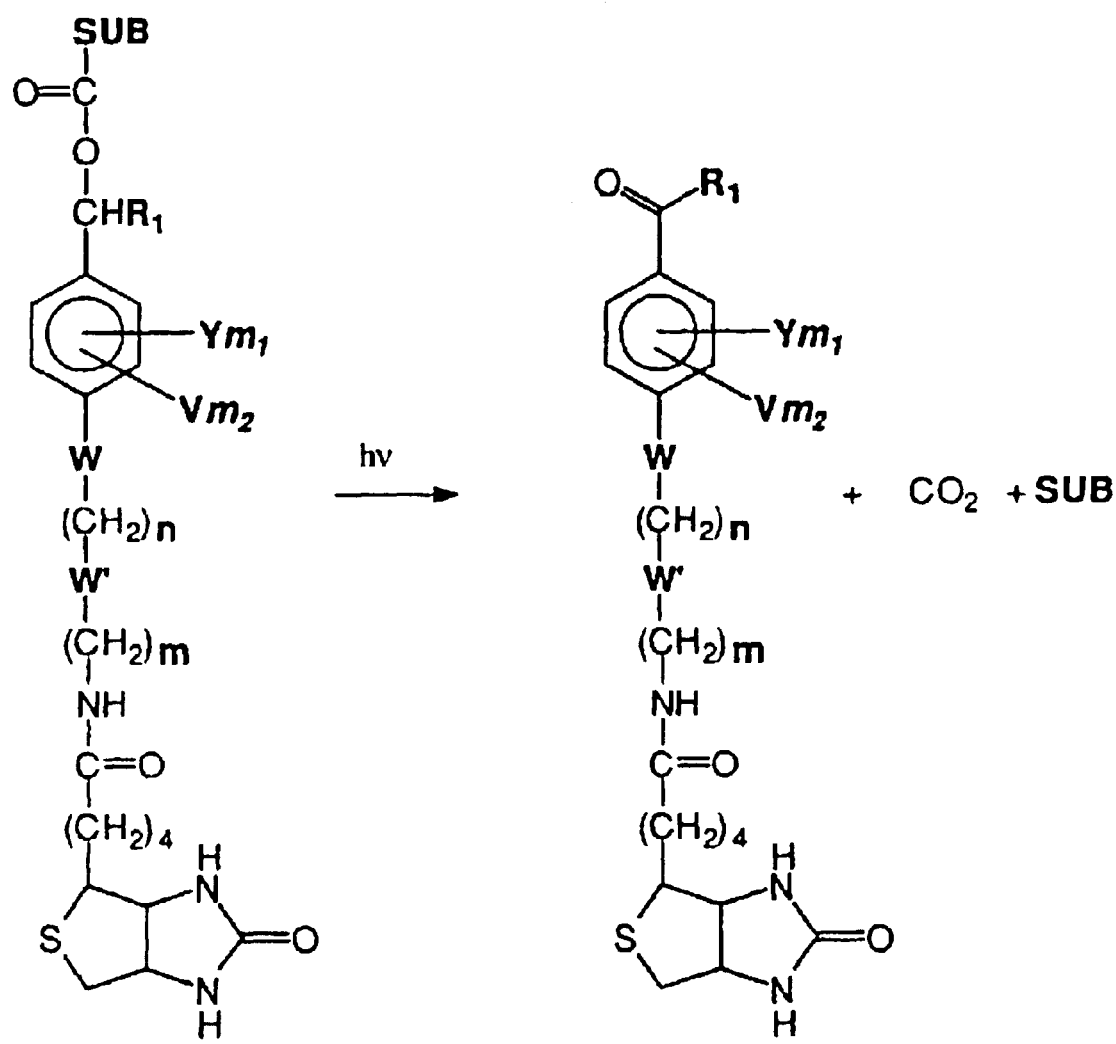
FIG. 7 Photolysis of PCBs.

Photocleavage of conjugates of the invention should preferably not damage released substrate or impair substrate activity. Proteins, nucleic acids and other protective groups used in peptide and nucleic acid chemistry are known to be stable to most wavelengths of radiation above 300 nm. PCB carbamates, for example, undergo photolysis upon illumination with long-wave UV light (320–400 nm), resulting in release of the unaltered substrate and carbon dioxide (FIG. 7). The yield and exposure time necessary for release of substrate photo-release are strongly dependent on the structure of photoreactive moiety. In the case of unsubstituted 2-nitrobenzyl PCB derivatives the yield of photolysis and recovery of the substrate are significantly decreased by the formation of side products which act as internal light filters and are capable of reacting with amino groups of the substrate. In this case, illumination times vary from about 1 minute to about 24 hours, preferably less than 4 hours, more preferably less than two hours, and even more preferably less than one hour, and yields are between about 1% to about 95% (V. N. R. Pillai, Synthesis 1, 1980). In the case of alpha-substituted 2-nitrobenzyl derivatives (methyl, phenyl), there is a considerable increase in rate of photo-removal as well as yield of the released substrate (J. E. Baldwin et al., Tetrahedron 46:6879, 1990; J. Nargeot et al., Proc. Natl. Acad. Sci. USA 80:2395, 1983).

The choice of a particular bioreactive agent depends on which molecular groups of the substrate are to be derivatized. For example, reaction of photocleavable biotin NHS-ester with a protein results in formation of a covalent bond with primary amino groups such as at the $\epsilon$-position of lysine residues or the $\alpha$-$NH_2$ group at the N-terminal of a protein. Normally, a number of lysine residues are exposed on the surface of a protein and available for such reaction. Alternatively, several other photocleavable biotins can be used which react with hydroxyl groups (—OH) present in tyrosine, threonine and serine residues, carboxyl groups (—COOH) present in aspartate and glutamate residues, and sulfhydryl groups (—SH) present in cysteine residues (Table 4). Thus, a wide variety of groups are available which are likely to be on the surface of a target protein.

Attachment of photocleavable biotin to molecules which bind proteins such as receptor ligands, hormones, antibodies, nucleic acids, and proteins that bind glycoproteins can also be accomplished because of the wide variety of reactive groups available for photocleavable biotins. For example, photocleavable biotin can be conveniently linked to antibodies which are directed against a particular protein. Alternatively, photocleavable biotins can be linked to DNA and RNA or to a variety of small molecules including receptor ligands and hormones. The importance of biotinylation of binding-complexes for isolation of proteins such as membrane receptors and splicesomes has already been demonstrated using conventional biotins or non-photocleavable biotins.

The choice of the detectable moiety depends on the substrate, its environment and the desired method of detection and isolation. For example, a substrate present in low concentrations may require a sensitive method of detection such as fluorescent spectroscopy thereby requiring a fluorescent moiety such as coumarin The wavelength of fluorescent emission can be selected by the choice of detectable moiety so as not to interfere with any natural fluorophores which may be present in the mixture. In cases where rapid isolation of the substrate is desired, choice of the detectable moiety may be determined by the availability of a suitable coupling agent. For example, an antigen which serves as the detectable moiety may be used if a suitable antibody is available. Since the detectable moiety, the reactive group and the photoreactive moieties are chemically separate in the bioreactive agent, the properties of each can be adjusted to meet the multiple requirements for detection and isolation of a particular substrate.

Conjugates of the invention may be attached to a solid support via the detectable moiety, the substrate or any other chemical group of the structure. The solid support may comprise constructs of glass, ceramic, plastic, metal or a combination of these substances. Useful structures and constructs include plastic structures such as microtiter plate wells or the surface of sticks, paddles, beads or microbeads, alloy and inorganic surfaces such as semiconductors, two and three dimensional hybridization and binding chips, and magnetic beads, chromatography matrix materials and combinations of these materials. Examples of the chemical structure of conjugates of the invention include:

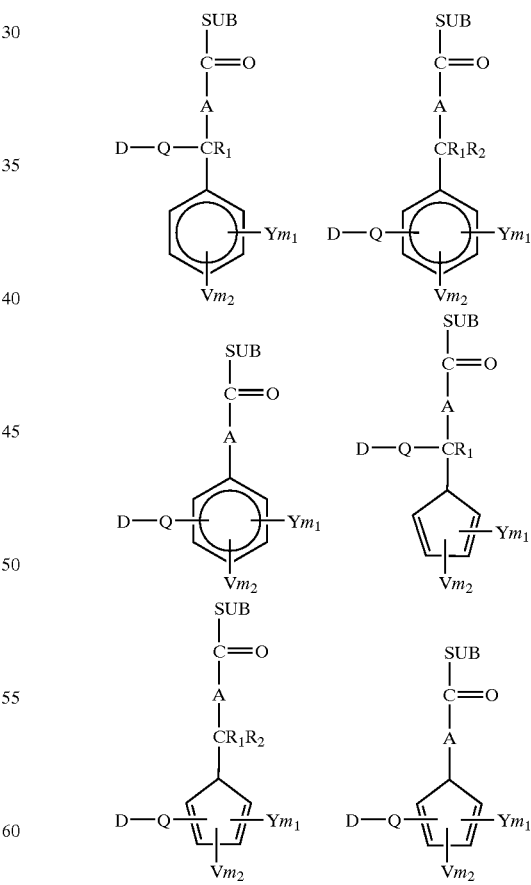

wherein SUB comprises a substrate; $R_1$ and $R_2$ are selected from the group consisting of hydrogen, alkyls, substituted alkyls, aryls, substituted aryls, —$CF_3$, —$NO_2$, —COOH and —COOR, and may be the same or different;

A is a divalent functional group selected from the group consisting of —O—, —S— and —NR$_1$; Y comprises one or more polyatomic groups which may be the same or different; V comprises one or more optional monoatomic groups which may be the same or different; Q comprises an optional spacer moiety; m1 and m2 are integers between 1–5 which can be the same or different; and D comprises a selectively detectable moiety which is distinct from R$_1$ and R$_2$.

Figure 8:
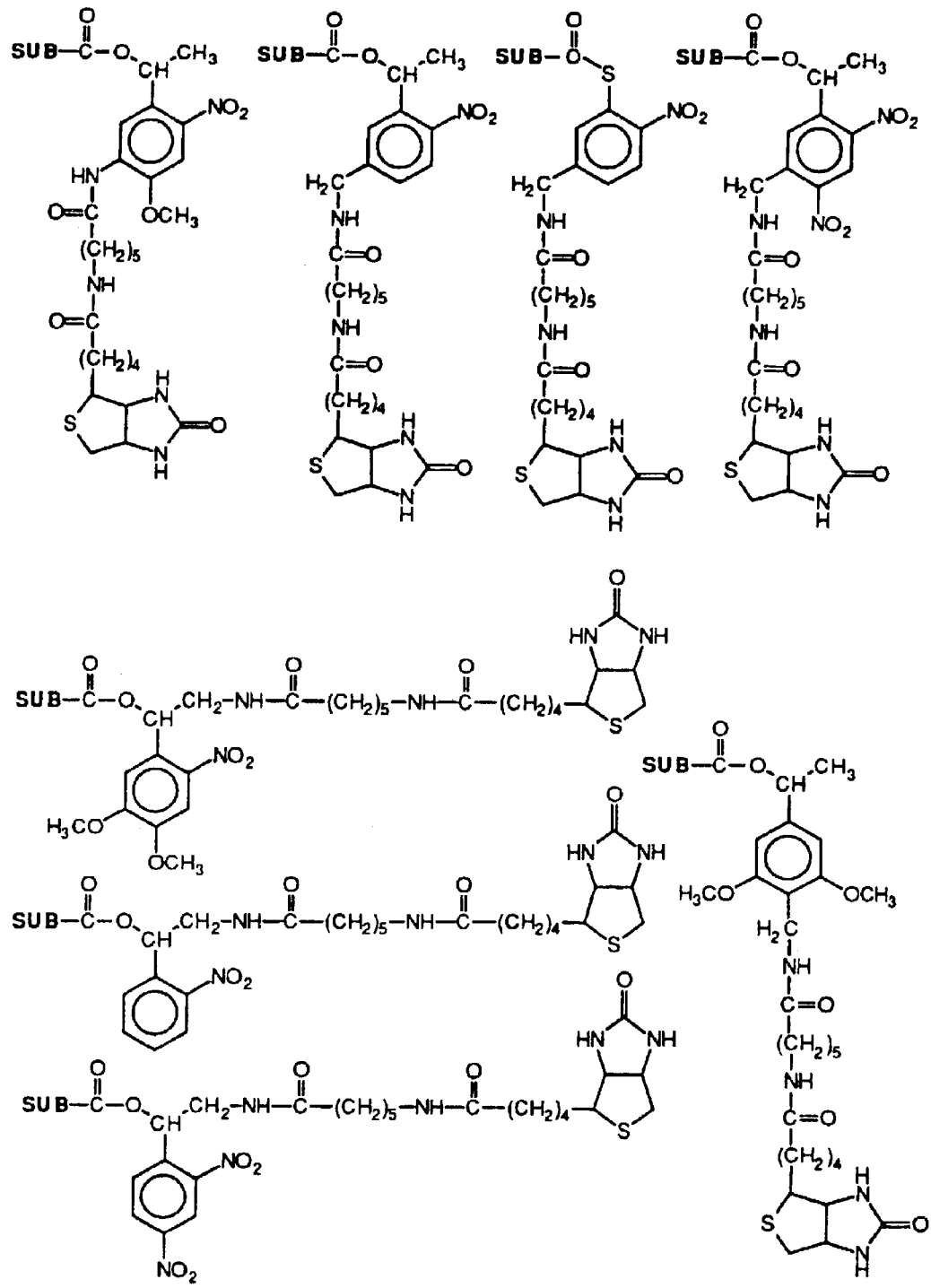
FIG. 8 PCB conjugates.

As discussed above, the polyatomic group may be one or more nitro groups, alkyl groups, alkoxyl groups, or derivatives or combinations thereof. The optional monoatomic group may be one or more fluoro, chloro, bromo or iodo groups, or hydrogen. The polyatomic and monoatomic groups and the chemical moieties at R$_1$ and R$_2$ may effect the photocleavage reaction such as the frequency of radiation that will initiate photocleavage or the the exposure time needed to execute a cleavage event. The spacer moiety (Q) may be a branched or unbranched hydrocarbon or a polymeric carbohydrate and is preferably represented by the formula:

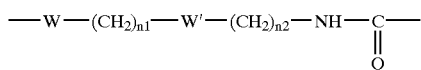

wherein W and W' are each selected from the group consisting of —CO—, —CO—NH—, —HN—CO—, —NH—, —O—, —S— and —CH$_2$—, and may be the same or different; and n1 and n2 are integers from 0–10 which can be the same or different and if either n1 or n2 is zero, then W and W' are optional. Specific examples of conjugates of the invention are depicted in FIG. 8.

Another embodiment of the invention is directed to conjugates which are pharmaceutical compositions. Compositions must be safe and nontoxic and can be administered to patients such as humans and other mammals. Composition may be mixed with a pharmaceutically acceptable carrier such as water, oils, lipids, saccharides, polysaccharides, glycerols, collagens and combinations thereof and administered to patients.

Pharmaceutical compositions with photo-releasable substrates are useful, for example, for delivery of pharmaceutical agents which have short half-lives. Such agents cannot be administered through current means without being subject to inactivation before having an effect. Pharmaceutical agents in the form of conjugates, covalently bound to bioreactive agents, are more stable than isolated agents. After general administration of the composition to the patient, the site to be treated is exposed to appropriate radiation releasing substrate which produces an immediate positive response in a patient. Uncoupling from the bioreactive agent at the point of maximal biological effect is an advantage unavailable using current administration or stabilization procedures. In an analogous fashion, other areas of the patient's body may be protected from the biological effect of the pharmaceutical agent. Consequently, using these conjugates, site-directed and site-specific delivery of a pharmaceutical agent is possible.

Another embodiment of the invention is directed to a method for isolating targets from a heterologous mixture. Bioreactive agents are contacted with the mixture to react with target forming the conjugate. Alternatively, conjugates can be contacted with the heterologous mixture to couple substrate within the conjugate to one or more targets. Conjugates can be separated from the mixture by any currently available techniques (e.g. Table 5).

TABLE 5

Affinity Techniques Using Avidin

| Material | Method of Separation |
| --- | --- |
| Magnetic beads coated with Streptavidin | Magnetic separation |
| Beads coated with Streptavidin | Washing (e.g. centrifugation) and elution |
| Biotinylated Antibodies | Immunoprecipitation |
| Cross-linked-bisacrylamide/azolactone copolymers with avidin | Column Chromatography |
| Agarose coated with Streptavidin | Column Chromatography |

Procedures such as chemical or physical separation of components of the mixture, electrophoresis, electroelution, sedimentation, centrifugation, filtration, magnetic separation, chemical extraction, affinity separation methods such as affinity chromatography or another chromatographic procedure such as ion-exchange, gradient separation, HPLC or FPLC, and combinations of these techniques are well-known and allow for a rapid isolation with a high efficiency of recovery (e.g. M. Wilchek et al., Methods Enzymol. 184, 1990; M. Wilchek et al., Anal. Biochem 171:1, 1988). After separation or isolation, targets can be easily quantitated using available methods such as optical absorbance or transmission (e.g. nucleic acid, proteins, lipids) or the Bradford (M. Bradford, Anal. Biochem. 72:248, 1976) or Lowry (O. Lowry et al., J. Biol. Chem. 193:265, 1951) assays (e.g. proteins), both of which are commercially available. After separation, coupled conjugates are treated with electromagnetic radiation to release substrate. The substrate targets can than be separated from the released bioreactive agent, if desired, to obtain substantially or completely pure targets.

Targets which can be detected and isolated in a highly purified form by this method include nearly any chemical, molecule or macromolecule including immune system modulators, agents of the hematopoietic system, cytokines, proteins, hormones, gene products, antigens, cells including fetal and stem cells, toxins, bacteria, membrane vesicles, virus particles, and combinations thereof. Detection and isolation are determined by the ability of the bioreactive agent to bind substrate. For example, nucleic acids can be base-paired to complementary nucleic acids, to nucleic acid binding proteins or to chemical moieties which react specifically with chemical moieties found on nucleic acids. Proteins can be bound with monoclonal or polyclonal antibodies or antibody fragments specific to those proteins, or chemical moieties which react specifically with chemical moieties found on the proteins of interest. Substrates may be, for example, precursors of targets such as one or more of the naturally or non-naturally occurring amino acids wherein the target is a nascent protein, or one or more ribonucleotides, deoxyribonucleotide or primers when the target is a nucleic acid. Precursor can be incorporated into target molecules by, for example, in vivo or in vitro replication, transcription or translation. Target may be a protein or protein-containing complex, nucleic acid, gene sequence or PCR product. Substrates may also be receptors which bind to or otherwise associate with ligands specific for the receptor molecules. Receptors which can be isolated include cytokines wherein the target is a cytokine receptor and antigens wherein the target is an antibody. Preferred conjugates for the detection and isolation of a target from a heterologous mixture are photocleavable biotins linked to antibodies (polyclonal, monoclonal, fragments), photocleavable coumarins linked to antibodies, photocleavable dansyls linked to lipids and derivatives and modifications thereof.

The heterologous mixture which contains target may be a biological sample, any proteinaceous composition such as a cellular or cell-free extract, nucleic acid containing compositions, a biomass containing, for example, vegetative or microbial material, a cell culture of primary or immortalized cells, lipid vesicles or even animals. Animals may be used to detect targets which may be present in the body or parts of the body or, alternatively, to collect and isolate targets such as macromolecules or cells from animal models. Substrate can also be proteins, peptides, amino acids, amino acid analogs, nucleosides, nucleotides, lipids, vesicles, detergent micells, fatty acids, saccharides, polysaccharides, inorganic molecules, metals and derivatives and combinations thereof In an application of this method, the substrate may be an integral component of the target such as a nucleotide in the detection and isolation of nascent nucleic acids or an amino acid in the detection and isolation of nascent proteins. Substrate is incorporated into target by chemical or enzymatic techniques and detected and isolated by the presence of the detectable moiety. Briefly, conjugates are contacted with reagents in a heterologous mixture such as, for example, in a replication, transcription, translation or coupled transcription/translation system. Substrates are incorporated into targets through the action of components in the system such as enzymes, precursor molecules and other reagents of the system. Conjugate coupled targets are separated from the mixture and treated with electromagnetic radiation to release the .target which is then isolated.

Conjugates can be contacted with a heterologous mixture by incubation as in, for example, the enzymatic incorporation of a macromolecular precursor into a nascent macromolecule which may be either in vivo or in vitro. Nucleic acid polymerases will incorporate precursor nucleotides or nucleic acid primers into nucleic acids. In vitro incubations in cell-free reaction mixture are typically performed at a temperature of between about 4° C. to about 45° C., preferably at between about 12° C. to about 37° C., and more preferably at about room temperature. Incubation of conjugates into nascent macromolecules may be complete in about 5 minutes, about 15 minutes, or about one hour depending on the incubation conditions, or may require two, three or more hours to complete. When the heterologous mixture is an animal or an animal model in vivo incubations are generally performed at body temperature and may require hours or days for conjugates to distribute to areas of the animal's body which may be remote from the site of introduction, for conjugates to react with targets and for conjugates coupled with targets to be collected.

One of the preferred embodiments of the invention relates to the detection or isolation of protein using photocleavable biotin. In one application of this embodiment, PCB is reacted with a protein through the formation of covalent bonds with specific chemicals groups of the protein forming a conjugate. The protein may be either the target to be isolated or detected or a probe for the target protein such as an antibody. The target protein can then be isolated using streptavidin affinity methodology.

Another application of this embodiment is directed to the use of photocleavable biotin to isolate nascent proteins that can be created from in vitro or in vivo protein synthesis. Basically, photocleavable biotins are synthesized and linked to amino acids (PCB-amino acids) containing special blocking groups. These conjugates are charged to tRNA molecules and incorporated into peptides and proteins using a translation or coupled transcription/translation system. PCB-amino acids of the invention have the property that once illuminated with light, a photocleavage occurs that produces a native amino acid plus the free biotin derivative. Such proteins can be isolated in a structurally and/or functionally unaltered form.

The detailed procedure for the production of photocleavable biotin amino acids and their incorporation into the nascent proteins involves a few basic steps. First, photocleavable biotin is synthesized and linked to an amino acid with an appropriate blocking group. These PCB-amino acid conjugates are charged to tRNA molecules and subsequently incorporated into nascent proteins in an in vivo or in vitro translation system. Alternatively, a tRNA molecule is first charged enzymatically with an amino acid such as lysine which is then coupled to a reactive PCB. Nascent proteins are separated and isolated from the other components of synthesis using immobilized streptavidin. Photocleavage of PCB-streptavidin complex from the nascent protein generates a pure and native, nascent protein.

Figure 9:
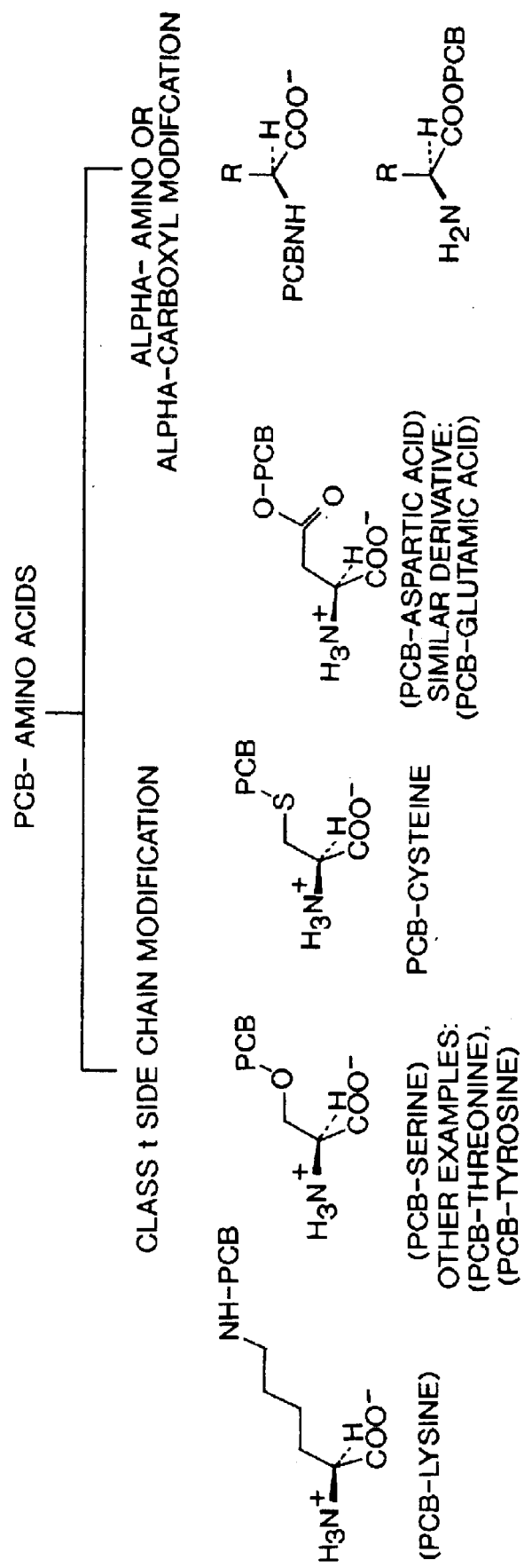
FIG. 9 Possible amino acid linkages of PCB.

PCB is attached to an amino acid using, for example, the side-chain groups such as an amino group (lysine), aliphatic and phenolic hydroxyl groups (serine, threonine and tyrosine), sulfhydryl group (cysteines) and carboxylate group (aspartic and glutamic acids) (FIG. 9). Synthesis can be achieved by direct condensations with appropriately protected parent amino acids. For example, lysine side chain amino group can be modified with PCB by modification of the ε-amino group. The synthesis of, for example, PCB-methionine involves primarily α-amino group modification. PCB-methionine can be charged to an initiator tRNA which can participate in protein synthesis only at initiation sites which results in single PCB incorporation per copy of the nascent protein.

Figure 10A:
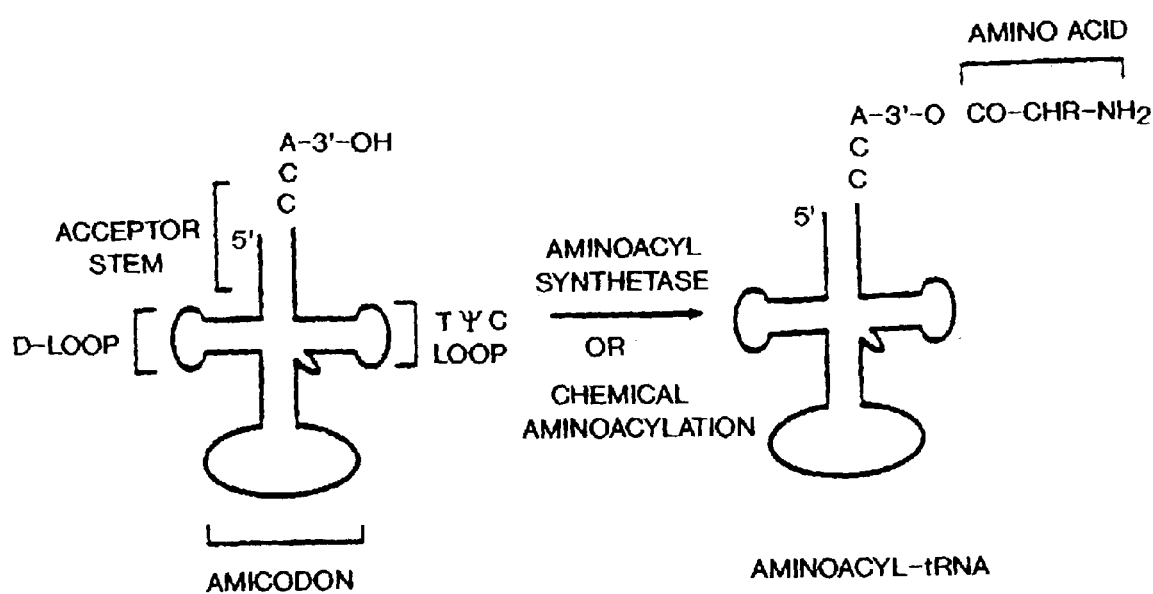
FIG. 10 (A) Aminoacylation of tRNA, and (B) a comparison between enzymatic 5 and chemical aminoacylation.
Figure 10B:
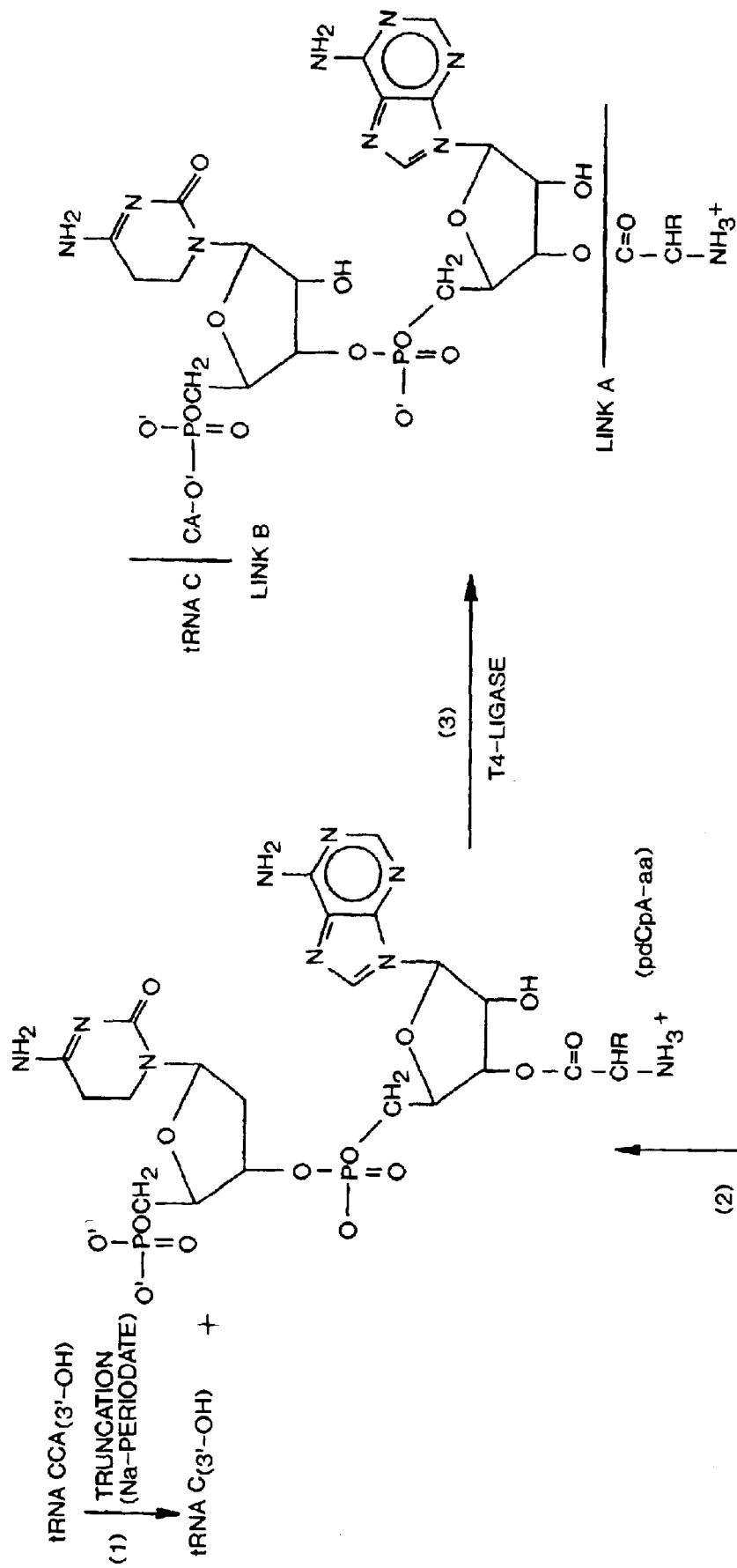

One method for incorporation of a photocleavable biotin amino acid into a nascent protein involves misaminoacylation of tRNA Normally, a species of tRNA is charged by a single, cognate native amino acid. This selective charging, termed here enzymatic aminoacylation, is accomplished by enzymes called aminoacyl-tRNA synthetases and requires that the amino acid to be charged to a tRNA molecule be structurally similar to a native amino acid. Chemical misaminoacylation can be used to charge a tRNA with a non-native amino acids such as photocleavable amino acids. The specific steps in chemical misaminoacylation of tRNAs are depicted in FIG. 10.

As shown, tRNA molecules are first truncated to remove the 3'-terminal residues by successive treatments with periodate, lysine (pH 8.0) and alkaline phosphate (Neu et al., J. Biol. Chem. 239:2927–34, 1964). Alternatively, truncation can be performed by genetic manipulation, whereby a truncated gene coding for the tRNA molecule is constructed and transcribed to produce truncated tRNA molecules (Sampson et al., Proc. Natl. Acad. Sci. USA 85:1033, 1988). Second, protected acylated dinucleotides, pdCpA, are synthesized (Hudson, J. Org. Chem. 53:617, 1988; E. Happ, J. Org. Chem. 52:5387, 1987). PCB-amino acids blocked appropriately at their side chains and/or at α-amino groups, using standard protecting groups like Fmoc, are prepared and coupled with the synthetic dinucleotide in the presence of carboxy group activating reagents. Subsequent deprotection of Fmoc groups yields aminoacylated dinucleotide.

Third, the photocleavable biotin amino acid is ligated to the truncated tRNA through the deprotected dinucleotide. The bond formed by this process is different from that resulting from tRNA activation by an aminoacyl-tRNA synthetase, however, the ultimate product is the same. T4 RNA ligase does not recognize the O-acyl substituent, and is thus insensitive to the nature of the attached amino acid (FIG. 10). Misaminoacylation of a variety of non-native amino acids can be easily performed. The process is highly sensitive and specific for the structures of the tRNA and the amino acid.

Aminoacylated tRNA linked to a photocleavable biotin amino acid can also be created by employing a conventional aminoacyl synthetase to aminoacylate a tRNA with a native amino acid or by employing specialized chemical reactions which specifically modify the native amino acid linked to the tRNA to produce a photocleavable biotin aminoacyl-tRNA derivative. These reactions are referred to as post-aminoacylation modifications. Such post aminoacylation modifications do not fall under the method of misaminoacylation, since the tRNA is first aminoacylated with its cognate described amino acid.

In contrast to chemical aminoacylation, the use of post-aminoacylation modifications to incorporate photocleavable biotin non-native amino acids into nascent proteins is very useful since it avoids many of the steps including in misaminoacylation. Furthermore, many of the photocleavable biotin derivatives can be prepared which have reactive groups reacting specifically with desired side chain of amino acids. For example, postaminoacylation modification of lysine-tRNA$^{Lys}$, an N-hydroxysuccinimide derivative of PCB can prepared that would react with easily accessible primary ε-amino and minimize reactions occurring with other nucleophilic groups on the tRNA or α-amino groups of the amino acylated native amino acid. These other non-specific modifications can alter the structure of the tRNA structure and severely compromise its participation in protein synthesis. Incomplete chain formation could also occur when the α-amino group of the amino acid is modified. Post-aminoacylation modifications to incorporate lysine-biotin non-native amino acids into nascent proteins has been demonstrated (tRNA$^{nacend}$™; Promega; Madison, Wis.) used for the detection of nascent protein containing biotin using Western Blots followed by enzymatic assays for biotin (T. V. Kurzchalia et al., Eur. J. Biochem. 172:663–68, 1988). However, these biotin derivatives are not photocleavable which, in the case of NHS-derivatives of PCB, allows the biotin linkage to the lysine to be photochemically cleaved.

PCB-amino acids can also be incorporated into polypeptide by means of solid-support peptide synthesis. First, PCB-amino acids are derivatized using base labile fluorenylmethyloxy carbonyl (Fmoc) group for the protection of α-amino function and acid labile t-butyl derivatives for protection of reactive side chains. Synthesis is carried out on a polyamide-type resin. Amino acids are activated for coupling as symmetrical anhydrides or pentafluorophenyl esters (E. Atherton et al., *Solid Phase Peptide Synthesis*, IRL Press, Oxford, 1989). Second, amino acids and PCB are coupled and the PCB-amino acid integrated into the polypeptide chain. Side chain PCB-derivatives, like ε-amino-Lys, side chain PCB-amino acid esters of Glu and Asp, esters of Ser, Thr and Tyr, are used for incorporation at any site of the polypeptide. PCB-amino acids may also be incorporated in a site-specific manner into the chain at either predetermined positions or at the N-terminus of the chain using, for example, PCB-derivatized methionine attached to the initiator tRNA.

A wide range of polypeptides can be formed from PCB-amino acids cytokines and recombinant proteins both eukaryotic and prokaryotic (e.g. α-, β- or γ-interferons; interleukin-1, -2, -3, etc.; epidermal, fibroblastic, stem cell and other types of growth factors), and hormones such as the adrenocorticotropic hormones (ACTHs), insulin, the parathyroid hormone (bPTH), the transforming growth factor β (TGF-β) and the gonadotropin releasing hormone (GnRH) (M. Wilchek et al., Methods Enzymol. 184:243, 1990; F. M. Finn et al., Methods Enzymol. 184:244, 1990; W. Newman et al., Methods Enzymol. 184:275, 1990; E. Hazum, Methods Enzymol. 184:285, 1990). These hormones retain their binding specificity for the hormone receptor. One example is the GnRH hormone where a biotin was attached to the epsilon amino group Lys-6 through reaction of a d-biotin p-nitrophenyl ester. This biotinylated hormone can be used for isolation of the GnRH receptor using avidin coated columns.

Figure 11:
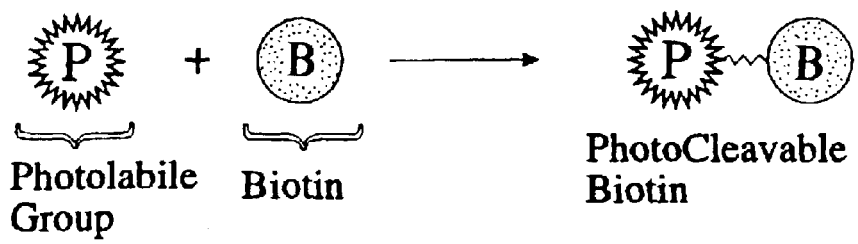
FIG. 11 The four basic steps in the isolation of pure substrate using PCB.
Figure 11:
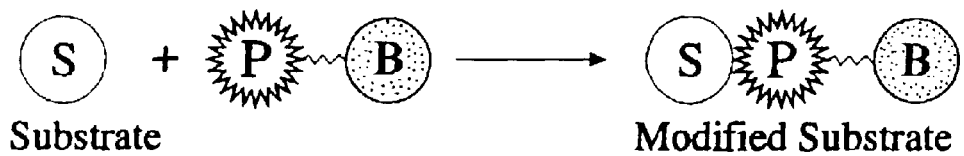
Figure 11:
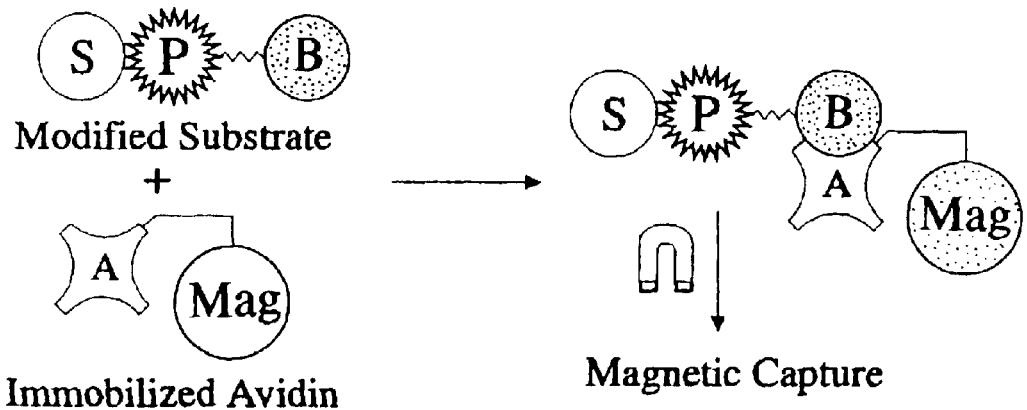
Figure 11:
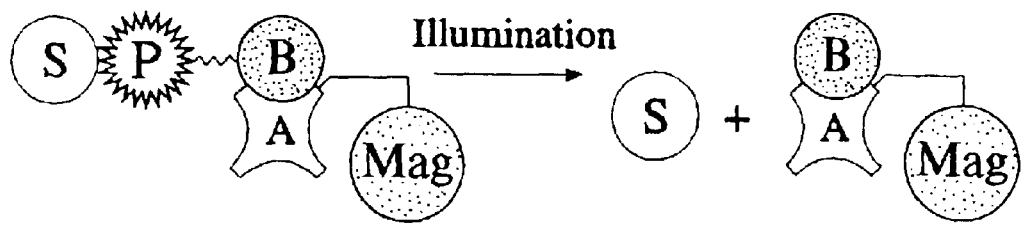

After incorporation or attachment of PCB into a protein, protein-complex or other amino acid-containing target, the target is isolated using a simple four step procedure (FIG. 11). First, a bioreactive agent (PCB) is synthesized. Second, a substrate is coupled to the bioreactive agent forming a conjugate. Third, target is separated from other materials in the mixture through the selective interaction of the photocleavable biotin with avidin, streptavidin or their derivatives. Captured targets may be immobilized on a solid support such as magnetic beads, affinity column packing materials or filters which facilitates removal of contaminants. Finally, the photocleavable biotin is detached from the target by illumination of a wavelength which causes the photocleavable biotin covalent linkage to be broken. Targets are dissolved or suspended in solution at a desired concentration. In those situations wherein conjugate coupled targets are not attached to solid supports, release of targets can be followed by another magnetic capture to remove magnetic particles now containing avidin/streptavidin bound biotin moiety released form the photocleavage of PCB. Thus, a completely unaltered protein is released in any solution chosen, in a purified form and at nearly any concentration desired.

Another example for the use of PCB is where the conjugate comprises a PCB-coupled antibody. The use of photocleavable biotin provides a means for recovering target molecule and the antibody for subsequent use. Release of a protein from binding complex can be performed subsequent to release of the binding complex from the immobilized streptavidin. This is an advantage since it enables the release to be performed under well controlled conditions. For example, elution of a target protein from an affinity column often requires changes in buffer and/or use of a competitive agent such as an epitope which competes for an antibody binding site. This can require long exposure of the protein to damaging conditions or the need for increased amounts of the competitive agent which can be prohibitively expensive. In contrast, once the protein complex is removed from the immobilized streptavidin by photocleavage, the complex can be separated more conveniently. In the case where antibodies are used as the substrate, an additional advantage of the invention is that the antibody can also be recovered in an unaltered and purified form.

Figure 12A:
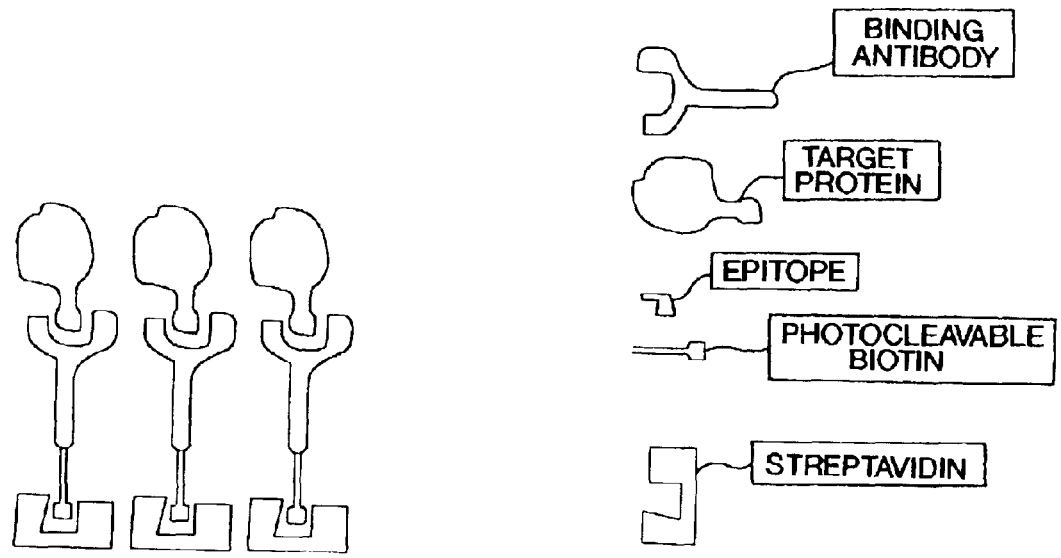
FIG. 12 Method for the detection of target protein and its antibody using PCB.
Figure 12A:
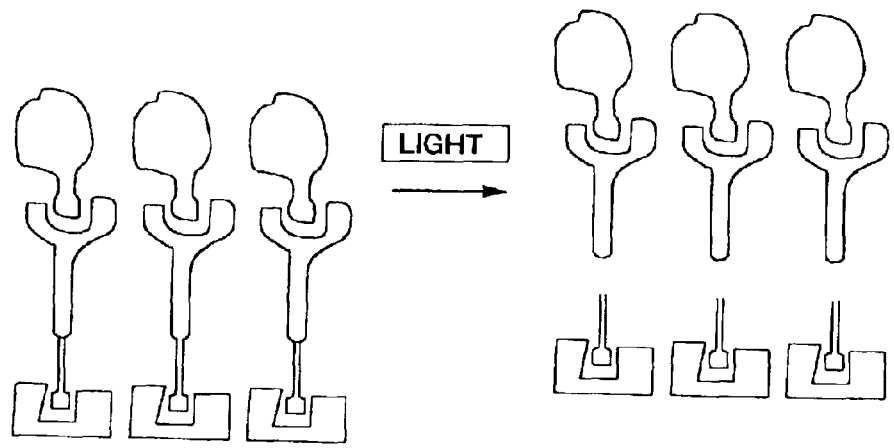
Figure 12B:
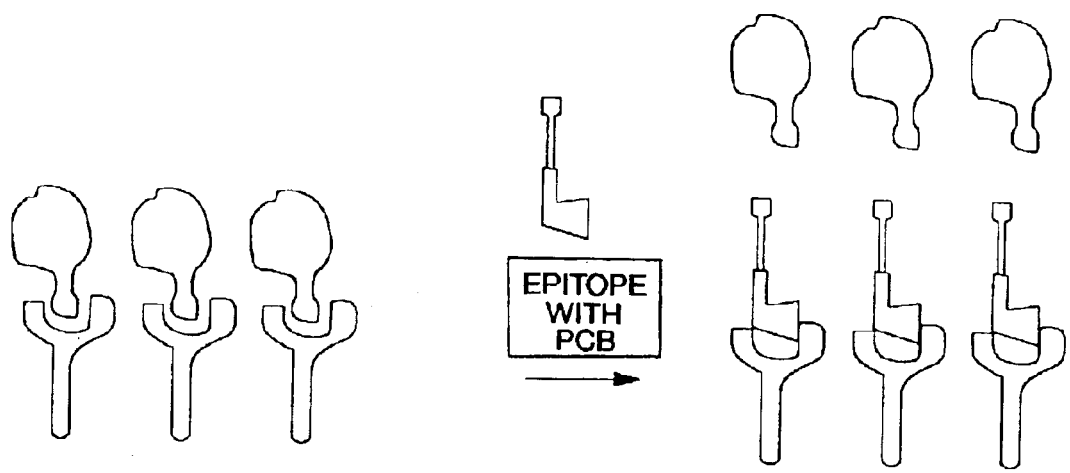
Figure 12B:
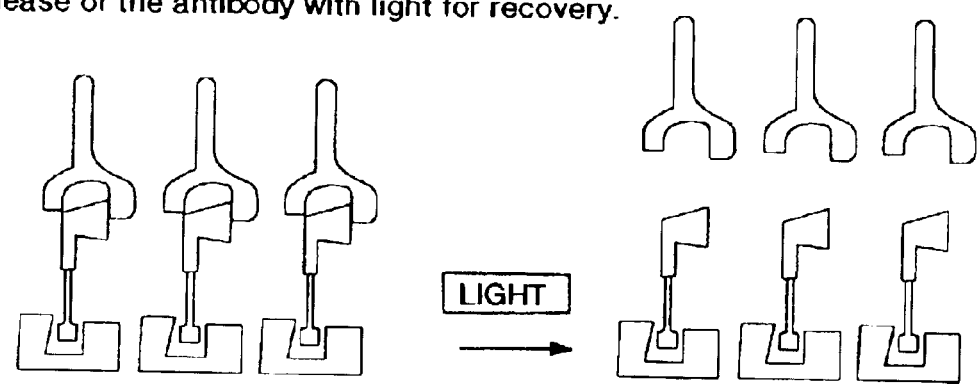

A simple scheme for using a PCB-antibody is shown in FIGS. 12A and 12B. Target protein/antibody conjugated to photocleavable biotin is then immobilized with streptavidin. Target protein/antibody is decoupled by illumination with light and the target protein/antibody released. Target protein is separated from antibody using, for example, increased or decreased salt (NaCl, KCl) concentrations and recovered. Alternatively, as shown in FIG. 12B, the target is removed from the antibody by using an epitope-PCB conjugate which competes for the antibody binding site. The antibody-epitope-PCB conjugate is then isolated from the target by immobilization with streptavidin. The antibody-epitope complex is then released by photocleaving the biotin-epitope complex. A wide variety of other molecules that interact with proteins can also be utilized in conjunction with PCB for protein isolation, as shown in Table 2, including polypeptides, protein complexes and small ligands.

PCB derivatives attached or incorporated into antibodies or other macromolecules such as DNA which serve as hybridization probes can also be used advantageously for sequential multiple detection of targets. As in the case of conventional assays for target based on streptavidin-biotin interactions, the presence of the target is signaled by a streptavidin-enzyme complex which binds to the biotinylated probe and produces an amplified signal by converting a substrate into a product which is easily detectable due to a distinctive physical property such as color or luminescence. However, in contrast to conventional biotins, the PCB derivatives can be completely removed allowing for separation removal of the streptavidin-enzyme complex and subsequent addition of new probes and streptavidin complexes for the detection of additional target molecules. A similar advantage exists for cytochemical labeling based on streptavidin-biotin interaction. In this case, the label can be completely removed by light, allowing for additional specific cytochemical labels to be used.

In another application of the preferred embodiment, photocleavable biotin or a PCB derivative can be incorporated into a DNA (deoxyribonucleic acid), RNA (ribonucleic acid) or PNA (polynucleic amide; P. E. Nielsen et al., Sci. 254:1497–1500, 1991) molecule produced by, for example, chemical synthesis, PCR, nick translation or DNA or RNA polymerases (Table 6). Target DNA or RNA can then be isolated by using streptavidin affinity methods similar to methods discussed above. Isolation is accomplished, for example, using commercially available magnetic beads coated with streptavidin. Beads will bind tightly to all DNA and RNA containing the PCB derivative, whereas all other molecules are washed away. The photocleavable biotin is then removed from the target nucleic acid by illumination.

Figure 13A:
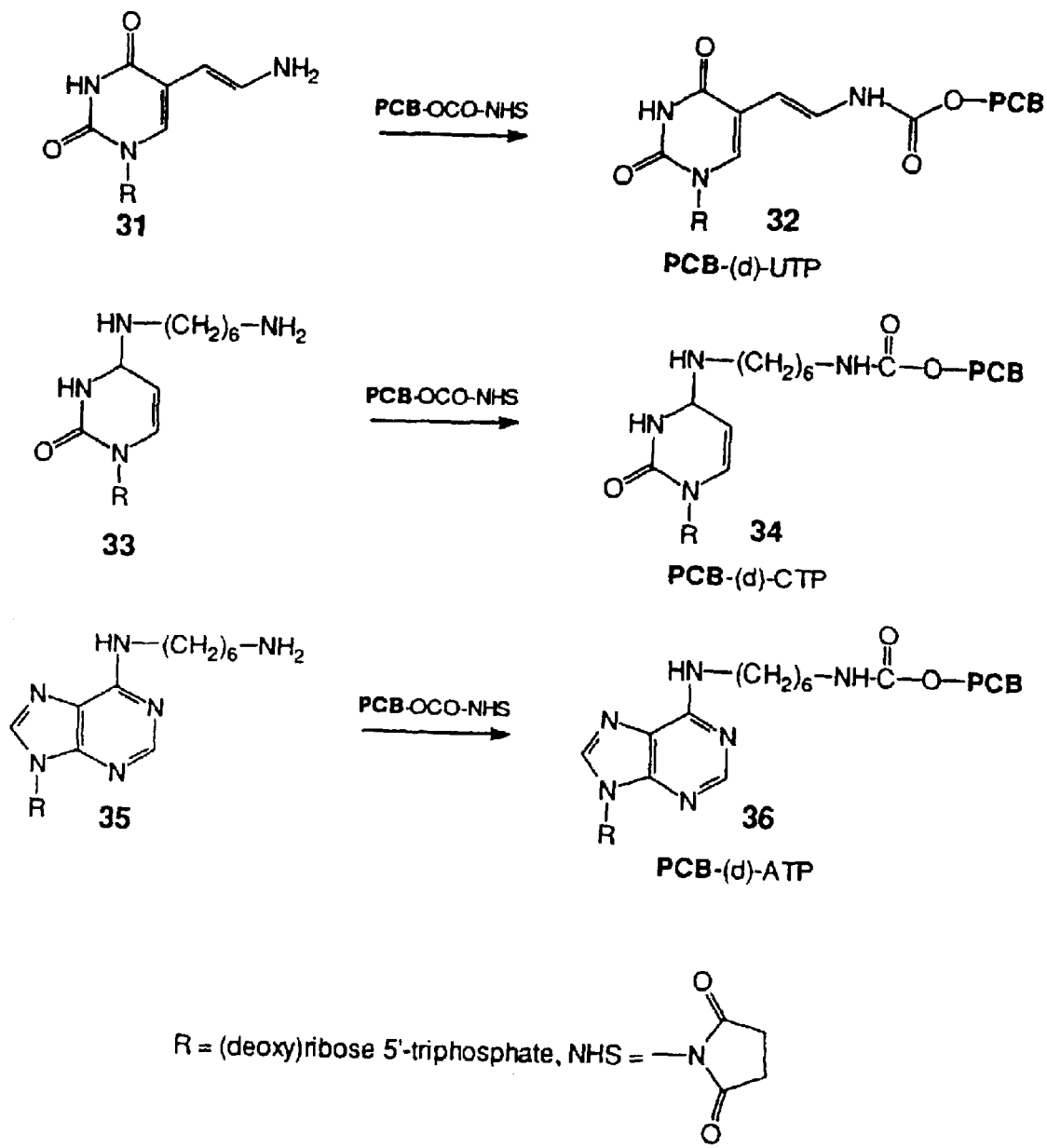
FIG. 13 PCB-phosphoramidites and PCB-nucleotides.

The incorporation of PCB into nucleic acids such as DNA and RNA involves the synthesis and use of compounds that are formed from the derivatization of nucleotides with photocleavable biotins. Examples of the nucleotides modified using photocleavable biotin are shown FIG. 13A.

Non-specific incorporation of PCB moieties into nucleic acids is achieved, for example, using bisulfite catalyzed cytosine transamination and subsequent reaction with PCB-NHS ester or PCB-NH-NH$_2$(PCB-hydrazide). Alternatively, 5'-phosphate can be converted into phosphoramidite by reaction with water soluble carbodiimide, imidazole and diamine and the resulting phosphoramidite reacted with PCB-NHS ester.

Numerous methods have been developed to introduce an amino group on 5'-end of protected oligonucleotides during solid support synthesis. These include carbonyl diimidazole mediated modification of 5'-OH with diamine and introduction of aliphatic amine moiety on 5'- or 3'-end during synthesis using special phosphoramidites. Bifunctional phosphoramidites have also been developed that allow for incorporation of reactive amino group into multiple sites in synthetic oligonucleotides. These methods produce oligonucleotide products bearing aliphatic amino groups, which can be easily converted into PCB-carbamates by reaction with respective PCB-NHS esters. In an analogous manner as conventional biotin, PCB moieties can be directly incorporated into oligonucleotides during solid support synthesis using respective PCB-phosphoramidites.

Synthetic oligonucleotides of predetermined or random sequences have a variety of uses as, for example, primers, hybridization probes and antisense sequences. The synthesis of DNA and RNA oligonucleotides utilizes phosphoramidite chemistry and is routinely performed on an automated synthesizer with the growing nucleic acid chains attached to a solid support such as CPG (controlled pore glass). In this manner, phosphoramidites and other reagents can be added in excess and removed by filtration The synthesis cycle comprises four reactions. First, acid labile trityl groups are removed from the 5'-OH groups. Second, phosphoramidites are coupled to the 5'-OH. Third, unreacted 5'-OH groups are protected by capping with acetyl groups. Finally, internucleotide linkage is converted from phosphite to phosphotriester by oxidation. This cycle is repeated until the desired sequence is obtained after which, oligonucleotide is cleaved from solid support and purified using, for example, gel electrophoresis and HPLC.

Coupling efficiency for each step is preferably as high as possible such as greater than 90% or about 97–99%. Unreacted molecules are eliminated at each step by capping with acetyl groups preventing the formation of undesired sequences. Crude oligonucleotide contains besides full length sequence numerous shorter sequences also called the failure sequences. Purification of such a complex mixture is difficult especially when it comes to isolation of full-length sequence from slightly shorter failure sequences (e.g. n–1; n–2). This problem becomes even more difficult when synthesizing long sequences of DNA or RNA where coupling efficiencies are lower and the number of failure sequences higher. 5'-PCB-phosphoramidites can be used to selectively labile full-length oligonucleotides at their 5'-end during solid-support synthesis on automated nucleic acid synthesizers.

PCB-phosphoramidites can contain the PCB moiety linked to a phosphoramidite functionality through a spacer arm allowing for efficient binding to avidin. This reagent selectively reacts with the 5'-OH group on a sugar ring and can be used on automated synthesizers. Biotinylated sequences can also be prepared using standard synthesis cycles with coupling efficiency being monitored by trityl analysis. Typical coupling efficiencies are between about 90–95%. In addition, photocleavage of 5'-PCB nucleic acid results in formation of 5'-phosphorylated sequences. 5'-phosphorylated oligonucleotides are required for most applications in molecular biology.

Alternatively, PCB moieties can also be incorporated during synthesis into oligonucleotides at any position including the 3'-terminus, and into multiple sites using PCB-phosphoramidites utilizing, for example, bifunctional non-nucleosidic backbones. Enzymes including the Taq DNA polymerase used in PCR reactions, and other DNA and RNA polymerases are capable of incorporating biotinylated nucleotides into nucleic. acids. PCR technology comprises the process of amplifying one or more specific nucleic acid sequences in a nucleic acid using primers and agents for enzymatic polymerization followed by detection of the now amplified sequence (R. K. Saild et al., Sci. 230:1350, 1985; T. J. White et al., Trends Gent. 5:185, 1989). The basic techniques are described in U.S. Pat. No. 4,683,195, which is specifically incorporated by reference, and variations thereof described in U.S. Pat. Nos. 5,043,272, 5,057,410 and 5,106,727, which are also specifically incorporated by reference. Several examples exist where biotinylated nucleotides have been efficiently incorporated during the PCR applications. These studies demonstrate that PCR carried out in the presence of PCB-nucleotides results in a large amplification of target DNA fragment and simultaneous labeling with PCB. The primers required for PCR reaction may also be labeled.

Table 6 lists different enzymatic methods that would allow incorporation of PCB-nucleotides to generate labeled probes for many applications like in situ hybridization and PCR.

TABLE 6

Enzymatic Methods for Incorporation of PCB-Nucleotides

| Method | Substrate | Enzyme | Remarks |
| --- | --- | --- | --- |
| Nick Translation | DNA or RNA | E. coli DNA pol I | Most popular method |
| Replacement synthesis using T4 DNA polymerase | double stranded DNA | T4 DNA Polymerase | High specific incorporation in dsDNA |
| Reverse transcriptase | RNA | Molony murine leukemia virus reverse transcriptase | Preparation of long cDNA copies of RNA |
| 3'-Terminal labeling | ds DNA | terminal deoxynucleotidyl transferase | 3'-hydroxyl terminal labeling of dsDNA |
| RNA labeling | RNA | SP6 Polymerase T3 or T7 RNA Polymerase | T3 RNA is the most efficient for RNA labeling |
| Post-transcription labeling | RNA | SP6, T3 or T7 Pol | Incorporate allylamine-UTP first followed by its modification by PCB |
| 3'-labeling of RNA | RNA (including tRNAs etc) | T4 RNA ligase | Based on ADP derivatives of PCB. |

Biotin-avidin technology is currently used extensively in the field of molecular biology and biomedicine as a means for efficiently isolating the products of DNA and RNA synthesis as well as for detection of specific sequences in nucleic acids. Isolation normally involves the attachment or incorporation of biotin into the DNA or RNA followed by separation through the interaction of the biotin with streptavidin. For example, this methodology is used widely for the isolation of DNA, which is the product of the polymerase chain reaction. Detection typically involves the preparation of biotin labeled nucleic acid probes. These probes have found wide-spread application in gene structure and gene function studies, the diagnosis of human, animal and plant pathogens, and the detection of human genetic abnormalities.

However, conventional methodologies are limited by the difficulty of detaching or releasing biotin from the nucleic acid. In particular, it is highly desirable to obtain unaltered DNA or RNA after it is separated by the biotin-avidin interaction. For example, the presence of biotin on the nascent DNA can interfere with its subsequent utilization in cloning or hybridization analysis. In addition, the inability to remove biotin from a biotinylated nucleic acid probe after an enzyme linked assay prevents additional hybridization assays from being performed on the same sample.

The utilization of photocleavable biotins in the isolation or detection of nucleic acids eliminates many of the difficulties listed above by providing a rapid and effective method of removing the biotin in a single step. In the case of biotin-avidin based isolation of DNA this also accomplishes the step of releasing the DNA from the immobilized avidin.

In a preferred embodiment of this invention, the isolation of nucleic acids is based on three basic steps. First, a photocleavable biotin derivative is attached to a nucleic acid molecule by enzymatic or chemical means or, alternatively, by incorporation of a photocleavable biotin nucleotide into a nucleic acid by enzymatic or chemical means. The choice of a particular photocleavable biotin depends on which molecular groups are to be derivatized on the nucleic acid. For example, attachment of photocleavable biotin to a nucleic acid can be accomplished by forming a covalent bond with the aromatic amine, sugar hydroxyls or phosphate groups (Table 4). PCB can also be incorporated into oligonucleotides through chemical or enzymatic means. Next, the nucleic acid molecule is separated through the selective interaction of the photocleavable biotin with avidin, streptavidin or their derivatives which can be immobilized on a material such as magnetic beads, affinity column packing materials or filters. Methods for the separation of nucleic acids from other molecules in a complex mixture using photocleavable biotin are well-established and similar to the more conventional methods utilizing non-cleavable biotin. This typically involves an affinity technique based on streptavidin-biotin interaction whereby the nucleic acid containing biotin is immobilized due to its interaction with streptavidin. These techniques include, as shown in Table 5, streptavidin-coated magnetic beads, streptavidin-sepharose columns and streptavidin conjugated filters, all of which are commercially available. For example, nucleic acid molecules containing PCB either through attachment or incorporation are isolated using streptavidin-coated magnetic beads. The pool of unbound biomolecules is then: washed to remove other reactants, buffer and salts. Finally, the photocleavable biotin is detached from the nucleic acid by illumination at a wavelength which causes the photocleavable biotin covalent linkage to be broken. The bioreactive agent can be removed leaving a substantially or completely pure nucleic acid.

Another aspect of the invention is directed to the use of photocleavable conjugates in conjunction with PCR amplification. Methods for the isolation of a PCR product may use one or more oligonucleotide primers as substrates. The nucleic acid sequence of the target is PCR amplified using the conjugated primers. Covalent bonds between the primer and the bioreactive agent are selectively cleavable with electromagnetic radiation to release the amplified sequences. Nucleotide sequences which can be selectively amplified by this method includes nucleotide sequences found in biological samples, bacterial DNA and eukaryotic DNA. In contrast to conventional biotins, PCB offers an effective method to completely remove biotinylated DNA product of the polymerase chain reaction and provides a means to simultaneously release the PCR product from the avidin or streptavidin binding medium and remove the biotinylation in a single step.

Other advantages over conventional biotins include the elimination of the need for special reagents or buffers. After photocleavage of biotin from the PCR product, the resulting DNA is suitable for cloning and other common usages in molecular biology. After photocleavage of biotin from the PCR product, it can be accurately analyzed with standard analytical methods such as gel electrophoresis. Hybridization probes containing PCB can be sterilized, wherein the biotin is completely removed so that the target DNA can be reprobed using a second biotinylated probe. The PCB incorporated into DNA retains the high binding affinity to avidin unlike the several derivatives of biotin where properties of biotin are attenuated for the purposes of easy release (e.g. iminobiotin).

Figure 14A:
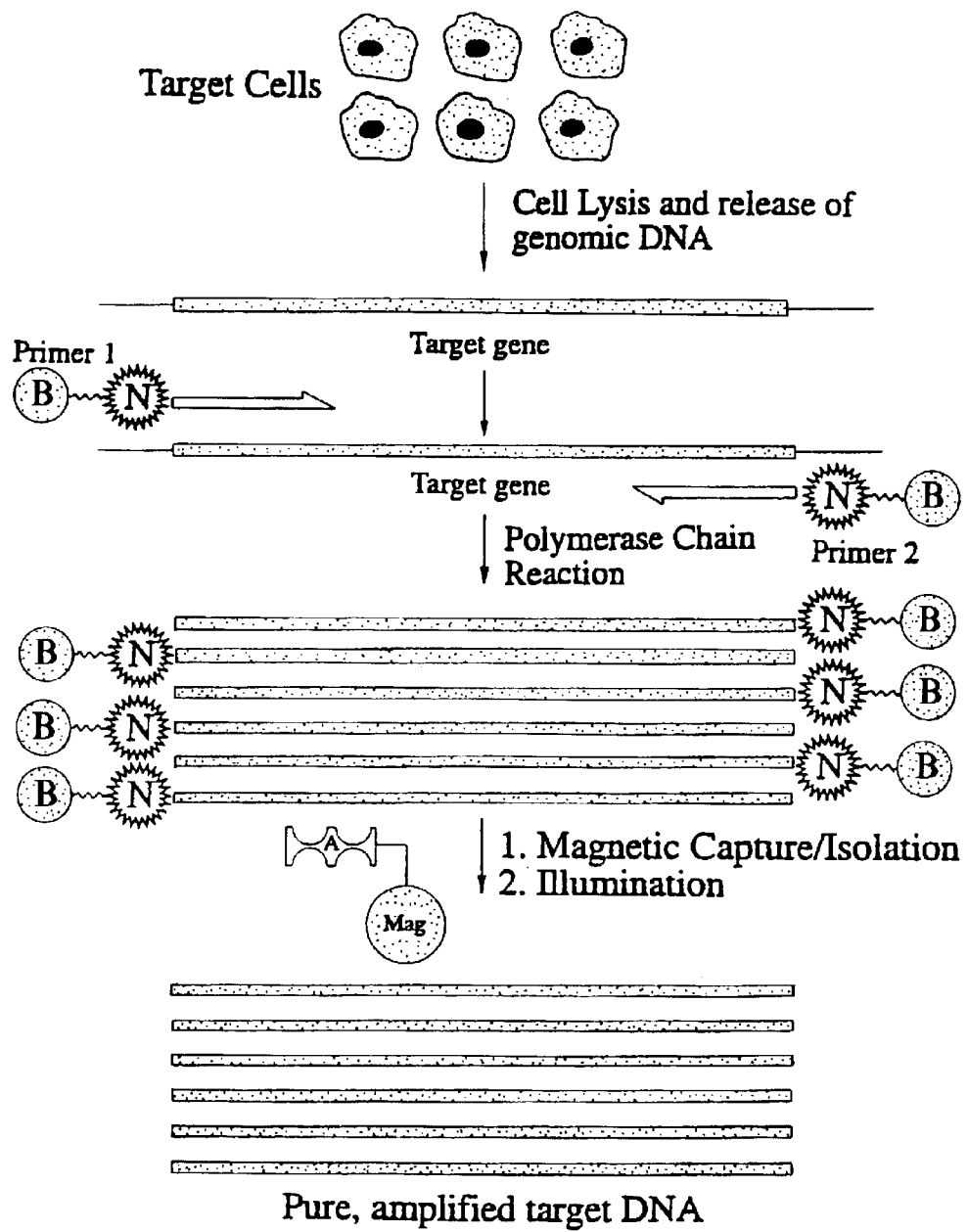
FIG. 14 Two methods (A and B) for the isolation of PCR-product using PCB.
Figure 14B:
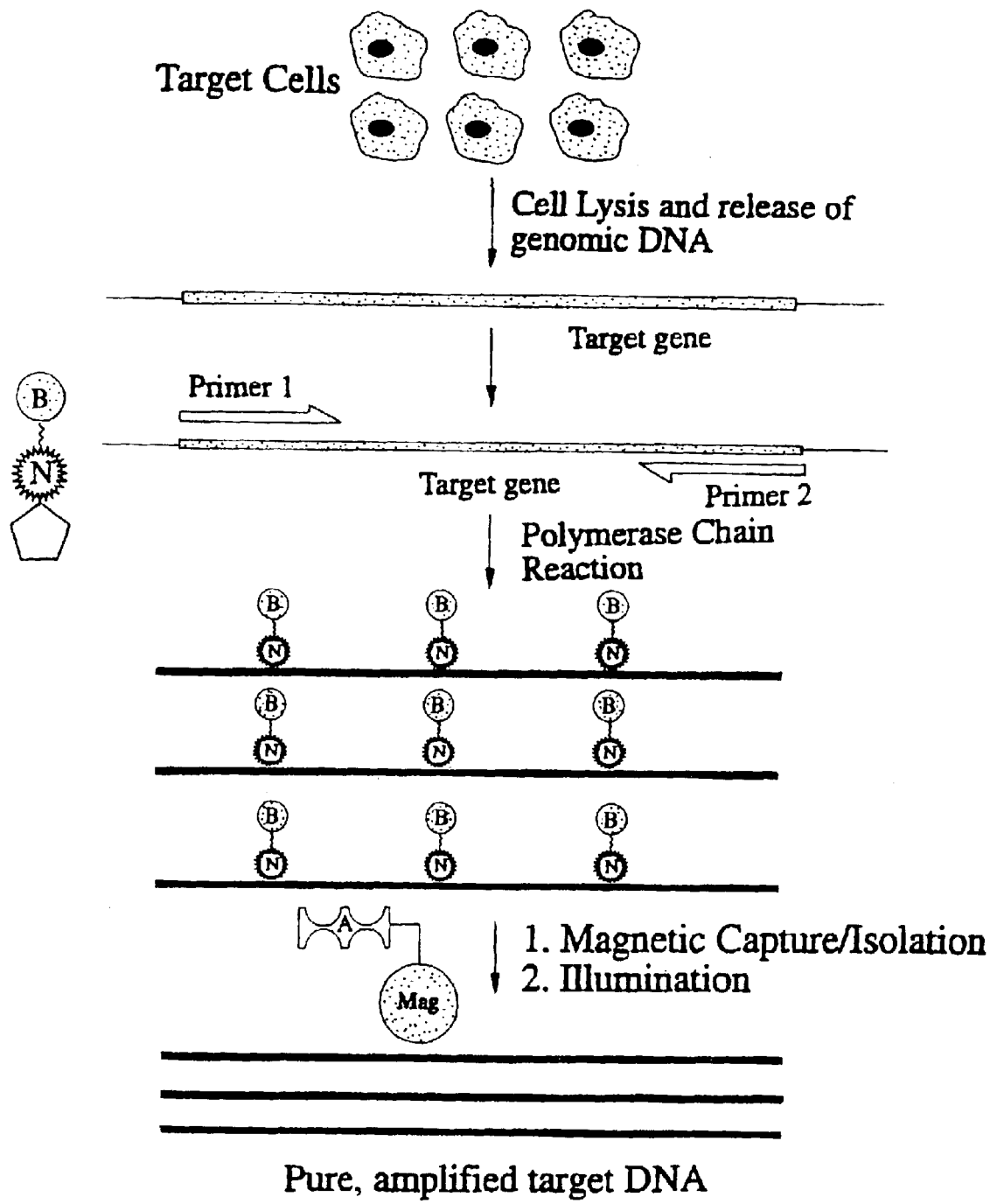

Two methods for the isolation of PCR products using PCB are represented in FIGS. 14A and 14B. In both methods, the source of the initial pool of cells from which the target DNA is to be amplified can be from a wide variety of sources including peripheral blood and biopsy tissues. After cell lysis, the crude extract of total genome is subjected to the PCR.

In method A (FIG. 14A), DNA primers are synthesized from the flanking sequences of the target DNA with photocleavable biotin incorporation at the 5' ends. For this purpose, a PCB-phosphoramidite can be introduced directly at the 5' end of the oligonucleotide primer during DNA synthesis. A set of PCR cycles is carried out using normal dNTPs. This procedure results in PCR product where the photocleavable biotin is present on the 5' end of each complementary strand. PCR products are separated from the mixture containing other components of the PCR mixture including nucleotides, enzymes, buffers by using streptavidin such as present on coated magnetic beads (e.g. Dynabeads M-280 Streptavidin) which bind the photocleavable biotin present at the 5' end of the DNA. A typical procedure to be followed is to mix 40 µl of washed Dynabeads M-280 Streptavidin with 40 µl of the PCR mixture and to incubate for 15 minutes at room temperature. The Dynabeads are then collected using magnetic means such as the DYNAL Magnetic Particle Concentrators. Residual primers will be bound to the streptavidin-binding material due to the presence of photocleavable biotin at its 5' end. A small spin column like NAP-5 (Pharmacia Biotech; Piscataway, N.J.) can be used to remove smaller molecules and primers before streptavidin-magnetic bead capture is carried out. The immobilized PCR product, now bound to streptavidin, is photolyzed to release biotin from the DNA and the unmodified PCR product recovered.

In method B (FIG. 14B), the problem of primers contamination is eliminated. DNA primers are synthesized for the flanking sequences of the target DNA without 5' biotinylation using conventional oligonucleotide synthesis. Normal dNtPs along with a small pool of PCB-dUTP are introduced into the PCR reactions. For convenience, the dNTPs and PCB-dUTP can be premixed into aliquots to be used in conjunction with PCR reactions. The PCR products are separated from the mixture containing other components of the PCR mixture including nucleotides, enzymes, buffers and primers by using streptavidin such as present on coated magnetic beads (e.g. Dynabeads M-280 Streptavidin).

The immobilized PCR product, now bound to streptavidin, is photolyzed to release biotin from the DNA and recover unmodified PCR product. Method A may sometimes be preferable when the immobilized DNA which is bound to streptavidin is to be assayed using a biotinylated probe. In this case the entire complex could be released after assay by photocleavage followed by an addition separation step, eliminating the biotinylated probe and leaving the PCR product free for further use such as for cloning. Alternatively, Method B may be preferable if release of a primer-free product is required without an intermediate assay. This would also produce a higher recovery since there are more PCB molecules per molecule of DNA.

PCR is also widely used in the detection of a variety of diseases related markers. Table 7 illustrates the various uses of PCR for detection of diseases and disorders and the potential uses of PCB-incorporated PCR in such diagnostic and forensic applications.

TABLE 7

PCR use for detection of disease related DNA/RNA

| Disease/Virus/Bacteria | Primer | Assay of the PCR product |
|---|---|---|
| HTLV-I | various targets including tax, gag or env | Liquid hybridization/Spot blot |
| HIV | targeted at the conserved regions of the virus | Oligomer Hybridization |
| Hepatitis-B Papillomaviruses | pol gene | Southern hybridization Dot-blot Restriction enzyme analysis |
| Cytomegalovirus (herpes virus group) | | Hybridization |
| Enterovirus | 100% conserved regions RNA | RT-PCR followed by hybridization |
| Gastroenteritis Cholera | | Reverse hybridization |

In a preferred embodiment of the invention, the methodology, based on PCB, for isolation and detection of PCR products can be applied to diagnostic assays of a variety of diseases, the detection of mutations as well as to the identification of unique DNA sequences. For example, serological assays such as Western blots and immunofluorescence and radioimmunoprecipitation assays provide a rapid and sensitive procedure to screen for the presence of antibodies to HIV-1. Further, in current PCR-based analysis, highly conserved regions of the viral genomes are targeted for amplification and involve hybridization using $^{32}$P-labeled oligomer probes in solution to one strand of an amplified product. These tests can be used only for the direct detection of the virus. A useful assay for the detection of HIV would detect not only active virus, but also the presence of latent virus which has not yet expressed its genome, but is still present in cells. This would allow determination of both latent and actively replicating virus. This would be particularly useful in newborns where maternal antibodies can interfere with serological tests.

In another preferred embodiment, conjugates may be used to efficiently create genomic or cDNA libraries. Construction of a PCR-directed cDNA library from total RNA may provide the only methodological approach to analyze cell-specific gene expression where the amount of biological tissue is severely restricted. This approach is particularly applicable where a specific stimulus results in the modification or differentiation of a small number of cells within a population.

Figure 15:
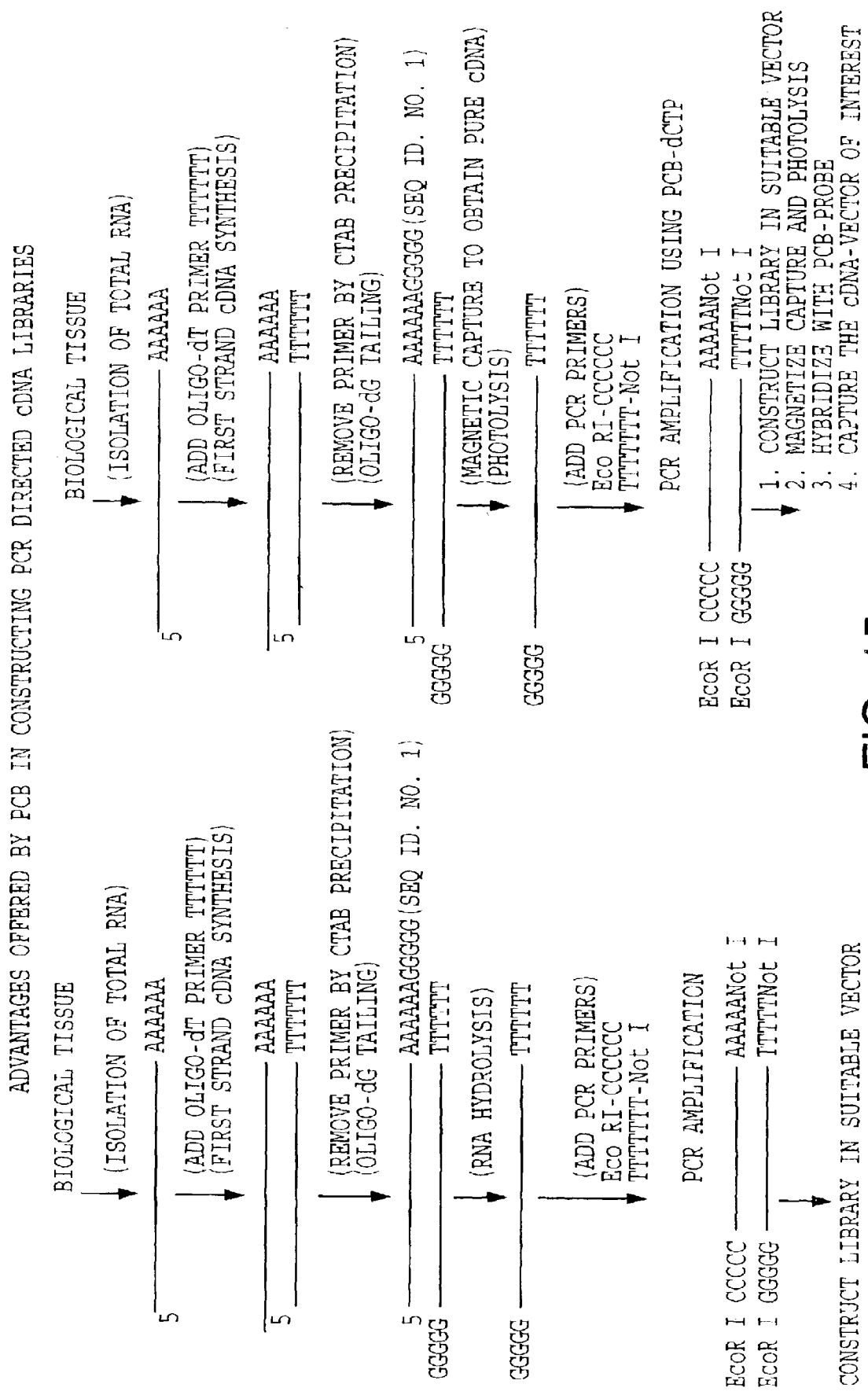
FIG. 15 Comparison of methods for the construction of a cDNA library (A) with PCB and (B) without PCB. SEQ. ID. No.: 1

Current schemes for the construction of, for example, cDNA libraries require the isolation of cellular RNA and usually further purification of mRNA from the more abundant rRNA and tRNA components. The major advantage in PCR based methods is that mRNA purification is not necessary. This is particularly advantageous where biological material is limited wherein efficient mRNA purification would be impossible. The general strategy is illustrated schematically in FIG. 15.

High quality, intact RNA is prepared using guanidinium hydrochloride procedure (S. J. Gurr et al., PCR: A Practical Approach, Oxford University Press, New York, 1991). First strand cDNA is synthesized using AMV reverse transcriptase in the presence of PCB-dCTP in 1:1 ratio with dCIP (final concentration of both should equal that of other dNTPs). This is followed by removal of oligo-dT primers which can be carried out in a rapid and quantitative manner using magnetic capture followed by illumination. Current methods use CTAB precipitation which results in loss of valuable cDNA:RNA hybrids, which is followed by homopolymer tailing using oligo-dG (A. Otsuka, Gene 13:339, 1981). After homopolymer tailing, the RNA is hydrolyzed which subjects cDNA to harsh condition such as 50 mM NaOH at 65° C. These steps are not necessary using PCB-nucleotide conjugates. Second strand synthesis and cDNA amplification is achieved by PCR in presence of PCB-nucleotides. All the PCR products are ethanol precipitated and are ligated with a suitably digested vector. These vectors are rapidly purified by using magnetic capture and illumination. These vectors can be screened using PCB-modified hybridization probes to selectively remove the vector of interest. This vector can then be magnetically captured and illuminated to obtain pure vector containing the DNA of interest.

Another aspect of the invention facilitates the process of site-directed mutagenesis. For example, cassette mutagenesis is a powerful approach in creating site directed mutants and avoids sequencing of entire genes to confirm the introduction of a mutation. Basic steps in cassette mutagenesis require construction of a vector which contains the gene of interest with well-separated, unique restriction sites. Restriction digestion of vector carrying the gene of interest using two unique restriction enzymes to remove a cassette of double-stranded DNA where the mutation is to be introduced.

The cassette containing the desired mutation is synthesized using automated oligonucleotide synthesis. The digested vector and the cassette are ligated to generate complete vector. These ligated mixtures are transformed into host cells and the colonies are screened by sequencing the cassette regions of plasmid mini-preps. Although this process is capable of rapidly and accurately generating a large number of site directed mutants as shown in case of bacteriorhodopsin (H. G. Khorana, J. Biol. Chem. 263:7439, 1988), there are several areas where time and resources can be saved using PCB.

After the initial vector restriction, the new mutant containing cassette is labeled either chemically or enzymatically with PCB. Subsequent ligation mixture is purified using streptavidin interaction, for example, magnetic capture using Dynabead-280 streptavidin. The capture results in selective isolation of recombinant vector containing the PCB-cassette and free PCB-labeled cassette. Photolysis releases the mutant containing vector in pure form in any desired solution and concentration. Subsequent transformants have very high probability of containing only the desired mutant.

In current protocols, after restriction digestion of vector, complete purification of doubly restricted vector by, for example, agarose gel electrophoresis, is often difficult. The size difference of the resulting DNA fragments is typically very small. For example, the size of a typical cassette is about 30 base-pairs (bp) and a typical vector about 5000 bp. Restriction enzyme digestion to remove the cassette would produce fragments of 5000 bp and 30 bp which can be readily distinguished and isolated. However, this is assuming that complete digestion has occurred. Partial digestion would produce an additional fragment of 5030 bp which is not easily detected much less distinguished or isolated. Thus, ineffective purification of restricted vector creates a higher chance of ligation without incorporation of the mutant cassette. Use of PCB avoids gel electrophoresis and subsequent elution of restricted fragments. Magnetic capture can be performed even in the ligation mixture.

Liposomes are widely used for targeting and introduction of biologically important materials into cells via fusion into the cell membrane (G. Gregoriadis editor, *Liposome Technology*, vol. III, CRC Press, Boca Raton, Fla., 1984). The avidin-biotin system is useful for in vitro studies to mediate between encapsulated liposomes and target cells. These studies involve the use of biotin containing phospholipids to introduce biotin into membranes (E. A. Bayer et al., Biochim. Biophys. Acta 550:464, 1979). Avidin-biotin system has also been attempted for targeting drugs into cells. These studies have determined that the effects of biotinylation on the properties of the modified lipid and biotinylated molecule, albeit chemically altered, maintains their fundamental properties. For example, the biotinylated lipid is fully extractable in organic solvents, forms liposomes and mixed liposomes, and is correctly oriented in the latter (B. Rivnay et al., Methods Enzymol. 149:119, 1987). Fatty acid components comprise the interior of the bilayer and the biotinyl head groups are exposed to the aqueous environment of the solvent. Thus, the use of biotinylated lipids for liposome preparation allows an almost irreversible binding of biotin-streptavidin interaction. Although biotin and its interaction allows easy manipulation of these liposomes, any attempt to concentrate or separate these liposomes using immobilized streptavidin, such as magnetic beads coated with streptavidin, fails as it is virtually impossible to separate the concentrated/separated liposomes from bound streptavidin.

Figure 16:
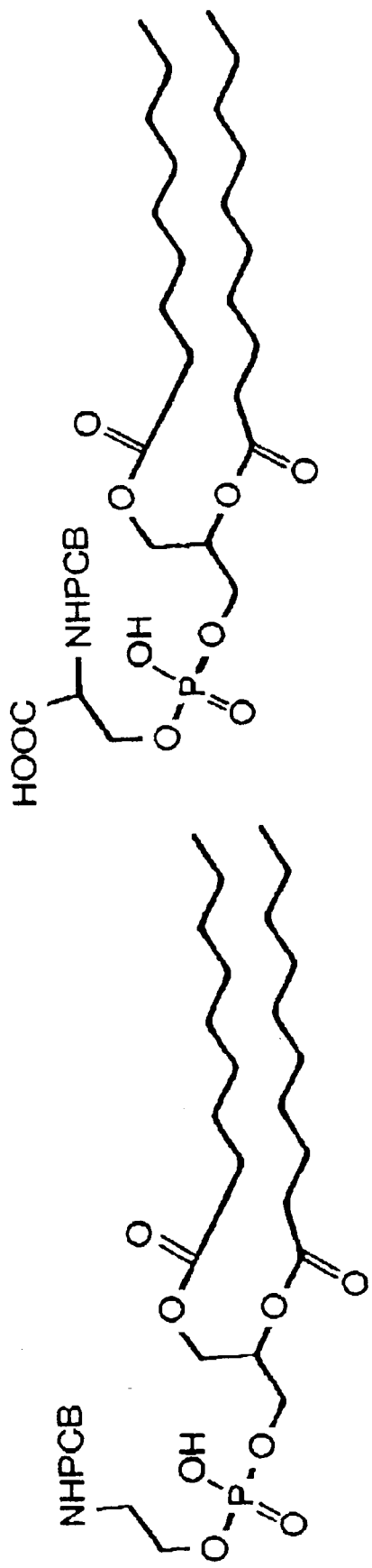
FIG. 16 PCB lipids.

Use of PCB-lipids readily overcomes these limitations as illumination releases the PCB-lipid containing liposomes into desired solutions at desired concentrations. The steps involved in the manipulations of liposomes using PCB-lipids include (1) attachment of a photocleavable biotin derivative to a liposome by chemical means or, alternatively, incorporation of a photocleavable biotin lipid (PCB-lipid) into a liposome by first derivatizing the lipid with PCB followed by preparation of liposome (PCB-liposome), (2) concentration or separation of the PCB-liposome through the selective interaction of the photocleavable biotin with avidin, streptavidin or their derivatives which is normally immobilized on a material such as magnetic beads, affinity column packing materials and filters, and (3) detachment of the photocleavable biotin from the PCB-liposome by illumination at a wavelength which causes the photocleavable biotin covalent linkage to be broken The methods for attachment of various photocleavable biotins directly to liposomes involves modification of the functional groups on the lipids molecules using PCB. The choice of a particular photocleavable biotin depends on which molecular groups are to be derivatized on the lipids constituting the liposome. For example, attachment of photocleavable biotin to a liposome could be accomplished by forming a covalent bond with the amino group on the phosphatidylserine. Although a number of group-specific PCB derivatives are available that allow modification of any functional group to yield PCB-lipid, phosphatidylethanolamine and phosphatidylserine are exemplary. PCB-phosphatidylserine and PCB-phosphatidylethanolamine are shown in FIG. 16.

Concentration and separation of liposome from a heterologous mixture is readily achieved using photocleavable biotin by established procedures that are similar to the more conventional methods utilizing non-cleavable biotin lipids. This normally involves an affinity technique based on streptavidin-biotin interaction whereby the liposomes containing biotin are immobilized due to their interaction with streptavidin. These techniques include streptavidin-coated magnetic beads, streptavidin-sepharose columns and streptavidin conjugated filters, all of which are commercially available. After concentrating PCB-liposomes using affinity interaction with streptavidin, liposomes can be released by illumination in desired solution and at the desired concentration.

Avidin-biotin technology is used extensively in the field of affinity cytochemistry where specific cell structures or subcellular components are localized by selective labeling.

Two different approaches termed immunohistochemistry (IHC) and in situ hybridization (ISH) are available. In IHC, a primary antibody or binding ligand which is biotinylated (alternatively, a biotinylated secondary antibody can be utilized), is directed at a specific antigen on the surface of a cell or cellular structure. The cell or cellular structure is then localized by application of a reporter complex which could consist of an avidin-enzyme conjugate, avidin-fluorescence marker or avidin-ferritin complex for electron microscopic localization.

In ISH, a DNA probe which is biotinylated is used to label the location of specific mRNA or DNA sequence in individual cells or tissue sections. A similar range of avidin based reporter complexes can be used as in immunohistochemistry including enzyme, fluorescence and ferritin conjugated avidins. However, a serious limitation of the conventional application of these two techniques is the difficulty of removing the biotin-marker complex once a label has been applied to sample. Removal of the label would enable additional labels to be applied thereby providing a means to map the interrelationship between various cellular and subcellular components in a tissue. The use of PCB provides a convenient means to achieve this goal since photocleavage of the linker connecting the antibody or DNA probe and PCB will result in release of the marker complex.

In situ hybridization techniques are used to detect specific cellular DNA or which are non-uniformly distributed in individual cells or tissue sections, and to detect viral nucleic acid sequences which are often focal in distribution. In contrast to Southern-, Northern- or dot-blot hybridization assays which determine the average content of target molecules per cell in the extracted tissue, ISH detects specific target sequences that are focally distributed in a small number of cells that contain significant levels of target molecules (E. J. Gowans et al., *Nucleic Acid Probes*, R. H. Symons editor, CRC Press, Boca Raton, Fla., 1989).

Current technology is limited by fact that a single tissue section, chromosome slide or cell-slide is usable only once and probing the distribution of second target which could be another set of sequences that are co-regulated or correlated, is almost impossible. PCB labeled probes offer completely non-invasive approach for multiple in situ hybridizations on such valuable sample. Combined with multiple in situ hybridizations, a composite picture can be constructed of distribution of various nucleic acids. The protocol for ISH is adapted from published procedures (D J. Brigati et al., Virol. 126:32, 1983; I. Guerin-Reverchon et al., J. Immunol. Meth. 123:167, 1989). The procedure involves careful fixation and sectioning of tissues which may be either paraffin or frozen sections. Fixation is designed not only to fix nucleic acids, but also to bind the section firmly to the slide. Glutaraldehyde is used for DNA and paraformaldehyde is used for RNA detection. Both steps include optional denaturation steps which are necessary if dsDNA or dsRNA is the target of reaction. Further steps involve preparation of different probes that are labeled using PCB, and hybridization of these probes in a sequential manner. ISH follows the same general principles as a solution and filter hybridization (R. J. Britton et al., *Nucleic Acid Hybridization*, B. D. Hames and S. J. Higgins editors, IRL Press, Oxford, 1985). PCB-labeled probe is then detected using variety techniques that use streptavidin conjugated detecting systems. A picture is obtained that shows distribution of first probe in the tissue section or chromosome picture. Photolysis results in release of detection assembly along with biotin moiety. ISH and detection is then repeated with second probe and its distribution is obtained. A composite picture is created that shows distribution of a variety of probes in the tissue section.

In situ hybridization (ISH) techniques are also used to detect either specific cellular DNA or RNA sequences at the chromosomal level in individual cells or tissue sections. The method is referred to as hybridization histochemistry. ISH is ideally suited not only to the detection of cellular nucleic acid sequences which are non-uniformly distributed in tissues or cell, but also to the detection of viral nucleic acid sequences which are often focal in distribution The detection of nucleic acid by ISH satisfies the primary objective of reflecting accurately the intercellular and intracellular distribution of target molecules in the sample. In general, ISH may be used to detect DNA corresponding to normal or abnormal genes, to identify the chromosomal location of particular DNA sequences, and to measure the level of expression of these genes by mRNA detection In particular, mRNA is a common target for in situ hybridization reaction in studies of gene expression and cell differentiation In the special cases of virus infected cells, either viral genomic nucleic acid or RNA transcripts can be detected. ISH is especially valuable where the histological mapping of target cells within a tissue is sought. In contrast, Southern, Northern and dot-blot hybridization assays measure the overall concentration of the target molecules per cell in the extracted tissue. If PCB is substituted for biotin in the application of immunochemistry and in situ hybridization, the methodology for localization of a label is almost identical. However, an important advantage is the ability to completely remove the label in the form of a PCB-avidin marker complex by simple illumination of the sample which photocleaves the PCB linkage to the antibody or hybridization probe. This step renders the sample, typically a tissue section, available for further sequential labeling by additional different probes.

There is often a need to determine if antigenic peptides, hormones or viral gene products detected intracellularly by immunohistochemical techniques represent de novo synthesis or merely deposition and passive accumulation It is also useful to determine if specific mRNA, detected by ISH is translated into protein product. The use of PCB facilitates such a determination since sequential interrogation of a single sample is possible using the same enzyme-avidin linked reporter complex. This approach avoids complications due to the use of different samples.

Many different genes, difficult or impossible to locate otherwise, can be localized using conjugates of the invention. Neurotransmitter receptors are members of large gene families. By a combination of expression strategies and homology cloning, dozens of receptor genes in this family have now been cloned. These genes include those encoding receptors for glutamate, glycine, and γ-aminobutyric acid (GABA) receptors. Cloning has revealed the existence of distinct neurotransmitter-receptors in numbers that had not been anticipated by neurophysiologists. The significance of this surprising receptor homogeneity is not yet known but ISH has shown that individual receptor subtypes are expressed in unique patterns in the brain. An important goal is to determine the distribution of these receptors in the brain. Ordinarily, this is done using many thin slices each exposed to a different hybridization probe. However, these experiments suffer from the use of multiple tissue sections. In contrast, the use of PCB would allow repeated analysis of the same rat brain section to determine complete distribution of each receptor expression.

Further, cloned genes and markers can be localized by ISH to specific regions of chromosomes. Sequences can be localized to sub-chromosomal regions by hybridizing radioactively labeled probes directly to chromosome spreads.

Chromosome spreads are made by using cells whose division has been blocked in the metaphase by a chemical like colcemid which disrupts the mitotic spindle. After fixing and staining, a pattern of light and dark bands develops on each chromosome, so that the chromosomes can be identified. After ISH, location of the radioactive probe is revealed by the distribution of silver grains in a photographic emulsion layered over the spread. However, the detection of single copies of human genes is difficult and can be done only by pooling the distribution of grains over as many as 30 or more metaphase spreads.

PCB offers the unique advantage that the probe can be photoreleased after localization of a specific genetic sequence on a chromophore and a second probe applied. In cases where too closely spaced sequences are to be detected, prior removal of the probe may be essential in order to avoid interference from the original probe. In addition, the method allows for the use of a large number of probes to be applied sequentially and is not limited by the availability of different marker complexes which can be simultaneously measured. This technique could also be used advantageously for rapid ordering of multiple probes on a chromosome.

An important application of biotin-avidin technology is the separation of cells from a complex mixture often containing a variety of different cell types. Cells which can be utilized include cells within a biological sample, tissue culture cells, bacterial cells and diseased cells. Cells may be mammalian, such as mammalian stem or fetal cells. Receptors include antibodies directed against the classical cell surface receptors and other surface proteins, but also any cell-surface molecule that has a specific affinity for another molecule. Preferably, the receptor is an antibody which recognizes a cell surface marker on the target cell or a specific protein which recognizes a cell surface ligand or other macromolecule on the target cell. PCB-modified antibodies, specific for surface antigens, receptors or ligands on the cell, can be used for cell separation or cell sorting with, for example, an apparatus such as a fluorescence-activated cell sorter (FACS). These PCB-antibodies, when linked to streptavidin-coated magnetic beads can bind to the specific cell population bearing a particular antigen and can then be separated using ImmunoMagnetic Separation (IMS).

Current methodologies do not allow gentle separation of these magnetic particles from separated or sorted cell population. PCB modified antibodies, however, can be readily separated from magnetic particle after illumination. IMS involving PCB-antibodies can be used in cell-sorting, tissue typing and for selective enrichment of microorganisms using modifications of protocols described earlier (A. Elbe, J. Immunol. 149:1694, 1992; S. Qin, Sci. 259:974, 1993; L. Leclerecq, Immunol. Lett. 28:135, 1991).

In conventional methods, a biotinylated antibody is utilized which binds selectively to an antigen residing only on the target cell. The target cells can then be isolated from the mixture by using streptavidin-coated magnetic beads or streptavidin based affinity columns. The affinity material sometimes contains a secondary antibody directed toward the primary antibody. A severe limitation of this approach is the difficulty of releasing the cells once they are bound to the affinity medium through the biotin-streptavidin interaction. Normal methods that are designed to disrupt the biotin-streptavidin interaction or the antibody-antigen interaction can reduce the overall viability of the released cells. This is a serious disadvantage if the cells are to be used later for culturing or transplantation. Similarly, conditions such as low pH that disrupt the antibody-antigen interaction can cause cell damage. A standard technique is overnight incubation in a culture medium followed by vigorous mixing. This causes shedding of the antigen involved in binding. However, this method is time consuming, can lead to cell degradation and does not result in complete release. An alternate method is to disrupt the antibody-antigen interaction with enzymatic treatment, which can also be damaging to a cell. An additional method is the utilization of anti-FAB antibodies to compete for the antigen. Such methods are time consuming, expensive due to the use of antibodies and only partially effective. These methods of detachment (release) of cells are all particularly ineffective when the antibody-antigen interaction is strong or the binding involves several antigen-antibody interactions mixing. Conventional biotins which can be chemically cleaved such as NHS-SS-Biotin (sulfosuccinimidyl 2-(biotinamido) ethyl-1, 3-dithiopropionate; Pierce Chemical; Rockford, Ill.) pose serious problems since the cleavage medium consisting of a high concentration of reducing agents such as thiols will cause reduction of protein disulfide bonds and a subsequent loss of cell viability.

In contrast to conventional methods, photocleavable biotin offers an inexpensive, effective and rapid means to release immobilized cells simply by using light exposure. Release occurs due to photocleavage of the covalent linkage between the antibody and biotin. While the antibody still remains bound on the released cell, this is normally not a problem for cell integrity or additional utilization of the separated cells. Since photocleavage can be performed in short periods and results in almost full removal of the photocleavable biotin release is rapid and complete.

Further, using photocleavable conjugates, cells which represent a very small populations of sample of cells can be accurately and efficiently selected. This enables methods such as the selection of immune cells, stem cells, fetal cells, precursor cells and nearly and cell type from lymph (e.g. interstitial, lymphatic), blood (e.g. arterial and peripheral blood) or tissue (organ, soft tissues, muscle) samples. Selected and isolated cells can then be cultured in very large numbers and possible reintroduced into the same or another patient. Cultured cells can also be used in gene therapy by the introduction of genetic material into cultured cells. Such techniques are not possible using conventional detection and isolation procedures.

The same approach can also be used by linking photocleavable biotin to other cell specific macromolecules such as cell-associated ligands or antigens. For example, B cells expressing a specific immunoglobulin receptor for a target antigen could be isolated by attaching photocleavable biotin to the target antigen and then binding it to a streptavidin-coated bead. Alternatively hybridoma screening and stem cell selection could be performed using this approach.

Figure 17:
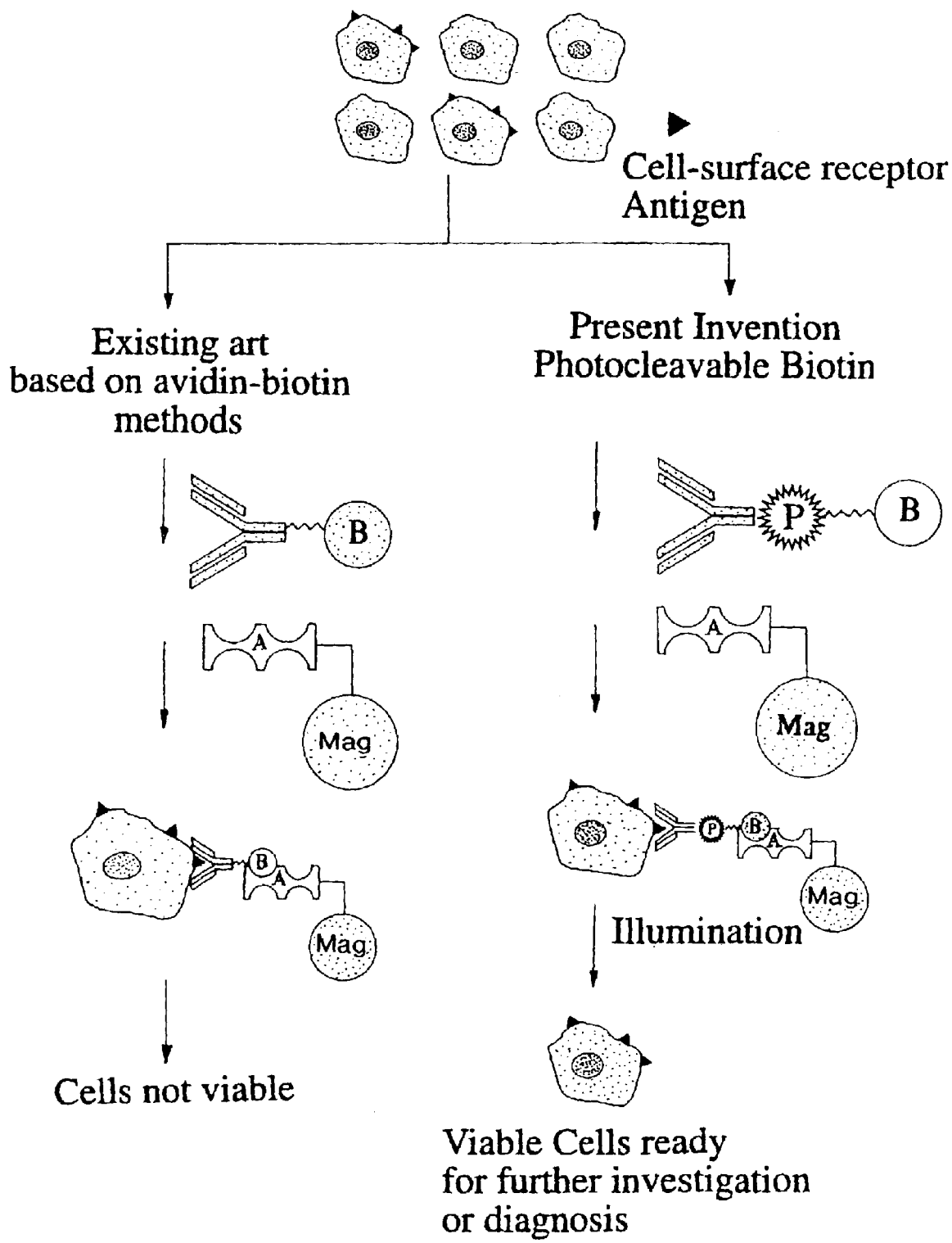
FIG. 17 Immunoselective cell separation using PCB.

The three basic steps involved in cell isolation using PCB are (1) attachment of a photocleavable biotin, or molecule containing a photocleavable biotin derivative including (antibodies, receptor ligands, antigen) to the surface of the target cell by a photochemically cleavable bond, (2) separation of said cell type from other cells and materials in the complex mixture through the selective interaction of the photocleavable biotin with avidin, streptavidin or their derivatives, and (3) detachment of the photocleavable biotin from the said cell type by illumination at a wavelength which causes the photocleavable biotin covalent linkage to be broken. These steps, using PCB, can be carried out in combination with ordinary biotin. In this case, cells containing two or more surface markers can be from those containing only one. Each of these steps is illustrated in FIG. 17.

Several applications for the use of PCB for cell separation offers clear advantages over existing technology. A common method for isolation of cells is to label the cell with a fluorescent dye which is directed to the target cell through an antibody-fluorescent conjugate. The cells can than be separated by using a fluorescence-activated cell sorting device and used for a variety of purposes including cell typing, hybridoma production and tissue culturing. However, with this technique the separated cells remain labeled with the fluorescent dye. This can result in reduction in cell viability, prevent their use in therapeutic applications where the dye can be toxic, and prevent further fluorescence based sorting into subspecies of cells. One example would be the separation of lymphocytes using characteristic antigens such as CD2, CD4, CD8 and CD19 followed by sorting into subspecies.

An alternative approach is to utilize an antibody which is conjugated to PCB. In this case the cell can be fluorescence labeled with an avidin-fluorescein complex which is commercially available in a variety of forms (Table 8). The fluorescent label can then be removed by photocleavage of the PCB which results in release of the PCB-avidin-fluorescent complex. A variety of fluorescent labels exist which absorb in a region outside of the absorption band of the PCB, thus avoiding photocleavage during the cell sorting.

TABLE 8

Commercially Available Avidin-Florescent Dye Complexes

| Conjugate | Absorption (nm) | Emission | Producer |
|---|---|---|---|
| Avidin-Fluorescein | 490 | 520 | Pierce |
| Avidin-R-Phycoerythrin | 450–470 | 574 | Pierce |
| Avidin-Rhodamine | 515–520 | 575 | Pierce |
| Avidin-Rhodamine 600 | 575 | 600 | Pierce |
| Avidin-Texas Red | 595 | 615 | Pierce |

Another example of the utility of PCB methodology for cell isolation is the isolation of B cells for hybridoma production Briefly, formation of hybridomas for the purpose of monoclonal antibody production involves the fusion of myeloma cells with lymphocyte B cells. Generally, a heterogeneous population of B cells is utilized which contains different immunoglobulin receptors. The hybridoma which expresses the desired antibody is then screened by assaying for binding to a particular antigen. This screening process can be time-consuming and expensive. Screening could be avoided if a method existed for isolation of a particular population of B cells which only expressed the desired immunoglobulin receptor. In principle, this could be accomplished by using a biotinylated antigen, such as a polypeptide with a specific sequence, which will only bind to those B cells which express the specific immunoglobulin receptors for the antigen. This subpopulation of B cells could then be selected by using avidin affinity techniques such avidin-coated magnetic beads. However, the subsequent step of hybridoma formation will still be prevented unless the B cells can be released from the avidin-biotin complex in a viable form.

The use of PCB-biotin avoids this problem by providing a simple method for releasing the B cells in a viable form after immobilization by the biotin-avidin interaction. Photocleavage of the photocleavable biotin linkage with the antibody results in the release of the B-cells and the bound antigen which is now in an unmodified form Since no chemical treatment is required, the cells will retain their viability for further fusion to the myeloma cells. Furthermore, the method is rapid and suitable for automation.

Another embodiment of the invention is directed to targets isolated by the above method which may be utilized in pharmaceutical compositions to treat or prevent diseases and disorders. Pharmaceutical compositions may comprise the isolated targets plus a pharmaceutically acceptable carrier such as water, oils, lipids, saccharides, polysaccharides, glycerols, collagens or combinations of these components. The composition is administered to patients for the treatment or prevention of certain diseases and disorders and for the site-directed administration of pharmaceutical agents.

Another embodiment of the invention is directed to a method for determining an in vivo half-life of a pharmaceutical in a patient. Conjugates are formed by coupling the pharmaceutical to a bioreactive agent via a covalent bond that can be selectively cleaved with electromagnetic radiation. Conjugates are administered to the patient after which, two or more biological samples are removed. Samples are treated with electromagnetic radiation to release the pharmaceutical from the bioreactive agent, the amount of the bioreactive agent in the biological samples is determined, and the in vivo half-life of the pharmaceutical determined.

The pharmaceutical may be a composition comprising cytokines, immune system modulators, agents of the hematopoietic system, chemotherapeutic agents, radio-isotopes, antigens, anti-neoplastic agents, recombinant proteins, enzymes, PCR products, nucleic acids, hormones, vaccines, haptens, toxins, antibiotics, nascent proteins, synthetic and recombinant pharmaceuticals, and derivatives and combinations of these components. Conjugates may be administered to patients by parenteral administration, sublingual administration, enteral administration, pulmonary absorption, topical application and combinations thereof. Animals which can be tested include mammals such as humans, cattle, pigs, sheep, dogs, cats, horses and rodents. Biological samples which are collected can be sample of peripheral blood, blood plasma, serum, cerebrospinal fluid, lymph, urine, stool, ophthalmic fluids, organs and bodily tissues.

Another embodiment of the invention is directed to the controlled release of a substrate into a medium. Conjugates comprised of a bioreactive agent coupled to the substrate by a covalent bond which can be selectively cleaved with electromagnetic radiation are created as described. These conjugates are bound to a surface of an article and placed into the medium The surface of the article is exposed to a measured amount of electromagnetic radiation and the substrate released into the medium to carry out a beneficial effect. Alternatively, an article may be placed at a selected site and the conjugates, having an affinity for the article, are administered at a distal site. Conjugates then migrate to the selected site and perform an intended function. After completion of that function, radiation is applied and the substrate is released from the fixed bioreactive agents. Released substrate may be naturally eliminated from the patient's system. This can be highly useful, for example, in radiation therapy for cancer patients.

Preferred are radiation wavelengths which can penetrate the medium. Depending on the amount and frequency of radiation exposure, release can be controlled and continued over a period of time. This method is useful for the controlled and site-directed administration of pharmaceutical compositions to a patient. In such cases, the medium in which the article is placed may be blood, lymph, interstitial fluid or a tissue. Controlled release may also be performed in tissue culture for administering a constant or periodic amount of a substrate to a cell culture fluid or balanced salt solution for uptake by the cells. Articles which may be coupled with substrate and placed within or adjacent to a patient's body include articles comprising carbohydrates, lipids, proteins, polysaccharides, cellulose, metals including magnets, organic polymers and combinations thereof. Preferably, the surface of the article is coated with streptavidin and the bioreactive agent is photocleavable biotin.

Alternatively, articles containing conjugates or agents can be placed into the site of the disorder, such as a tumor. The pharmaceutical agent such as, for example, a radioactive agent is administered to the patient and becomes bound to the fixed conjugates or agents. Effects attributable to the pharmaceutical agent are localized. The article is exposed to a measured amount of electromagnetic radiation and the pharmaceutical agents released into the body and excreted. This method is preferred when only a short term exposure of the pharmaceutical agent is desired or to efficiently remove potentially harmful agents after they have had their desired effects.

Another embodiment of the invention is directed to a method for creating a photocleavable oligonucleotide. A bioreactive agent is created comprised of a photoreactive moiety coupled to a detectable moiety and containing a phosphoramidite. The oligonucleotide is synthesized using conventional phosphoramidite chemistry. The nucleotide precursors comprise one or more photocleavable phosphoramidites such as purine-phosphoramidites (uracil, cytosine, thymine) or pyrimidine-phosphoramidites (adenine, guanine) as the ribose or deoxyribose forms, or derivatives thereof This method can be performed manually or automated using a commercially available oligonucleotide synthesizer. Photocleavable oligonucleotides can be utilized as primers or probes, in diagnostic kits and in every instance in which a nucleic acid can be used.

Another embodiment of the invention is directed to a method for detecting a target molecule in a heterologous mixture. Conjugates are formed by coupling a substrate to a bioreactive agent with a covalent bond that is selectively cleavable with electromagnetic radiation Conjugates are contacted with the heterologous mixture to couple substrate to one or more target molecules. Uncoupled conjugates are removed and the coupled conjugate are treated with electromagnetic radiation to release the detectable moiety. Presence of target molecules can be detected by detecting the presence of the released detectable moiety. Target macromolecules may be proteins, peptides, nucleic acids, lipids, polysaccharides, metallic compounds, virus, bacteria, eukaryotic cells, parasites and derivatives and combinations thereof. Once detected, target macromolecules can be isolated and the amount isolated quantitated by current any of the techniques available to those of ordinary skill in the art.

A specific application of streptavidin-biotin technology is in the detection of targets in medical diagnosis. Generally, the target is a biotinylated molecule or a biotinylated probe for the target molecule. The interaction of streptavidin with the biotinylated target or probe is amplified by an enzyme conjugated to streptavidin which catalyzes a chromogenic reaction. For example, a variety of enzymes conjugated to streptavidin are commercially available including horseradish peroxidase, β-galactosidase, glucose oxidase and alkaline phosphate. Each of these enzymes catalyze a chromogenic reaction. Additional methods of detection include conjugating streptavidin to fluorescent, chemi-fluorescent, radioactive or electron dense molecules.

An example of biotin-avidin interaction in medical diagnosis also forms the basis for a wide array of enzyme-linked immunospecific assays (ELISA). In this case, an antibody specific for the target molecule, the primary antibody, or a secondary antibody directed against the primary antibody is biotinylated. Detection is accomplished with a streptavidin-enzyme conjugate as described. A large number of immunoassays have been developed based on this approach. However, multiple immunoassays on the same sample are not easily accomplished using conventional technology since there exists no simple method of removing the avidin-enzyme-complex once bound to a biotin derivative without damaging the sample. In contrast to traditional methodologies, PCB can be reused many times for multiple assays of the same sample for multiple screening of pathogens and other markers of human diseases.

The biotin-avidin interaction also forms the basis of sensitive methods for detecting specific nucleic acid sequences such as screening human DNA samples. DNA or RNA probes which hybridize to a target DNA sequence are biotinylated. DNA containing the target sequence is detected with an streptavidin-enzyme conjugate. This method is used in conjunction with the polymerase chain reaction where the target gene or sequence to be screened is first amplified using specific primers. The introduction of biotin nucleotides into the primer or directly into the nascent PCR product using biotinylated nucleotides facilities isolation of the target DNA. A variety of biotinylated nucleotides such as biotin-dUTP are available for such purposes. However, this method has at least two limitations.

First, the presence of biotin in the amplified target DNA prevents the use of biotinylated probes without prior removal of the biotinylation. The presence of endogenous biotin or biotin-containing molecules in the sample also lowers the sensitivity of this assay. Second, the presence of biotin in the target DNA lowers hybridization efficiency and hence the sensitivity of the assay. As discussed above, the use of PCB derivatives such as PCB-nucleotides effectively eliminates these problems by allowing for complete removal of biotin from the procedure.

Conjugates and methods of the invention can be used in conjunction with a variety of diagnostic assay involving nascent protein detection. For example, diagnostic assays for cancer have been developed which rely on in vitro expression of PCR amplified genes followed by examination of the nascent protein product using gel electrophoresis (S. M. Powell et al., N. Engl. J. Med. 329:1982, 1993). The isolation of such proteins and the subsequent sensitivity of such tests could be increased by the incorporation of PCB amino acids.

Biotin-streptavidin technology is widely used as the basis for non-radioactive ELISA including diagnostic assays for specific indicators of diseases and disorders such as disease-linked antigens including adenovirus antigen (K Mortensson-Egnund et al., J. Virol. Methods 14:57, 1986), bovine leukemia virus (E. N. Esteban et al., Cancer Res. 45:3231, 1985), flavivirus (E. A. Gould et al., J. Virol. Methods 11:41, 1985), Hepatitis B surface antigen (C. Kendall et al., J. Immol. Methods 56:329, 1983), Herpes simplex virus antigen (K. Adler-Strorthz et al., J. Clin. Microbiol. 18:1329, 1983), respiratory syncytial virus (A. Hornsleth et al., J. Med. Virol. 18:113, 1986), bacterial antigens (R. H. Yolken et al., J. Immunol. Methods 56:319, 1983) and melanoma-associated antigens (human) (AC. Morgan et al., Cancer Res. 43:3155, 1983). The usefulness of these assays can be compromised if endogenous biotin is present in the sample. In this case, a false background will be obtained since the streptavidin-reporter enzyme complex will react both to non-specific biotins and to the biotinylated antibodies directed against the target protein. While several approaches to eliminate background due to non-specific binding of the avidin or streptavidin to non-biotinylated targets including the use of high ionic-strength. buffers (C. J. P. Jones et al., Histochem. J. 19:264, 1987), milk proteins (R. C. Duhamel et al., J. Histochem. Cytochem. 33:711, 1985) and lysozyme (E. A. Bayer et al., Anal. Biochem. 163:204, 1987) and altered streptavidins such as Immu-noPure NeutrAvidin (Pierce Chemical; Rockford, Ill.), none has been very effective in eliminating background due to endogenous biotin.

Figure 19:
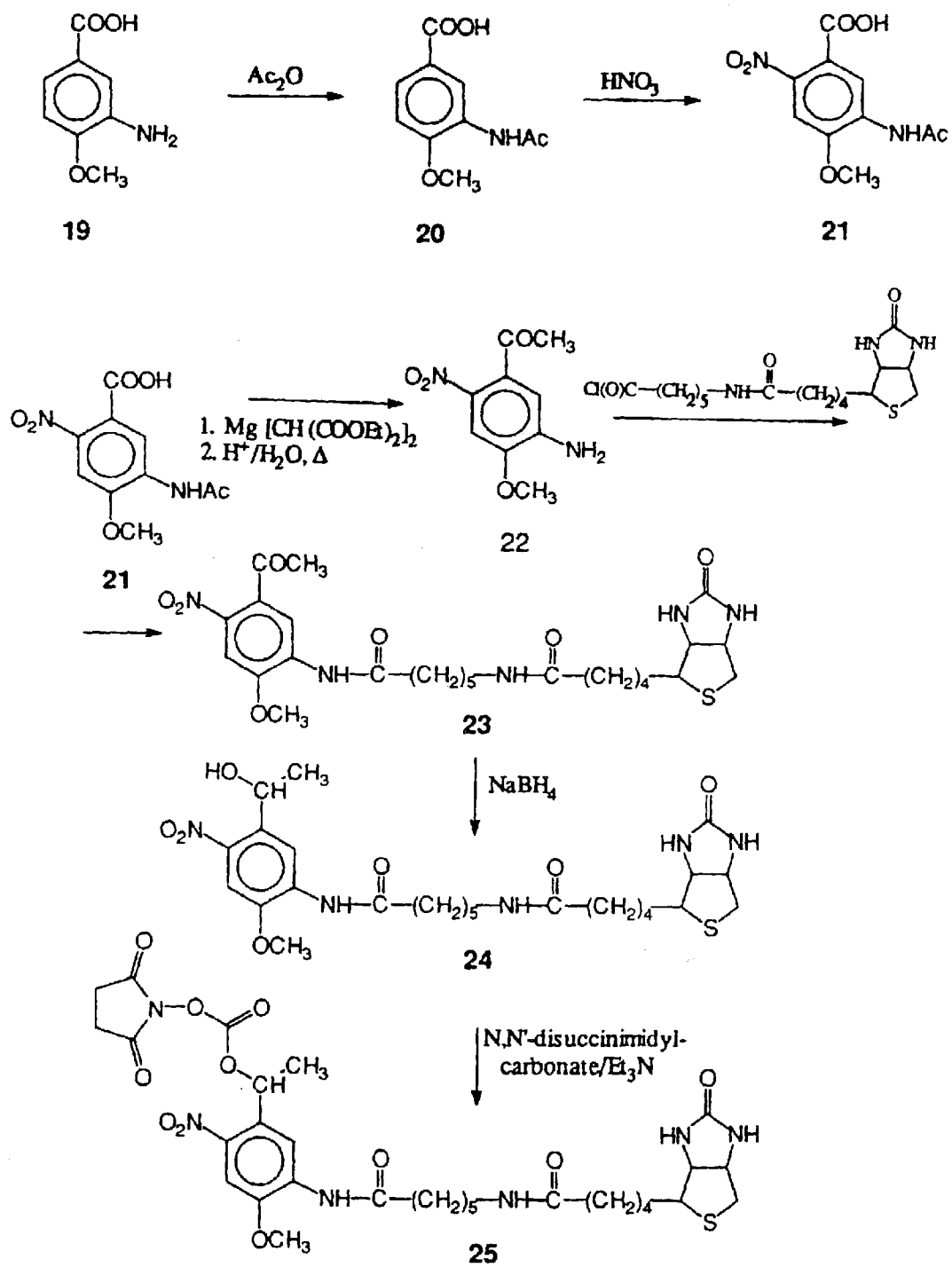
FIG. 19 Synthesis of photocleavable biotin-NHS ester, compound 25.

Use of photocleavable biotins in conjunction with immunoassays alleviates the problem by providing a means of determining the background level of non-specific biotin. The ELISA assay is first performed using conventional methodology except that the antibody directed against the protein is targeted with photocleavable biotin (FIG. 19). The streptavidin-reporter enzyme complex linked to the probe antibody system is then removed via light cleavage of the photocleavable biotin. Cleavage does not release the reporter enzyme-avidin complex bound from non-specific bound biotin since this biotin is non-cleavable. The signal obtained from the remaining biotin can be used as a measure of the endogenous biotin present in the sample and subtracted from the primary signal obtained in step 1.

Background signal due to endogenous biotin in a biotin-avidin based ELISA can be simply detected using photocleavable biotin. The ELISA is performed according to normal procedures using streptavidin-reporter enzyme complex. However, the streptavidin-reporter enzyme complex is then removed with light and the system reassayed to determine the background level of endogenous biotin.

Figure 20:
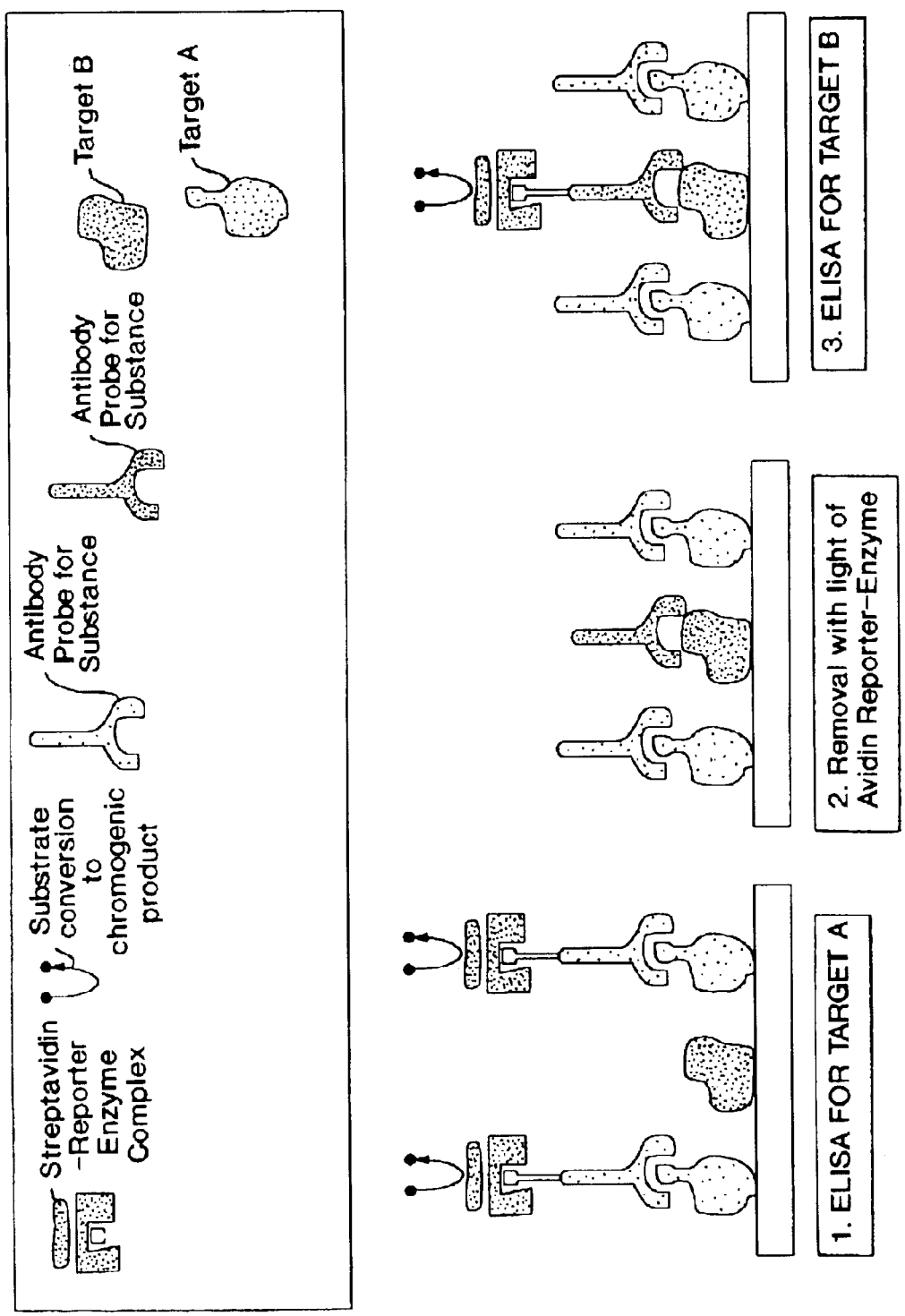
FIG. 20 Method for sequential ELISA using PCB.

A second application of photocleavable biotins is its use to conduct multiple biotin based ELISA assays on the same sample. This. is based on the ability to fully remove the streptavidin-reporter enzyme complex with light upon photocleavage of the PCB linkage. In this case a second ELISA can-be performed using a different antibody probe and reporter enzyme complex without interference from the first ELISA as shown in FIG. 20. Normally such a multiple ELISA is not possible because the signal obtained from a second antibody probe combined with a streptavidin-reporter enzyme complex cannot be easily separated from the original signal.

For example, in a conventional biotin-avidin ELISA, the streptavidin-reporter enzyme complex remains bound to the probe antibody even after the chromogenic product of the reporter enzyme is removed. Thus, it will continue to produce a chromogenic product even after a second ELISA is performed and interfere with the signal of that second immunoassay. In contrast, the removal of the streptavidin-enzyme complex by cleavage of the photocleavable biotin with light and then subsequent washes eliminates this problem since the original reporter enzyme is no longer present.

In another application of the invention, detection of pathogens such as microorganisms from biological material often requires their isolation and culturing. The more effective the isolation step, the more reliable and rapid the culturing step will be because of the elimination of other contaminants and the concentration of the target pathogen. While a variety of affinity techniques exists for separation of microorganisms such as magnetic beads conjugated to selective antibodies, the problem of release of the microorganisms in a viable form suitable for culturing and sensitive detection still remains. In contrast, PCB which is linked to the antibody or binding ligand provides a non-damaging and rapid means for photochemical release of the microorganism in a viable form.

For example, this application of the invention provides the basis for development of rapid diagnostic assays for a variety of pathogens involved in human and animal disease that were previously not possible using conventional biotin-streptavidin technology. Microorganisms could also be isolated from food, milk, soil and other materials for the purpose of depletion or detection using this approach.

Another embodiment of the invention is directed to methods for treating a disorder by the controlled release of a therapeutic agent at a selected site. Conjugates are formed by binding a bioreactive agent to a therapeutic agent with a bond that is selectively cleavable with electromagnetic radiation, wherein the bioreactive agent is comprised of a directable moiety bonded to a photoreactive moiety and the directable moiety has an affinity for the selected site. Conjugates are administered to a patient having the disorder and the selected site is subjected to a measured amount of electromagnetic radiation for the controlled release of the therapeutic agent to treat the disorder. Disorders which can be detected include infections, such as bacterial infections, viral infections and parasitic infections, neoplasias such as a tumor, and genetic disorders such as an overproduction or deficiency of an enzyme or other genetic product.

The therapeutic agents may be toxins, immune system modulators, hematopoietic agents, proteins, nucleic acids, substrate analogs transcription and translation factors, antigens and combinations thereof. Directable moieties may be antibodies such as a monoclonal or polyclonal antibody or antibody fragment.

Another embodiment of the invention is directed to diagnostic kits for detecting or screening for diseases and disorders in patients. Kits contain a conjugate comprised of a bioreactive agent, covalently bonded to a diagnostic agent having an affinity for an indicator of said disorder in a biological sample obtained from the patient. The indicator may be a presence or absence or an increased or decreased amount or level of a characteristic marker of the disorder such as an antigen or antibody, a cytokine, a specific cell type (e.g. B cells; cytotoxic, suppressor or helper T cells; macrophages; stem cells), a particular enzyme, nucleic acid or protein. Disorders which can be detected include infections, neoplasias and genetic disorders. Infections which can be detected include bacterial infections, viral infections and parasitic infections. Neoplasias which can be detected include tumors. Genetic disorders which can be detected include an overproduction or deficiency of an enzyme. Biological samples which can be added to the sample include samples of peripheral blood, blood plasma, serum, cerebrospinal fluid, lymph, urine, stool, ophthalmic fluids, organs and bodily tissues. Such kits may also be used to detect or screen for the presence of fetal or stem cells in a biological sample which can be isolated and cultured or further analyzed.

Kits may also be used to detect the presence of multiple nucleic acids and/or proteins on, for example, an electroblot using a series of secondary probes linked to biotin. After each probe is introduced, the biotin attachment could be cleaved allowing the enzymatic assay complex to be removed thus providing for a new secondary probe to be introduced. Such an approach would be extremely useful as the basis of medical diagnostic assays, where multiple antigens or nucleic acid sequences needed to be probed rapidly and automatically.

The kit may also be a nucleic acid mutagenesis kit for use in molecular biological applications such as introducing or correcting mutations in DNA or RNA. The nucleic acid may be an oligonucleotide for use in PCR or cassette-type applications. Such oligonucleotides may be single-stranded or double-stranded and preferably contain one or more restriction enzyme recognition sequences internally and ligatable 5' and 3' ends which also contain part of a restriction enzyme recognition site. Alternatively, one or more ends may be blocked to facilitate directed coupling.

The following examples are offered to illustrate various embodiments of the invention, but should not be viewed as limiting the scope of the invention.

EXAMPLES

Example 1

Synthesis of Photocleavable Agents

Five grams or 27.6 mmol of 5-methyl-2-nitrobenzoic acid (FIG. 5, compound "6"; Aldrich Chemical; Milwaukee, Wis.) was added in small portions to 10 ml (16.4 g or 148 mmol) of thionyl chloride with stirring. The mixture was stirred at room temperature for 10 hours. Excess of thionyl chloride was removed by vacuum to give the acid chloride ("7"). Magnesium turnings (1.07 g or 44.2 mmol), absolute ethanol (6 ml), chlorobenzene (8 ml), and 0.1 ml of dry $CCl_4$, were refluxed until most of the magnesium reacted. A solution of diethyl malonate (4.82 g or mmol) in 10 ml of chlorobenzene was added followed by the addition of the acid chloride (5.49 g) in 10 ml of chlorobenzene. The reaction mixture stirred for 1 hour and 1.7 ml of concentrated $H_2SO_4$ in 17 ml of $H_2O$ was added, stirred for additional 15 minutes. 20 ml of chloroform was added and the layers separated. The aqueous layer was extracted three times with 10 ml and the extracts were combined, dried and evaporated to dryness. Residue was dissolved in 8.25 mls of acetic acid. 5.4 ml of $H_2O$ and 1 ml of concentrated $H_2SO_4$ were added, the mixture was refluxed for 6 hours, neutralized with aqueous $Na_2CO_3$ and extracted three times with 20 ml of $CHCl_3$. Extracts were combined, dried and solvents removed by vacuum. Residue was crystallized from 70% ethanol to produce 4.46 g, or about 81%, of 5-methyl-2-nitroacetophenone. 5-methyl-2-nitroacetophenone (3.51 g or 19.6 mmol), N-bromosuccinimide (3.66 g or 20.6 mmol), and benzoyl peroxide (46 mg or 0.01 eq) were refluxed in 20 ml of $CCl$, for 5 hours. The reaction mixture was filtered, the filtrate concentrated and crystallized from $CCl_4$ to produce 3.64 g (72%) of 5-bromomethyl-2-nitroacetophenone ("8"). Compound 8 (2.0 g or 7.75 mmol) was added to a solution of hexamethylenetetramine (1.14 g or 8.13 mmol) in 15 ml of chlorobenzene. The mixture was stirred overnight, the precipitate filtered off and washed with 10 mls of chlorobenzene and 20 mls of diethyl ether. The precipitate (2.93 g or 736 mmol) was suspended in 35 ml of 95% ethanol followed by the addition of concentrated HCl (3.12 ml or 5 eq.). The mixture was stirred overnight and evaporated to dryness. Ten mls of DMF were added to the residue followed by the addition of a 6-biotinamidocaproic acid (3.29 g or 1.25 eq.) in 35 ml of N-methylpyrrolidone, dicyclohexylcarbodiimide (228 g or 1.5 eq.), and triethylamine (1.28 ml or 1.25 eq.). The solution was stirred overnight at room temperature, the precipitate filtered off, and filtrate precipitated to 700 ml of diethyl ether. The precipitate was dried and purified on a silica gel column using step gradient (5–20%) of MeOH in $CHCl_3$ to produce 2.27 g (about 58%) of compound 11.

Compound 11 (1 g or 1.87 mmol) was dissolved in 15 ml of 70% EtOH (FIG. 5). The solution was cooled to 0° C. and sodium borohydride (141 mg or 4 eq.) added. The solution was stirred at 0° C. for 30 minutes and at room temperature for an additional 2 hours. The reaction was quenched with the addition of 1 ml acetone, neutralized with 0.1N HCl, concentrated, the supernatant discarded, the residue washed with water and dried to produce 0.71 g (about 71%) of compound 12.

Compound 12 (1.07 g or 2 mmol) was dissolved in 10 ml DMF. N,N'-disuccinimidyl carbonate (Fluka Chemical; Ronkonkoma, N.Y.) (1 g, 1.5 eq.) was added followed by 0.081 ml or 3 eq. of triethylamine (FIG. 5). After 5 hours at room temperature, solvents were evaporated to dryness and the residue was washed consecutively with 0.1N $NaHCO_3$, water, dioxane, diethyl ether and dried to give 1.04 g (about 69%) of 5-(5-biotinamidocaproamidomethyl)-1-(2-nitro) phenylethyl-N-hydroxysuccinimidyl carbonate (PCB-NHS) ester (compound 13). M.P.=113–114° C. (uncorrected); CI-MS ($M^+$=676.5); UV-VIS$\lambda$=204 nm, $\epsilon1$=19190 $M^{-1}$ $cm^{-1}$; $\lambda2$=272 nm, $\epsilon2$=6350 $M^{-1}$ $cm^{-1}$ in phosphate buffer, pH=7.4. $^1H$ NMR (DMSO-$d_6$, Varian XL-400 MHz), [δppm]: 8.48 (t, 1H), 8.05–8.03 (d, 1H), 7.75–7.71 (t, 1H), 7.66 (s, 1H), 7.46–7.45 (d, 1H), 6.44 (s, 1H), 6.37 (s, 1H), 6.28–6.27 (m, 1H), 439 (m, 2H), 4.30 (r, 1H), 4.12 (m, 1H), 357 (d, 2H), 3.09 (m, 1H), 3.01–2.99 (m, 2H), 2.79 (m, 5H), 2.58–255 (d, 1H), 2.17–2.15 (m, 2H), 2.04–2.02 (m, 2H), 1.72–1.71 (m, 2H), 1.66–1.43 (m, br, 6H), 138–136 (m, br, 2H), 1.26–1.25 (m, br, 3H); IR (KBr); Vc=o 1815 and 1790 $cm^{-1}$.

Figure 18:
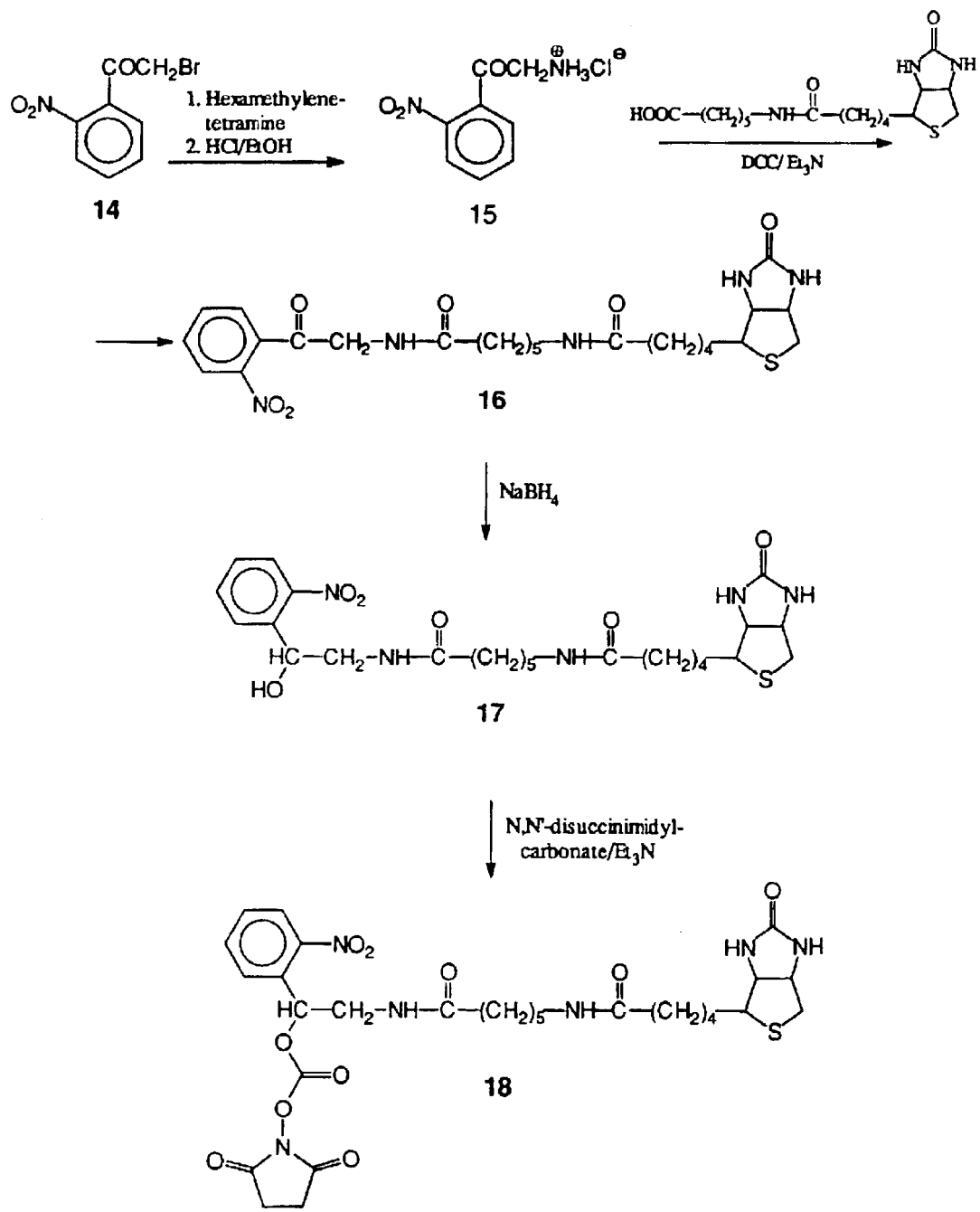
FIG. 18 Synthesis of photocleavable biotin-NHS ester, compound 18.

Synthesis of PCB-NHS Ester (FIG. 18):

2-Bromo-2'-nitroacetophenone ("14") (Aldrich Chemical; Milwaukee, Wis.) (1 g; 4.09 mmol) was converted into 2-amino-2'-nitroacetophenone hydrochloride ("15") by reaction with 1.05 eq. of hexamethylenetetramine and hydrolysis, and was coupled to 5-biotinamidocaproic acid (1.25 eq.) using DCC (1.5 eq.) in DMF to produce 2-(5-biotinamidocaproamido)-2'-nitroaceptophenone ("16") (about 52% yield) which was reduced (about 75% yield; "17" and converted into reactive NHS derivative ("18") 2-(5-biotinamidocaproamido)-2'-nitrophenylethyl-N-hydroxysuccinimidyl carbonate (about 69% yield) as described.

Synthesis of PCB-NHS Ester (FIG. 19):

3-amino-4-methoxybenzoic acid ("19") (Aldrich Chemical; Milwaukee, Wis.) (5 g or 29.9 mmol) was suspended in 40 ml acetic acid. Acetic anhydride (3 ml or 1:04 eq) was added by stirring. The reaction mixture was stirred for 2 hours at room temperature. 25 ml of 0.1N HCl was added and the precipitate was filtered off and washed with 3×10 ml of 0.1N HCl and 5×10 ml water to produce 5.97 g (about 95%). 3-(N-acetyl) amino-4-methoxybenzoic acid ("20") (5 g or 23.5 mmol) was added to 20 ml of fuming nitric acid at 0° C. on vigorous stirring. The solution was stirred at 0° C. for an additional hour and poured onto 200 g of ice. Precipitate was filtered off, washed with 5×20 mls of water and dried to produce 438 g (about 72%) of 2-nitro-4-methoxy-5 (N-acetyl)aminobenzoic acid ("21"), which was converted into 2-nitro-4-methoxy-5-(N-acetyl) aminoacetophenone ("22") (about 63% yield) as described. 2-nitro-4-methoxy-5-(N-acetyl)aminoacetophenone ("22") (1 g or 4,76 mmol) was dissolved in 5 ml of DMF and the solution was added to 5-biotinamidocaproyl chloride prepared separately from 5-biotinamidocaproic acid (1.55 g or 1 eq.) and 5 ml thionyl chloride. The reaction mixture was stirred overnight at room temperature and added to 100 ml of diethyl ether. Precipitate was purified using small silica gel column and a step gradient of MeOH in $CHCl_3$ to give 1.16 g (about 47%) of 2-nitro-4-methoxy-5-(5-biotinamidocaproamido) acetophenone ("23"). This intermediate was converted into its corresponding alcohol (about 85% yield) and into the reactive NHS ester derivative 5-(5-biotinamidocaproamido)4methoxy-1-(2-nitro) phenylethyl-N-hydroxysuccinimidyl carbonate ("25") with about a 69% yield.

Figure 21:
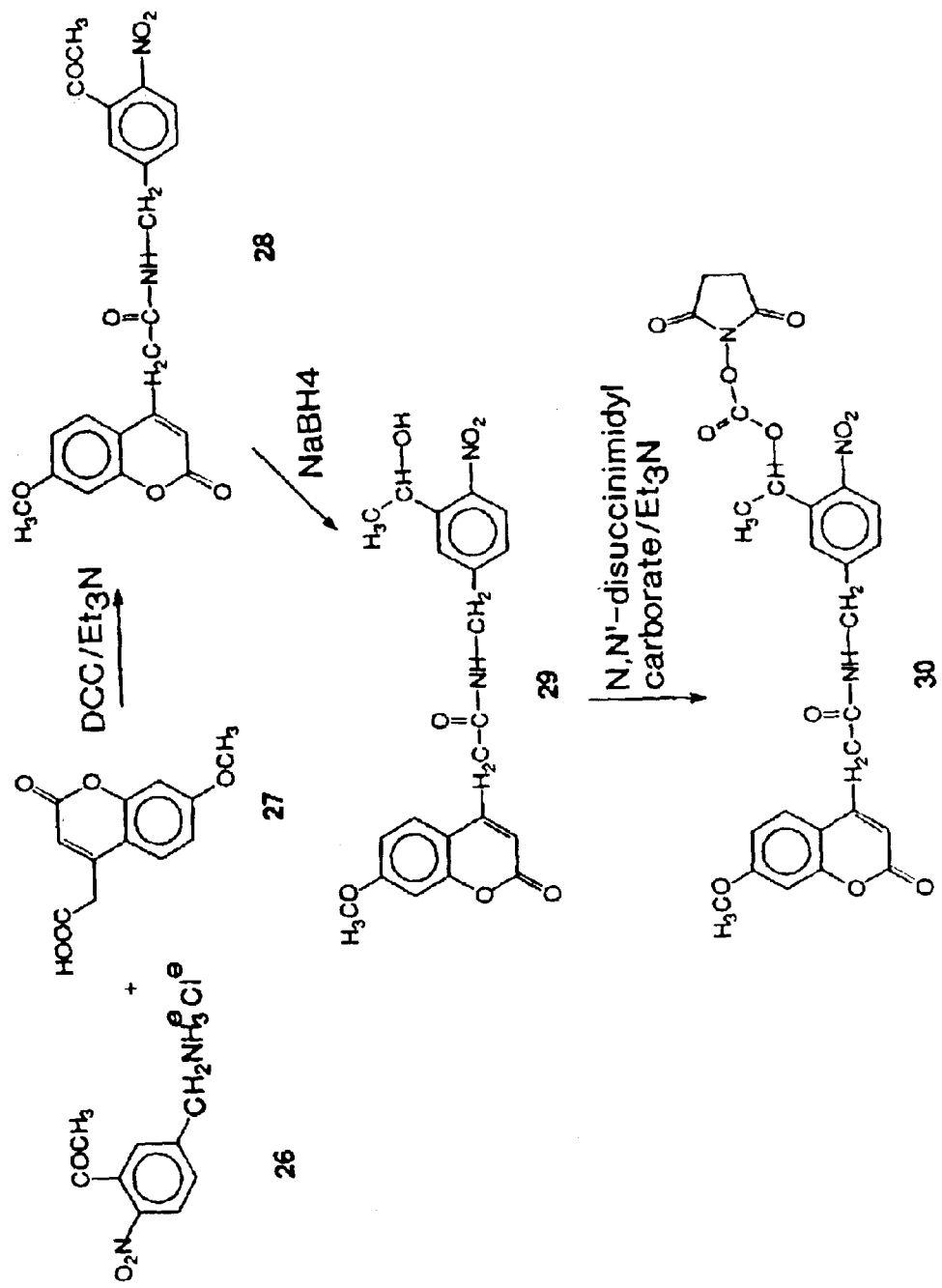
FIG. 21 Synthesis of photocleavable coumarin.

Synthesis of photocleavable coumarin (FIG. 21): 5-aminomethyl-2-nitroacetophenone hydrochloride ("26") (1.15 g or 5 mmol) was dissolved in 20 ml DMF. To this solution 7-Methoxycoumarin-4-acetic acid ("27") (Aldrich Chemical; Milwaukee, Wis.) (1.46 g or 1.25 eq.) and dicyclohexylcarbodiimide (1.55 g or 1.5 eq.) was added followed by triethylamine (0.7 ml or 1 eq.). The solution was stirred overnight at room temperature, 20 ml of $CHCl_3$ was added, the solution was washed with 0.1N $NaHCO_3$ (3×15 ml), and the organic layer was dried and purified on a silica gel column using step gradient of MeOH in $CH_2Cl_2$ to give 1.37 g (about 64%) of ("28"). Compound 28 (1 g or 2.33 mmol) was dissolved in 15 ml of 95% EtOH, the solution cooled to 0° C. and sodium borohydride (176 mg or 4 eq.) added. The solution was stirred at 0° C. for 1 hour and the reaction was quenched by addition of 1 ml acetone and neutralized with 0.1N HCl. The solution was then extracted with 3×15 ml of $CHCl_3$. Extracts were combined, dried, and purified on a silica gel column using step gradient of MeOH in $CH_2Cl_2$ to give 832 mg (about 83%) of compound 29. Compound 29 (1.29 g or 3 mmol) was dissolved in 10 ml of DMF-acetonitrile (1:1). N,N'-disuccinimidyl carbonate (Fluka Chemical; Ronkonkoma, N.Y.) (1.15 g or 15 eq.) was added which was followed with chloroform. The solution was washed with 3×15 ml of 0.1N $NaHCO_3$, solvents were evaporated to dryness and the residue recrystallized from acetonitrile to give 1.22 g (about 71%) of photocleavable coumarin NHS ester ("30").

Example 2

Synthesis of Photocleavable Conjugates—PCB-Amino Acids

PCB-amino acids were prepared by derivatization of the α-amino group of the amino acid. Derivatives were prepared from either PCB chloroformates or their corresponding N-hydroxysuccinimidyl esters and amino acids in a weakly alkaline media using a modification of the procedure by Sigler et al. (Biopolymers 22:2157, 1983; L. Lapatsanis et al., Can. J. Chem. 60:976, 1982; A Paquet, Can. J. Chem. 60:2711, 1977). This procedure was also used for the synthesis of ε-$NH_2$-PCB-Lys wherein the α-amino group of Lys is protected with Fmoc. PCB-amino acids were also prepared by carboxyl or hydroxy group derivatization. Briefly, carboxyl residues of aspartic acid and glutamic acid were esterified using PCB-OH. α-amino groups were protected as Fmoc derivatives and α-carboxyl groups were protected as t-butyl esters. Esterification of the carboxyl side chain was mediated using dicyclohexylcarbodiimide (DCC) (P. Sieber, Helv. Chim Acta 60:2711, 1977). Esterification was also carried out by reacting PCB-chloroformate with the hydroxyl side chains of appropriately protected threonine or serine residues (M. Bednarek et al., Int. J. Pept. Prot. Res. 21:196, 1983; H. Kessler et al., Tetrahedron 281, 1983).

Preparation and photocleavage of PCB-Leucine-Enkephaline: Leucine-enkephaline (Sigma Chemical; St. Louis, Mo.) (15.5 μmol/ml in 0.1N $NaHCO_3$, pH 8.0) and PCB-NHS ester (17 μmol/ml in DMF) were mixed and stirred overnight at room temperature. At this time HPLC analysis showed complete conversion of Leu-Enk into PCB-Leu-Enk. HPLC analysis was performed on a Waters System (Waters Chromatography; Marlboro, Mass.) comprising of U6K injector, 600 Controller, Novapak $C_{10}$-Column (3.9× 150 mm) and 996 Photodiode Array detector. Tests were performed using a linear gradient 30–45% of B over 10 minutes followed by 45% of B isocratic for 10 minutes.

PCB-Leu Enk (1.93 μmol/ml in phosphate buffer, pH 7.4) was irradiated with a long-wavelength, UV-lamp (Blak Ray XX-15 UV lamp; UVP Inc; San Gabriel, Calif.) at a distance of 15 cm (emission peak 365 nm, lamp intensity=1.1 $mW/cm^2$ at a distance of 31 cm). HPLC analysis showed complete photorelease of Leu-Enk within 5 minutes and confirmed authenticity of the released material on the basis of retention time and UV spectra.

PCB-Leu-Enk (10 nmoles) was incubated for 30 minutes in a suspension of monomeric-avidin agarose beads (15 nmoles). The suspension was spun-filtered for 3 minutes (16,000×). Binding efficiency was determined at about 94%. Sample was resuspended in phosphate buffer (2 ml) and irradiated as described. Released Leu-Enk was assayed using fluorescamine. Emission spectra were measured on a SLM 48000 fluorimeter using 380 nm excitation (λ=488 nm). Photorelease of Leu-Enk was quantitated after 5 minutes of illumination.

Example 3

Solid Phase Synthesis of PCB-Polypeptides

PCB-amino acids were incorporated into polypeptides by solid-support peptide synthesis. Standard method for employing base labile fluorenylmethyloxy (Fmoc) group for the protection of α-amino function and acid labile t-butyl derivatives for protection of α-carboxyl and reactive side chains were used. Synthesis was carried out on a polyamide-type resin. Amino acids were activated for coupling as symmetrical anhydrides or pentafluorophenyl esters (E. Atherton et al., Solid Phase Peptide Synthesis, IRL Press, Oxford, 1989). The PCB-amino acid for site-specific incorporation into polypeptide chain was derivatized with PCB moiety. Side chain PCB-derivatives, like ε-amino-Lys, side chain PCB-AA esters of Glu and Asp, and esters of Ser, Thr and Tyr, were incorporated within the polypeptide. These PCB-amino acids were stable during solid phase peptide synthesis, in 20% piperidine/DMF (Fmoc removal) and 1–95% trifluoroacetic acid (t-Bu, t-Boc removal, cleavage of the peptide from polyamide resin) (E. Atherton et al., Solid Phase Peptide Synthesis, IRL Press, Oxford, 1989).

Example 4

Detection and Isolation of Nascent Proteins

Misaminoacylation of tRNA: The general strategy used for generating misaminoacylated tRNA is shown in FIG. 10 and involves truncation of tRNA molecules, dinucleotide synthesis, aminoacylation of the dinucleotide and ligase mediated coupling.

Truncated tRNA molecules were generated by periodate degradation in the presence of lysine and alkaline phosphatase basically as described by Neu and Heppel (J. Biol. Chem. 239:2927–34, 1964). Briefly, 4 mmoles of uncharged E. coli $tRNA^{Lys}$ molecules (Sigma Chemical; St. Louis, Mo.) were truncated with two successive treatments of 50 mM sodium metaperiodate and 0.5 M lysine, pH 9.0, at 60° C. for 30 minutes in a total volume of 50 μl. Reaction conditions were always above 50° C. and utilized a 10-fold excess of metaperiodate. Excess periodate was destroyed treatment with 5 µl of 1M glycerol. The pH of the solution was adjusted to 8.5 by adding 15 µl of Tris-HCl to a final concentration of 0.1 M. The reaction volume was increased to 150 µl by adding 100 µl of water. Alkaline phosphatase (15 µl, 30 units) was added and the reaction mixture incubated again at 60° C. for two hours. Incubation was followed by ethanol precipitation of total tRNA, ethanol washing, drying the pellet and dissolving the pellet in 20 µl water. This process was repeated twice to obtain the truncated tRNA.

Dinucleotide synthesis was carried out basically as performed by Hudson (J. Org. Chem. 53:617–24, 1988), and can be described as a three step process, deoxycytidine protection, adenosine protection and dinucleotide synthesis.

Deoxycytidine protection: All reaction were conducted at room temperature unless otherwise indicated. First, the 5' and 3' hydroxyl groups of deoxycytidine were protected by reacting with 4.1 equivalents of trimethylsilyl chloride for 2 hours with constant stirring. Exocyclic amine function was protected by reacting it with 1.1 equivalents of Fmoc-Cl for 3 hours. Deprotection of the 5' and 3' hydroxyl was accomplished by the addition of 0.05 equivalents of KF and incubation for 30 minutes. The resulting product was produced at an 87% yield. Phosphate groups were added by incubating this compound with 1 equivalent of bis-(2-chlorophenyl) phosphorochloridate and incubating the mixture for 2 hours at 0° C. The yield in this case was 25–30%.

Adenosine protection: Trimethylsilyl chloride (4.1 equivalents) was added to adenosine residue and incubated for 2 hours, after which, 1.1 equivalents of Fmoc-Cl introduced and incubation continued for 3 hours. The TMS groups were deprotected with 0.5 equivalents of fluoride ions as described above. The Fmoc protected adenosine was obtained in a 56% yield. To further protect the 2'-hydroxyl, compound 22 was reacted with 1.1 equivalents of tetraisopropyl disiloxyl chloride (TIPDSCl$_2$) for 3 hours which produces compound 23 at a 68–70% yield. The compound was converted to compound 24 by incubation with 20 equivalents of dihydropyran and 0.33 equivalents of p-toluenesulfonic acid in dioxane for about 4–5 hours. This compound was directly converted without isolation by the addition of 8 equivalents of tetrabutyl ammonium fluoride in a mixture of tetrahydro-furan, pyridine and water.

Dinucleotide synthesis: The protected deoxycytidine, compound 20 (FIG. 19), and the protected adenosine were coupled by the addition of 1.1 equivalents of 2-chlorophenyl bis-(1-hydroxy benzotriazolyl) phosphate in tetrahydrofuran with constant stirring for 30 minutes. This was followed by the addition of 13 equivalents of protected adenosine in the presence of N-methylimidazole for 30 minutes. The coupling yield was about 70% and the proton NMR spectrum of the coupled product is as follows: (δ 8.76 m, 2H), (δ 8.0 m, 3H), (δ 7.8 m, 3H) (δ 7.6 m, 4H), (δ 7.5 m, 3H), (δ 7.4 m, 18H), (δ 7.0 m, 2H), (δ 4.85 m, 14H), (δ 4.25 m, 1H); (δ 3.6 m, 2H), (δ 3.2 m, 2H) (δ 2.9 m, 3H), (δ 2.6 m, 1H), (δ 2.0–1.2 m, 7H).

Aminoacylation of the dinucleotide was accomplished by linking the Nα-protected Nε-PCB-lys, to the dinucleotide with an ester linkage. First, the protected amino acid was activated with 6 equivalents of benzotriazol-1-yl-oxy tris-(dimethylamino) phosphonium hexafluoro phosphate and 60 equivalents of 1-hydroxybenzotriazole in tetrahydrofuran. The mixture was incubated for 20 minutes with continuous stirring. This was followed with the addition of 1 equivalent of dinucleotide in 3 equivalents N-methylimidazole, and the reaction continued at room temperature for 2 hours. Deprotection was carried out by the addition of tetramethyl guanidine and 4-nitrobenzaldoxime, and continuous stirring for another 3 hours. The reaction was completed by the addition of acetic acid and incubation, again with continuous stirring for 30 minutes at 0° C. which produced the aminoacylated dinucleotide.

Ligation of the tRNA to the aminoacylated dinucleotide was performed basically as described by T. G. Heckler et al. (Tetrahedron 40: 87–94, 1984). Briefly, truncated tRNA molecules (8.6 O.D.$_{260}$ units/ml) and aminoacylated dinucleotides (4.6 O.D.$_{260}$ units/ml), were incubated with 340 units/ml T4 RNA ligase for 16 hours at 4° C. The reaction buffer included 55 mM Na-Hepes, pH 7.5, 15 MM MgCl$_2$, 250 µM ATP, 20 µg/ml BSA and 10% DMSO. After incubation, the reaction mixture was diluted to a final concentration of 50 mM NaOAc, pH 45, containing 10 mM MgCl$_2$. The resulting mixture was applied to a DEAE-cellulose column (1 ml), equilibrated with 50 mM NaOAc, pH 45, 10 mM MgCl$_2$, at 4° C. The column was washed with 0.25 mM NaCl to remove RNA ligase and other non-tRNA components. The tRNA-containing factions were pooled and loaded onto a BD-cellulose column at 4° C., that had been equilibrated with 50 mM NaOAc, pH 4.5, 10 mM MgCl$_2$, and 1.0 M NaCl. Unreacted tRNA was removed by washes with 10 ml of the same buffer. Pure misaminoacylated tRNA was obtained by eluting the column with buffer containing 25% ethanol.

Preparation of extract: Wheat germ embryo extract was prepared by floatation of wheat germs to enrich for embryos using a mixture of cyclohexane and carbon tetrachloride (1:6), followed by drying overnight (about 14 hours). Floated wheat germ embryos (5 g) were ground in a mortar with 5 grams of powdered glass to obtain a fine powder. Extraction medium (Buffer I: 10 mM tris-acetate buffer, pH 7.6, 1 nM magnesium acetate, 90 mM potassium acetate, and 1 mM DTT) was added to small portions until a smooth paste was obtained. The homogenate containing disrupted embryos and 25 ml of extraction medium was centrifuged twice at 23,000×g. The extract was applied to a sephadex G-25 fine column and eluted in Buffer II (10 mM tris-acetate buffer, pH 7.6, 3 mM magnesium acetate, 50 mM potassium acetate, and 1 mM DTT). A bright yellow band migrating in void volume and was collected (S-23) as one ml fractions which were frozen in liquid nitrogen.

Preparation of template: Template DNA was prepared by linearizing plasmid pSP72-bop with EcoRI. Restricted linear template DNA was purified by phenol extraction and DNA precipitation. Large scale mRNA synthesis was carried out by in vitro transcription using the SP6-ribomax system (Promega; Madison, Wis.). Purified mRNA was denatured at 67° C. for 10 minutes immediately prior to use.

Cell-Free Translation Reactions: The incorporation mixture (100 µl) contained 50 µl of S-23 extract, 5 mM magnesium acetate, 5 mM tris-acetate, pH 7.6, 20 mM Hepes-KOH buffer, pH 7.5; 100 mM potassium acetate, 0.5 mM DTT, 0.375 mM GTP, 2.5 mM ATP, 10 mM creatine phosphate, 60 µg/ml creatine kinase, and 100 µg/ml mRNA containing the genetic sequence which codes for bacteriorhodopsin. Misaminoacylated PCB-lysine was added at 170 µg/ml and concentrations of magnesium ions and ATP were optimized. The mixture was incubated at 25° C. for one hour.

Isolation of Nascent Proteins Containing PCB-Lysine: Streptavidin coated magnetic Dynabeads M-280 (Dynal; Oslo, Norway), having a binding capacity of 10 µg of biotinylated protein per mg of bead. Beads at concentrations of 2 mg/mL were washed at least 3 times to remove stabilizing BSA. The translation mixture containing PCB-lysine incorporated into nascent protein was mixed with streptavidin coated beads and incubated at room temperature for 30 minutes. A magnetic field was applied using a magnetic particle concentrator (MPC) (Dynal; Oslo, Norway) for 0.5–1.0 minute and the supernatant removed with pipettes. The reaction mixture was washed 3 times and the magnetic beads suspended in 50 μof water.

Photolysis was carried out in a quartz cuvette using a Black-Ray long wave UV lamp, Model B-100 (UV Products, Inc.; San Gabriel, Calif.). The emission peak intensity was approximately 1100 $\mu W/cm^2$ at 365 nm. Magnetic capture was repeated to remove the beads. Nascent proteins obtained were quantitated and yields estimated at 70–95%.

Example 5

In Vitro Synthesis of Nascent Proteins using Photocleavable Conjugates

Post-Aminoacylation Linkage: A schematic representation of the steps involved in incorporation of PCB-amino acid for the detection and/or isolation of targets using post-aminoacylation linkage is shown in FIG. 10. *E. coli* tRNA$^{Lys}$ (Sigma Chem.; St. Louis, Mo.) was aminoacylated with lysine (A. E. Johnson et al., Proc. Natl. Acad. Sci. USA 75:3075, 1978). The NHS ester of PCB (compound 13) dissolved in dimethyl sulphoxide, was added at 0° C. to the solution of Lys-tRNA$^{Lys}$ and the modified tRNA purified using benzoylated DEAE-cellulose column (U. C. Kreig et al., Proc. Natl. Acad. Sci. USA 83:8604, 1986). mRNA was translated in a cell-free, wheat-germ system as described by Sonar et al. (Biochem. 32:13777, 1993). Nascent proteins containing PCB-lysine were purified by acetone precipitation to remove PCB-lysyl tRNA followed by magnetic capture of nascent proteins containing PCB-lysine using streptavidin coated magnetic beads. Material obtained after magnetic capture was irradiated for 10 minutes to release nascent protein.

Example 6

Synthesis of Photocleavable Conjugates—PCB Nucleotides

Synthesis of PCB-dUTP (FIG. 13A): 5-(3-Aminoallyl)-dUTP ammonium salt ("31") (Sigma Chemical; St. Louis, Mo.) (10 mg or 16.6 μmol) was dissolved in 200 μl of 0.1N NaHCO$_3$. To this solution was added a solution of PCB-NHS (compound 13; 12.5 mg or 1 eq.) in 100 μl of DMF. The reaction mixture was stirred overnight at room temperature, concentrated, and purified by reverse-phase semi-preparative HPLC (Novapak C$_{18}$ column; Waters Chromatography; Marlboro, Mass.) using a 10–50% linear gradient of acetonitrile (B) in 5 mM triethylammonium acetate (A) over 30 minutes. Fractions containing PCB-dUTP were pooled, lyophilized, and redissolved in TE buffer (pH 7.4) to a concentration of 5 mM, and the solution used for enzymatic incorporation into nucleic acids (yield about 56%). Similar procedures were used to prepare PCB-UTP, PCB-(d)ATP, and PCB-(d)CTP, using 5-(3-aminohexyl)-(deoxy)cytidine triphosphate, respectively.

Example 7

Synthesis of Photocleavable Conjugates—PCB Phosphoramidites

Figure 13B:
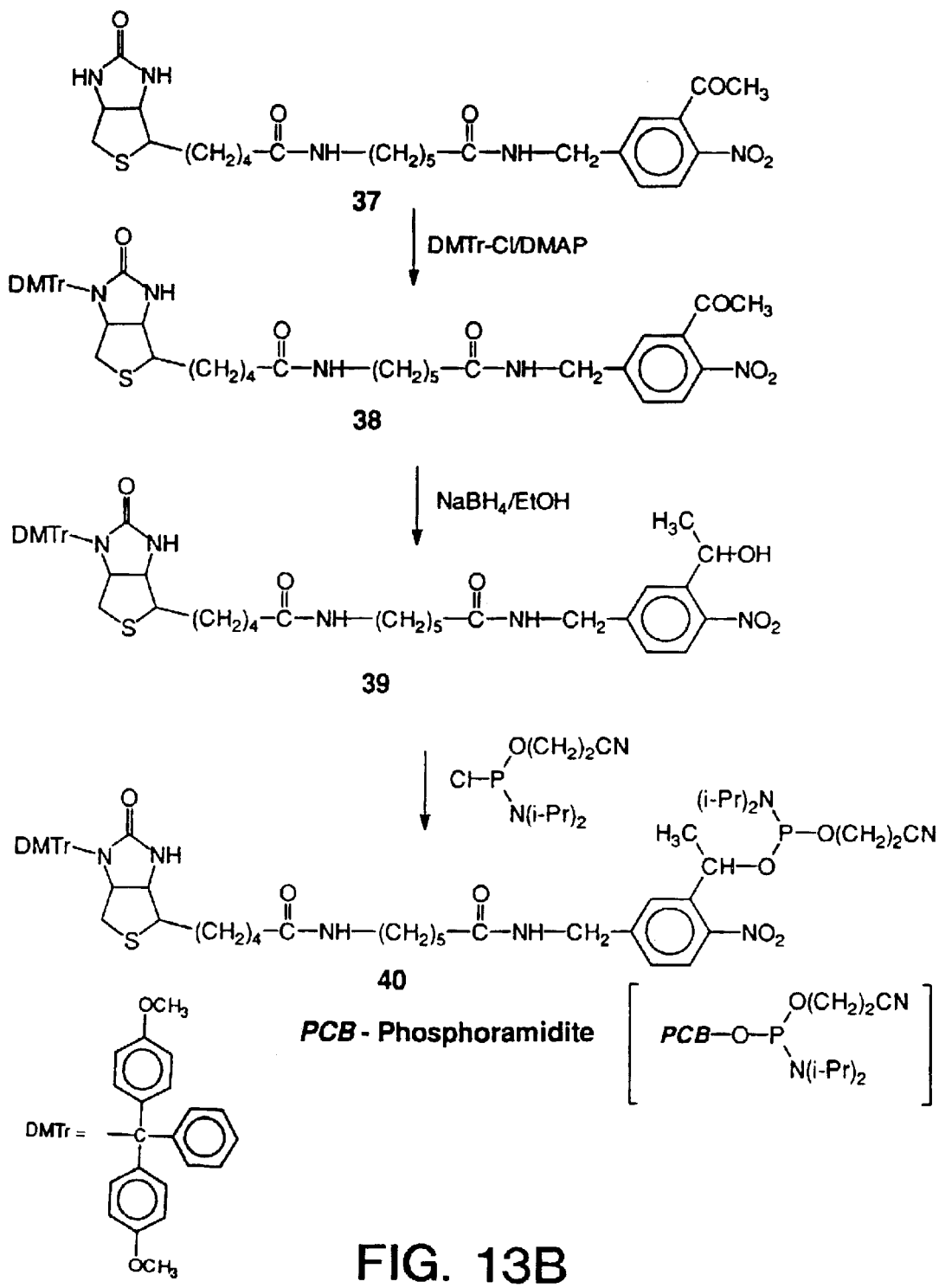
Figure 13C:
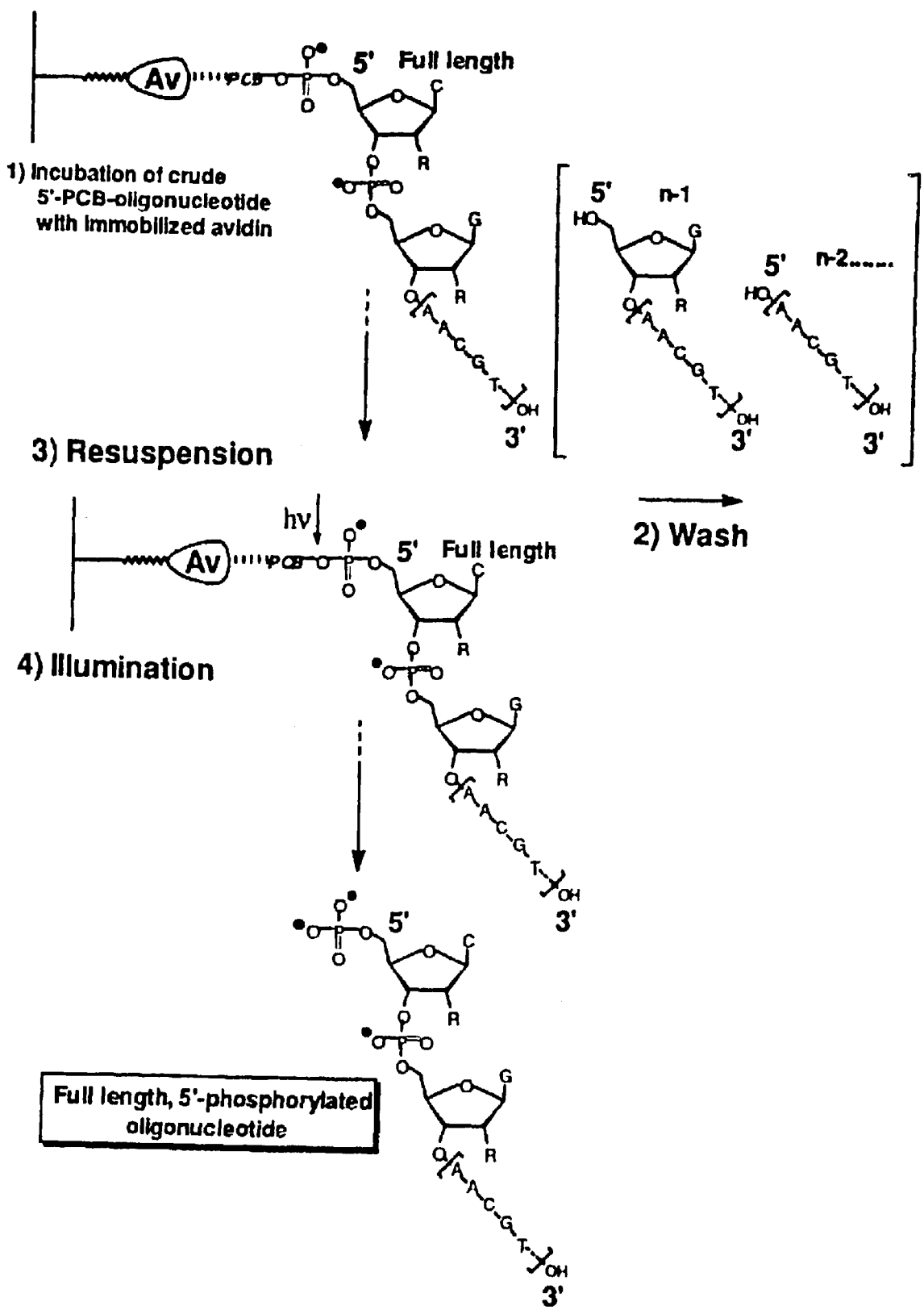

Synthesis of PCB-phosphoramidite (FIG. 13B): 5-(-5-biotinamidocapro-amidomethyl)-2-nitroacetophenone ("37") (534 mg or 1 mmol) was made anhydrous by coevaporation with pyridine (3×2 ml) and dissolved in 5 ml of pyridine. 4,4'-dimethoxytrityl chloride (406 mg or 1.2 eq) and 4-dimethylaminopyridine (6 mg or 0.05 eq) were added and the resulting solution stirred at room temperature for 24 hours. Ten ml of CHCl$_3$ and 20 ml of 0.1N aqueous NaHCO$_3$ were added, the layers formed separated and the organic layer dried, evaporated to dryness and purified on a silica gel column using 0–5% step gradient of MeOH in CHCl$_3$ to give 576 mg (about 69%) of compound 38. Intermediate 38 (836 mg or 1 mmol) was dissolved in 8 ml of 95% EtOH. The solution was cooled to 0° C. and vigorously stirred. To the solution was added NaBH$_4$ (19 mg or 2 eq.) in portions and the solution stirred for an additional 2 hours at room temperature. The reaction was quenched with 2 ml of acetone, 10 ml of CHCl$_3$ and 10 ml of 0.1N aqueous NaHCO$_3$ were added, the layers were separated, the organic layer was dried and evaporated to dryness to give 704 mg (about 84%) of compound 39 which was used without additional purification. Compound 39 (838 mg or 1 mmol) was dissolved in a mixture of CHCl$_3$ (5 ml) and diisophrophylethylamine (0.68 ml or 4 eq.). To this solution was added 2-cyanoethyl-N-,N-diisophropylchloraphosphoramidite (225 μl or 1 eq.) and the solution was stirred at room temperature for 1 hour. Ethyl acetate (5 ml) was added and the solution was washed with an NaCl solution (3×1 ml) and H$_2$O (2 ml). Dried solvents were removed in vacuo and purified on a silica gel column using step gradient of triethylamine in CH$_2$Cl$_2$ with a yield of 789 mg (about 74%).

Example 8

Chemical Synthesis of Oligonucleotides using PCB-Phosphoramidites

Automated Synthesis and Purification of Oligonucleotides Using 5' PCB-phosphoramidite: A 0.1M solution of 5'-PCB-phosphoramidite in anhydrous acetonitrile was prepared. The bottle with the solution was placed in the additional phosphoramidite port of the Applied Biosystem 392 DNA/RNA synthesizer. An oligodeoxynucleotide sequence was programmed and synthesized using 40 nmol CE column and standard synthesis protocol. The only modification necessary was extended detritylation (180 s) necessary for removal of trityl group from $N^1$ position of biotin. After synthesis, 5'-PCB-oligodeoxynucleotide was cleaved from solid support and deprotected by treatment with concentrated ammonia for 16 hours at 50° C. The crude oligonucleotide was freeze-dried and dissolved in 1 ml of phosphate buffer, pH 7.4. To this solution was added a suspension of monomeric avidin agarose beads (Sigma Chemical; St. Louis, Mo. ) (40 nmoles), and the mixture was incubated at room temperature for 1 hour. The suspension was filtered and washed with 3×1 ml phosphate buffer, resuspended in 3 ml of phosphate buffer and illuminated as described with gentle stirring for 10 minutes. The mixture was filtered, filtrate freeze-dried and redissolved (yield=3.8 OD$_{260}$).

Example 9

Enzymatic Synthesis of DNA and RNA using PCB-Nucleotides

Several enzymatic and chemical methods are available for biotinylation of nucleic acid probes. Enzymatic methods for incorporation of PCB-nucleotides into DNA include nick translation and replacement synthesis using T4 DNA polymerase. Terminal labeling of DNA can also be performed using terminal deoxynucleotidyl transferase. For PCB-labeling of RNA several RNA polymerase enzymes can be used. Nick translation was performed in the presence of PCB-dCTP based on the methods developed for biotinylation (P. R. Langer et al., Proc. Natl. Acad. Sci. USA 78:6633, 1981). Enzymatic tailing was used for double- and single-stranded DNA molecules. PCB nucleotides were added onto the 3'-end of the DNA. Biotinylated probes with internal biotin moieties form less stable hybrids than probes with external biotins and that the biotinylated probes synthesized in this manner have greater sensitivity than probes that are singly biotinylated at 5'-end (E. P. Diamandis et al., Clin. Chem. 37:625, 1991).

Preparation of PCB-labeled RNA: PCB-labeling of RNA was achieved in a standard phage T7 RNA polymerase transcription system using the PCB-UTP. To prepare single-stranded, biotinylated RNA as a probe, the appropriate DNA sequence was cloned into an appropriate vector which contains the T7 promoter upstream from the polylinker region. After linearization of the DNA clone downstream from the cloned insert, the RNA transcript of defined length was produced by the T7 RNA polymerase using ATP, CTP, GTP and PCB-UTP as substrates.

Example 10

Isolation of Hematopoietic Cells for Autologous Bone Marrow Transplantation.

Bone marrow is collected from the posterior iliac crest of normal healthy and leukemic patients into heparin. Low-density mononuclear cells are separated by sedimentation on Ficoll-Hypaque (Sigma Chemical; St. Louis, Mo.). $CD34^+$ cells are isolated using PCB-labeled anti-CD34 monoclonal antibodies (My10). Mononuclear marrow cells are placed at concentrations of $10^6$/ml in Iscove's Modified Dulbeco's Medium (IMDM; Irvine Scientific; Santa Anna, Calif.) with 20% FCS. Cells are cultured overnight under tissue culture conditions to remove adherent cells. Nonadherent cells are collected, washed twice in cold phosphate buffered saline (PBS), and diluted in PBS to $10^7$/ml. PCB-labeled anti-CD34 antibodies are added to the cell suspension at 5 $\mu$/ml and incubated at 4° C. for one hour with gentle intermittent mixing. After incubation, cells are washed twice in 5%-FCS/PBS and resuspended in the same volume. Streptavidin coated magnetic beads (Dynabeads; Oslo, Norway) are added to the suspension which is incubated at 4° C. for one hour with mixing. Beads and their associated cells are subjected to a magnet and separated from the suspension and placed in 5%-FCS/PBS. Photocleavage is carried out by irradiating the beads for 4 minutes with a long-wavelength, UV-lamp (Black Ray XX-15 UV lamp; UVP Inc; San Gabriel, Calif.) at a distance of 15 cm (emission peak 365 nm, lamp intensity=1.1 $mW/cm^2$ at a distance of 31 cm). Released beads are isolated by magnetic capture. The cell suspension is assayed for $CD34^+$ cells by staining with FTC-conjugated My10 antibody followed with FACS analysis and determined to be greater than 95% CD34 cells.

Example 11

Determination of the In Vivo Half-life of a Pharmaceutical Composition

Cell-free translation reactions are performed by mixing 10 $\mu$l of PCB-coumarin amino acid-$tRNA^{leu}$, prepared by chemical misaminoacylation as described above and suspended in TE at 1.7 mg/ml), 50 $\mu$l of S-23 extract, 10 $\mu$l water and 10 $\mu$l of a solution of 50 mM magnesium acetate, 50 mM Tris-acetate, pH 7.6, 200 mM Hepes-KOH buffer, pH 7.5; 1 M potassium acetate, 5 mM DTT, 3.75 mM GTP, 25 mM ATP, 100 mM creatine phosphate and 600 $\mu$g/ml creatine kinase. This mixture is kept on ice until the addition of 20 $\mu$l of 500 $\mu$g/ml human IL-2 mRNA (containing 26 leucine codons) transcribed and isolated from recombinant IL-2 cDNA. The mixture is incubated at 25° C. for one hour and placed on ice. One hundred $\mu$l of streptavidin coated magnetic Dynabeads (2 mg/ml) are added to the mixture which is placed at room temperature for 30 minutes. After incubation, the mixture is centrifuged for 5 minutes in a microfuge at 3,000×g or, a magnetic field is applied to the solution using a MPC. Supernatant is removed and the procedure repeated three times with TE. The final washed pellet is resuspended in 50 $\mu$l of 50 mM Tris-HCl, pH 75 and transferred to a quartz cuvette. UV light from a Black-Ray long wave UV lamp is applied to the suspension for approximately one second. A magnetic field is applied to the solution with a MPC for 1.0 minute and the supernatant removed with a pipette. The supernatant is sterile filtered and mixed with equal volumes of sterile buffer containing 50% glycerol, 1.8% NaCl and 25 mM sodium bicarbonate. Protein concentration is determined by measuring the $O.D._{260}$.

0.25 ml of the resulting composition is injected iv. into the tail vein of 2 Balb/c mice at concentrations of 1 mg/ml. Two control mice are also injected with a comparable volume of buffer. At various time points (0, 5 minutes, 15 minutes, 30 minutes, 60 minutes, 2 hours and 6 hours), 100 $\mu$l serum samples are obtained from foot pads and added to 400 $\mu$l of 0.9% saline. Serum sample are added to a solution of dynabeads (2 mg/ml) coated with anti-coumarin antibody and incubated at room temperature for 30 minutes. A magnetic field is applied to the solution with a MPC for 1 minute and the supernatant removed with a pipette. Fluorescence at 470 nm is measured and the samples treated with monoclonal antibody specific for rat IL-2 protein. IL-2 protein content is quantitated for each sample and equated with the amount of fluorescence detected. From the results obtained, in vivo IL-2 half-life is accurately determined.

Example 12

Polymerase Chain Reactions with PCB

The steps involved in the PCR amplification DNA sequences using PCB are shown in FIG. 12. The experimental method described below is based on a combination of protocols described (Y. Lo et al., Nucl. Acids Res. 16:719, 1988; R. K. Saiki et al., Sci. 239:487, 1988). PCB-dCTP synthesized was added (50 $\mu$M) to the mixture of dATP, dGTP, dTTP (all 200 $\mu$M) and dCTP (150 $\mu$M). The reaction mixture consisted of target DNA source (total genomic DNA isolated), flanking primers and the thermostable polymerase (Taq polymerase). The reaction mixture was subjected to 25–30 cycles of amplification. Samples were heated from 70–95° C. for a 1 minute period to denature DNA and cooled to 40° C. for 2 minutes to anneal the primers. Samples were again heated to 70° C. for 1 minute to activate the polymerase and incubated at this temperature for 0.5 minutes to extend the annealed primers. After the last cycle, samples were incubated for an additional 5 to 10 minutes at 37° C. to ensure that the final extension was complete. Magnetic capture of the nucleic acids was performed using streptavidin coated magnetic beads. The captured material was washed with appropriate buffers and resuspended at the desired concentration. Samples were illuminated for 10 minutes to release the PCR product in an unmodified form.

Nucleic acids in either immobilized form or in solution form were detected or separated (purified) using PCB-labeled nucleic acid probes. Hybridization was carried out to obtain DNA:DNA, DNA:RNA and RNA:RNA hybrids. These experiments involve first the hybridization with PCB-labeled probes followed by capturing the hybrids using streptavidin coated immobilized supports. These hybrids were washed free of initial undesired components and were released from the immobilized support using irradiation (G. Gebeyehu et al., Nucl. Acids Res. 15:4513, 1987; T. Ito et al., Nucl. Acids Res. 20:3524, 1992). Hybridization of ssDNA molecules with PCB-probe involved incubation of these components in a hybridization buffer at 42° C. for 30 minutes. Hybridization conditions were optimized for each probe and experimental system. PCB-labeled probes had lower melting temperatures than radiolabeled probes and require slightly modified hybridization conditions. These hybrids were selectively removed from the reaction components using immobilized streptavidin (Dynabeads M280 streptavidin). Photochemical release of complexes resulted in the isolation of pure hybrid.

Example 13

Synthesis of PCB—Liposomes

Incorporation of PCB-Lipids into liposomes: PCB-lipids were mixed with conventional lipids in chloroform:methanol at a ratio of 2:1. The lipid mixture was evaporated to dryness under nitrogen and the dried lipids suspended in DMSO as solvent to a final concentration of 1 mg/ml. Liposomes were sonication under nitrogen in an ice-cold chamber for 10 minutes. The resulting suspension was centrifuged for 20 minutes at 10,000 rpm and the supernatant containing PCB-liposomes was ready for use. Satisfactory results were obtained with as little as 5% (mol equivalent) PCB-lipids. The structural chemical formulas for PCB-phosphatidylathanolamine and PCB-phosphatidylserine are shown in FIG. 16.

Example 14

PCB for In Situ Hybridization

The general methodology for in situ hybridization reactions can be divided into sample preparation, selection of indicator molecule and probe, hybridization, washing, and autoradiography and detection.

Sample preparation: Frozen tissue sections of 5 to 6 μm are mounted on gelatin coated microscope slides and air dried for 30 min prior to fixation. This is followed by fixation of DNA or RNA using either glutaraldehyde or paraformaldehyde. During these fixing steps optional denaturing steps (e.g. 100° C. for 5 minutes) followed by quick immersion in ice cold buffer (necessary if dsDNA or dsRNA is the target of the reaction) can be introduced. In case of cells and cell-cultures, these cells ($1 \times 10^6$ cells) are deposited on gelatin coated slides by cytocentrifugation or smearing. The cells are air dried and fixed for DNA or RNA.

Selection of indicator molecule and probe: Although isotopic detection offers several advantages over the use of non-isotopic methods, the latter can be used effectively. Labeled probes can be generated by a variety of techniques ranging from synthetic oligonucleotides to excised plasmid inserts.

Hybridization: ISH follows the same general principles as a solution and filter hybridization. Standard reaction temperatures are approximately $T_m - 25°$ C. ($T_m$ is the temperature at which 50% of hybrids dissociate). The reaction temperature is reduced to a level compatible with the preservation of histological detail by the addition of 50% formamide to the hybridization mixture. Thus, for typical DNA-DNA hybridization reactions, the temperature is 37° C., for RNA-DNA 44° C., and for RNA-RNA 50°. The surface of the microscope slide supporting the sample is gently blown by a stream of air, and the final hybridization mix is pipetted over the surface. The film is then incubated flat in a bath of paraffin oil for the required time and temperature.

Washing: The paraffin oil is drained and excess of oil is removed by washing twice with chloroform, and the slides are air dried. A high stringency wash is given to reduce background.

Autoradiography and detection: Detection is carried out either using X-ray film or emulsion coated cover-slips in cases of radioactive isotopically labeled probes, and other methods in the case of enzymatic detection methods.

Example 15

Isolation of Different Populations Cells with Agents which Photocleaved at Distinct Wavelengths Two distinct conjugates are created, each with a different antigen-specific antibody coupled to a different bioreactive agent. Conjugate A comprises compound 30 (FIG. 21), a PCB bioreactive agent, coupled to an antibody specific for the cell surface marker CD34 (a stem cell marker), and will photocleave with radiation at 300 nm. Conjugate B comprises compound 25 (FIG. 19), a PCB bioreactive agent, coupled to an antibody specific for the cell surface marker CD3 (a T cell marker), and will photocleave with radiation at 400 nm.

Conjugates A and B are incubated, in duplicate, with samples of peripheral blood obtained from healthy human volunteers. Incubations are performed at room temperature (22° C.) with gentle rocking to provide maximal antibody-antigen contact. After a 30 minute incubation, cells are placed in 100 mm tissue culture dishes coated with streptavidin and incubated for an additional 30 minutes. Upon streptavidin-biotin binding, plates are gently washed in PBS to remove any cells which do not adhere.

After washing, one set of plates is treated with electromagnetic radiation at 300 nm and the released cells collected. This set is then treated with electromagnetic radiation at 400 nm and the cells released at this frequency collected. A second set of plates is treated with radiation at 400 nm, released cells are collected, the plates are again treated at 300 nm and the released cells again collected. By determining the number of cells collected after each treatment and from each set of plates, the number of cells in a sample of peripheral blood which carry the cell surface marker for CD34, CD3, and both CD34 and CD3 is determined.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

What is claimed is:

1. A method, comprising:
   a) providing a tRNA molecule, nucleic acid derived from a biological sample, and a marker;
   b) aminoacylating said tRNA molecule with said marker to create a misaminoacylated tRNA;

c) introducing said misaminoacylated tRNA and said nucleic acid derived from a biological sample into a translation system under conditions such that said marker is incorporated into a nascent protein; and d) screening for disease, said screening comprising detecting said marker.

2. The method of claim 1, wherein the nascent protein is selected from recombinant gene products, gene fusion products, enzymes, cytokines, carbohydrate and lipid binding proteins, nucleic acid binding proteins, hormones, immunogenic proteins, human proteins, viral proteins, bacterial proteins, parasitic proteins and fragments and combinations thereof.

3. The method of claim 1, wherein the translation system comprises a cellular or cell free translation system.

4. The method of claim 3, wherein the cellular translation system is selected from the group consisting of tissue culture cells, primary cells, cells in vivo, isolated immortalized cells, human cells and combinations thereof.

5. The method of claim 3, wherein the cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof.

6. The method of claim 1, wherein the tRNA molecule is aminoacylated by chemical or enzymatic misaminoacylation.

7. The method of claim 1, wherein said disease is selected from the group consisting of infections, neoplasias and genetic disorders.

8. The method of claim 1, wherein said biological sample is selected from the group consisting of blood, serum, tissue, urine, stool, nasal cells and spinal fluid.

9. The method of claim 1, wherein prior to step (c) said nucleic acid is amplied in a polymerase chain reaction.

10. The method of claim 1, wherein said marker comprises a detectable label.

11. The method of claim 1, wherein said marker comprises a coupling agent.

12. The method of claim 11, wherein said coupling agent is selected from the group consisting of biotin and derivatives thereof.

13. The method of claim 11, wherein said coupling agent comprises an antigenic site.

14. The method of claim 11, wherein said coupling agent binds to surfaces, said surfaces selected from the group consisting of resin surfaces, bead surfaces, ceramic surfaces, glass surfaces, particle surfaces, and polymer surfaces.

15. The method of claim 1, wherein said marker is a photocleavable marker.

16. The method of claim 15, wherein said photocleavable marker is photocleavable biotin.

17. The method of claim 16, wherein said photocleavable marker comprises an amino acid coupled via a photocleavable linkage to a detectable label.

18. The method of claim 15, wherein said photocleavable marker comprises an amino acid coupled via a photocleavable linkage to a coupling agent.

19. The method of claim 1, wherein two or more different misaminoacylated tRNAs are introduced to the translation system at step (c).

20. The method of claim 1, wherein said detecting of step (d) comprises using an electromagnetic field.

21. A method of screening for a genetic disorder, comprising:

a) providing a tRNA molecule, nucleic acid derived from a biological sample, and a detectable label;

b) aminoacylating said tRNA molecule with said detectable label to create a misaminoacylated tRNA;

c) introducing said misaminoacylated tRNA and said nucleic acid derived from a biological sample into a translation system under conditions such that said detectable label is incorporated into a nascent protein; and d) screening for a genetic disorder, said screening comprising detecting said detectable label.

22. The method of claim 21, wherein the nascent protein is selected from recombinant gene products, gene fusion products, enzymes, cytokines, carbohydrate and lipid binding proteins, nucleic acid binding proteins, hormones, immunogenic proteins, human proteins, viral proteins, bacterial proteins, parasitic proteins and fragments and combinations thereof.

23. The method of claim 21, wherein the translation system comprises a cellular or cell-free translation system.

24. The method of claim 23, wherein the cellular translation system is selected from the group consisting of tissue culture cells, primary cells, cells in vivo, isolated immortalized cells, human cells and combinations thereof.

25. The method of claim 23, wherein the cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof.

26. The method of claim 21, wherein the tRNA molecule is aminoacylated by chemical or enzymatic misaminoacylation.

27. The method of claim 21, wherein said genetic disorder is familial adenomatous polyposis.

28. The method of claim 21, wherein said biological sample is selected from the group consisting of blood, serum, tissue, urine, stool, nasal cells and spinal fluid.

29. The method of claim 21, wherein prior to step (c) said nucleic acid is amplied in a polymerase chain reaction.

30. The method of claim 21, wherein said detectable label comprises a fluorescent label.

31. The method of claim 21, wherein said detectable label comprises a coupling agent.

32. The method of claim 31, wherein said coupling agent is selected from the group consisting of biotin and derivatives thereof.

33. The method of claim 31, wherein said coupling agent comprises an antigenic site.

34. The method of claim 31, wherein said coupling agent binds to surfaces, said surfaces selected from the group consisting of resin surfaces, bead surfaces, ceramic surfaces, glass surfaces, particle surfaces, and polymer surfaces.

35. The method of claim 31, wherein two or more different misaminoacylated tRNAs are introduced to the translation system at step (c).

36. The method of claim 31, wherein said detecting of step (d) comprises using an electromagnetic field.

* * * * *